US012760323B2

(12) United States Patent
Xue et al.

(10) Patent No.: US 12,760,323 B2
(45) Date of Patent: Oct. 13, 2026

(54) PRODUCER CELL AND PACKAGING CELL FOR RETROVIRAL VECTOR AND PREPARATION METHOD THEREOF

(71) Applicant: Shenzhen Eureka Biotechnology Co., Ltd., Nanshan Shenzhen (CN)

(72) Inventors: Bofu Xue, Nanshan Shenzhen (CN); Yinhui Yang, Nanshan Shenzhen (CN); Ke Liu, Nanshan Shenzhen (CN)

(73) Assignee: Shenzhen Eureka Biotechnology Co., Ltd., Shenzhen (CN)

( * ) Notice: Subject to any disclaimer, the term of this patent is extended or adjusted under 35 U.S.C. 154(b) by 963 days.

(21) Appl. No.: 17/766,684

(22) PCT Filed: Sep. 16, 2020

(86) PCT No.: PCT/CN2020/115522

§ 371 (c)(1),
(2) Date: Apr. 5, 2022

(87) PCT Pub. No.: WO2021/218000

PCT Pub. Date: Nov. 4, 2021

(65) Prior Publication Data

US 2023/0051793 A1 Feb. 16, 2023

(30) Foreign Application Priority Data

Apr. 30, 2020 (CN) ......................... 202010366440.4

(51) Int. Cl.
*C12N 15/86* (2006.01)
*C12N 5/071* (2010.01)

(52) U.S. Cl.
CPC ........... *C12N 15/86* (2013.01); *C12N 5/0686* (2013.01); *C12N 2510/02* (2013.01); *C12N 2740/15021* (2013.01); *C12N 2740/15043* (2013.01); *C12N 2740/15052* (2013.01)

(58) Field of Classification Search
None
See application file for complete search history.

(56) References Cited

U.S. PATENT DOCUMENTS

| | | | |
|---|---|---|---|
| 6,218,185 | B1 | 4/2001 | Shirk et al. |
| 6,489,458 | B2 | 12/2002 | Hackett et al. |
| 6,551,825 | B1 | 4/2003 | Shirk et al. |
| 6,808,905 | B2 | 10/2004 | McArthur et al. |
| 6,962,810 | B2 | 11/2005 | Fraser et al. |
| 7,105,343 | B1 | 9/2006 | Fraser et al. |
| 7,129,083 | B1 | 10/2006 | Handler |
| 7,148,203 | B2 | 12/2006 | Hackett et al. |
| 7,160,682 | B2 | 1/2007 | Hackett et al. |
| 7,179,903 | B2 | 2/2007 | McArthur et al. |
| 7,332,333 | B2 | 2/2008 | Bremel et al. |
| 7,745,179 | B2 | 6/2010 | McArthur et al. |
| 7,745,592 | B2 | 6/2010 | Massie et al. |
| 7,935,788 | B2 | 5/2011 | Malenfant et al. |
| 7,985,739 | B2 | 7/2011 | Kay |
| 8,163,894 | B2 | 4/2012 | Massie et al. |
| 8,227,432 | B2 | 7/2012 | Hackett et al. |
| 8,252,556 | B2 | 8/2012 | Malenfant et al. |
| 8,383,364 | B2 | 2/2013 | Berkhout et al. |
| 8,399,643 | B2 | 3/2013 | Ostertag et al. |
| 8,592,211 | B2 | 11/2013 | Brivanlou et al. |
| 8,728,759 | B2 | 5/2014 | Xu et al. |
| 8,741,340 | B2 | 6/2014 | Kusk et al. |
| 9,121,037 | B2 | 9/2015 | Kusk et al. |
| 9,127,283 | B2 | 9/2015 | Bisgrove et al. |
| 9,175,295 | B2 | 11/2015 | Kaminaka et al. |
| 9,181,556 | B2 | 11/2015 | Bujard et al. |
| 9,228,180 | B2 | 1/2016 | Izsvak et al. |
| 9,428,767 | B2 | 8/2016 | Minshull et al. |
| 9,534,234 | B2 | 1/2017 | Minshull et al. |
| 9,546,382 | B2 | 1/2017 | Ostertag et al. |
| 9,574,209 | B2 | 2/2017 | Minshull et al. |
| 9,580,697 | B2 | 2/2017 | Minshull et al. |
| 9,670,503 | B2 | 6/2017 | Craig |
| 9,783,790 | B2 | 10/2017 | Craig |
| 9,840,696 | B2 | 12/2017 | Izsvak et al. |
| 9,840,718 | B2 | 12/2017 | Solodushko et al. |
| 9,884,023 | B2 | 2/2018 | Kusk et al. |
| 10,041,077 | B2 | 8/2018 | Minshull et al. |
| 10,087,463 | B2 | 10/2018 | Fraser et al. |
| 10,131,885 | B2 | 11/2018 | Ostertag et al. |

(Continued)

FOREIGN PATENT DOCUMENTS

| | | |
|---|---|---|
| CN | 101297031 B | 6/2013 |
| CN | 103131672 A | 6/2013 |

(Continued)

OTHER PUBLICATIONS

Broussau, et al. Inducible packaging cells for large-scale production of lentiviral vectors in serum-free suspension culture. Molecular Therapy. 16(3):500-507. Mar. 2008. (Year: 2008).*

Randolph, et al. An all-in-one, Tet-On 3G inducible PiggyBac system for human pluripotent stem cells and derivatives. Scientific Reports. 2017. (Year: 2017).*

Iwata, et al. A novel tetracycline-responsive transgenic mouse strain for skeletal muscle-specific gene expression. Skeletal Muscle. 8(33):1-8. 2018. (Year: 2018).*

Takara Bio. Tet-On 3G Inducible Expression Systems Product Information Sheet. 2010. (Year: 2010).*

(Continued)

*Primary Examiner* — Allison M Fox
*Assistant Examiner* — Gina Pronzati
(74) *Attorney, Agent, or Firm* — FISH & RICHARDSON P.C.

(57) ABSTRACT

The present disclosure relates to a method for constructing a producer cell and the producer cell obtained by the method, wherein the producer cell is for producing a retroviral vector carrying a nucleic acid fragment of interest.

15 Claims, 14 Drawing Sheets

Specification includes a Sequence Listing.

(56) References Cited

U.S. PATENT DOCUMENTS

| | | | | |
|---|---|---|---|---|
| 10,174,309 | B2 | 1/2019 | Grawunder | |
| 10,233,454 | B2 | 3/2019 | Minshull et al. | |
| 10,287,559 | B2 | 5/2019 | Ostertag et al. | |
| 10,344,285 | B2 | 7/2019 | Minshull et al. | |
| 10,415,022 | B2 | 9/2019 | Craig | |
| 10,435,696 | B2 | 10/2019 | Minshull et al. | |
| 10,888,526 | B2 | 1/2021 | Kusk et al. | |
| 10,927,384 | B2 | 2/2021 | Minshull et al. | |
| 2002/0173634 | A1 | 11/2002 | Fraser et al. | |
| 2009/0042297 | A1 | 2/2009 | Sl. | |
| 2010/0240133 | A1 | 9/2010 | Brivanlou et al. | |
| 2017/0226531 | A1 | 8/2017 | Craig | |
| 2018/0305715 | A1 | 10/2018 | Gray | |
| 2019/0055568 | A1* | 2/2019 | Pulé | C12N 15/86 |
| 2019/0169638 | A1 | 6/2019 | Izsvák et al. | |
| 2019/0225674 | A1 | 7/2019 | Lu | |
| 2019/0233843 | A1 | 8/2019 | Shedlock | |
| 2020/0123505 | A1 | 4/2020 | Johnson et al. | |
| 2020/0157567 | A1 | 5/2020 | Cawood et al. | |
| 2020/0199627 | A1 | 6/2020 | Gu et al. | |
| 2020/0208121 | A1 | 7/2020 | Hewitt et al. | |
| 2020/0283857 | A1 | 9/2020 | Tang et al. | |
| 2020/0308600 | A1 | 10/2020 | Puléet al. | |
| 2021/0062220 | A1 | 3/2021 | Shin et al. | |
| 2021/0115453 | A1 | 4/2021 | Shedlock et al. | |

FOREIGN PATENT DOCUMENTS

| | | | | |
|---|---|---|---|---|
| CN | 108291208 | A | 7/2018 | |
| CN | 108384811 | A | 8/2018 | |
| CN | 108611326 | | 10/2018 | |
| CN | 109072257 | A | 12/2018 | |
| CN | 109072258 | A | 12/2018 | |
| CN | 109312361 | A | 2/2019 | |
| CN | 109312365 | A | 2/2019 | |
| CN | 113195725 | A | 7/2019 | |
| CN | 104640985 | B | 5/2021 | |
| CN | 113195712 | A | 7/2021 | |
| CN | 113396222 | A | 9/2021 | |
| EP | 1276889 | B1 | 10/2005 | |
| EP | 1395293 | B1 | 7/2009 | |
| EP | 1385946 | B1 | 12/2009 | |
| EP | 097392 | B1 | 5/2010 | |
| EP | 1954811 | B1 | 6/2011 | |
| EP | 2160461 | B1 | 8/2012 | |
| EP | 2352833 | B1 | 3/2013 | |
| EP | 2692865 | | 12/2014 | |
| EP | 1572912 | B1 | 9/2015 | |
| EP | 2389435 | B1 | 11/2015 | |
| EP | 1797186 | B1 | 5/2016 | |
| EP | 2401367 | B1 | 11/2016 | |
| EP | 3380604 | A1 | 6/2017 | |
| EP | 2643459 | B1 | 9/2017 | |
| EP | 3019618 | B1 | 10/2018 | |
| EP | 3420090 | A1 | 1/2019 | |
| EP | 3361869 | A1 | 4/2019 | |
| EP | 3489353 | A1 | 5/2019 | |
| EP | 3701024 | A1 | 9/2020 | |
| EP | 3129487 | B1 | 10/2020 | |
| EP | 3430149 | | 5/2021 | |
| EP | 3359671 | B1 | 8/2021 | |
| EP | 3856910 | A1 | 8/2021 | |
| JP | 2010-531650 | | 9/2010 | |
| JP | 2015-043785 | | 6/2015 | |
| JP | 2019-506173 | | 3/2019 | |
| JP | 2019-509066 | | 4/2019 | |
| JP | 2019-509764 | | 4/2019 | |
| WO | WO1998040510 | A1 | 9/1998 | |
| WO | WO2000068399 | A2 | 11/2000 | |
| WO | WO2000075347 | A2 | 12/2000 | |
| WO | WO2001030965 | A2 | 5/2001 | |
| WO | WO2001081565 | A2 | 11/2001 | |
| WO | WO2002002738 | A2 | 1/2002 | |
| WO | WO2002088346 | A2 | 11/2002 | |
| WO | WO2002092134 | A1 | 11/2002 | |
| WO | WO2003089618 | A2 | 10/2003 | |
| WO | WO2004009792 | A2 | 1/2004 | |
| WO | WO2005007803 | A2 | 1/2005 | |
| WO | WO2005072129 | A2 | 8/2005 | |
| WO | WO2006037215 | A1 | 4/2006 | |
| WO | WO2006122442 | | 11/2006 | |
| WO | WO2007004642 | A1 | 1/2007 | |
| WO | WO2007058527 | A2 | 5/2007 | |
| WO | WO2008079608 | A1 | 7/2008 | |
| WO | WO2009003671 | A2 | 1/2009 | |
| WO | WO2010037593 | A1 | 4/2010 | |
| WO | WO2010083841 | A2 | 7/2010 | |
| WO | WO2010085699 | A2 | 7/2010 | |
| WO | WO2010099296 | | 9/2010 | |
| WO | WO2010099296 | A1 | 9/2010 | |
| WO | WO2010099301 | A2 | 9/2010 | |
| WO | WO2011153440 | A2 | 12/2011 | |
| WO | WO-2012028681 | A1 * | 3/2012 | C12N 15/00 |
| WO | WO2012071549 | A2 | 5/2012 | |
| WO | WO2012074758 | A1 | 6/2012 | |
| WO | WO2013012824 | A2 | 1/2013 | |
| WO | WO2014013026 | A1 | 1/2014 | |
| WO | WO2014194130 | A1 | 12/2014 | |
| WO | WO2014196931 | A1 | 12/2014 | |
| WO | WO2015006700 | A1 | 1/2015 | |
| WO | WO2015157386 | A1 | 10/2015 | |
| WO | WO2015157579 | A2 | 10/2015 | |
| WO | WO2016197570 | A1 | 12/2016 | |
| WO | WO2017046259 | A1 | 3/2017 | |
| WO | WO2017054647 | A1 | 4/2017 | |
| WO | WO2017062668 | A2 | 4/2017 | |
| WO | WO2017089308 | A1 | 6/2017 | |
| WO | WO 2017144892 | | 8/2017 | |
| WO | WO2017147538 | A1 | 8/2017 | |
| WO | WO2017158029 | | 9/2017 | |
| WO | WO2017158029 | A1 | 9/2017 | |
| WO | WO2018013551 | A1 | 1/2018 | |
| WO | WO2018189535 | A1 | 10/2018 | |
| WO | WO2018192981 | A1 | 10/2018 | |
| WO | WO2019046815 | A1 | 3/2019 | |
| WO | WO2019081935 | A1 | 5/2019 | |
| WO | WO2019099769 | A1 | 5/2019 | |
| WO | WO2019175600 | | 9/2019 | |
| WO | WO-2020014366 | A1 * | 1/2020 | C07K 16/2803 |
| WO | WO2020068631 | A1 | 4/2020 | |
| WO | WO2020123327 | A1 | 6/2020 | |
| WO | WO2020132177 | A1 | 6/2020 | |
| WO | WO2021041322 | A1 | 3/2021 | |
| WO | WO2021127076 | A1 | 6/2021 | |

OTHER PUBLICATIONS

Cui et al., “991. Generation of Stable Producer Cell Lines (PCL) of Lentiviral Vector (LV) Using PiggyBac Transposase,” Molecular Therapy, Apr. 28, 2020, 28(4S1):430-431.

Akef et al., “Splicing promotes the nuclear export of beta-globin mRNA by overcoming nuclear retention elements,” RNA, Nov. 2015, 21(11):1908-1920.

Gao, “Establishment of a Packaging Cell Line for Lentivirus Vector,” China Master's Theses Full-text Database, Jan. 2007, 2007(1):15: 51 pages (with English abstract).

Gossen et al., “Tight control of gene expression in mammalian cells by tetracyclineresponsive promoters,” Proceedings of the National Academy of Sciences of the United States of America, Jun. 1992, 89(12):5547-5551.

International Search Report and Written Opinion in International Appln. No. PCT/CN2020/115522, dated Feb. 3, 2021, 16 pages (with English translation).

Kaul et al., “Regulated lentiviral packaging cell line devoid of most viral cis-acting sequences,” Virology, Sep. 1998, 249(1):167-174

Lacoste et al., “An Efficient and Reversible Transposable System for Gene Delivery and Lineage-Specific Differentiation in Human Embryonic Stem Cells,” Cell Stem Cell, Sep. 2009, 5(3):332-342.

Loew et al., “A New PG13-Based Packaging Cell Line for Stable Production of Clinical-Grade Self-Inactivating Gamma-Retroviral Vectors Using Targeted Integration,” Gene Therapy, Feb. 2010, 17(2):272-280.

(56) References Cited

OTHER PUBLICATIONS

Mullick et al., "The cumate gene-switch: a system for regulated expression in mammalian cells," BMC Biotechnology, Nov. 2006, 6:43.
Schucht et al., "A new generation of retroviral producer cells: predictable and stable virus production by Flp-mediated site-specific integration of retroviral vectors," Molecular Therapy: the Journal of the American Society of Gene Therapy, May 2006, 14(2):285-292.
Tao et al., "Advance of Tol1 Transposable Element Study," Biotechnology Bulletin, May 2012, 4 pages, (English Abstract).
Yant et al., "Mutational analysis of the N-terminal DNA-binding domain of sleeping beauty transposase: critical residues for DNA binding and hyperactivity in mammalian cells," Molecular and Cellular Biology, Oct. 2004, 24(20):9239-9247.
Yu et al., "Inducible human immunodeficiency virus type 1 packaging cell lines," Journal of Virology, Jul. 1996, 70(7):4530-4537.
Yusa et al., "A hyperactive piggyBac transposase for mammalian applications," Proceedings of the National Academy of Sciences, Jan. 2011, 108(4):1531-1536.
Zhao et al. "Low Temperature Electroporation Combined with Sleeping beauty Transposon System Enhances CAR-T Modification Efficiency," Chinese Journal of Cell Biology, Sep. 2019, 11 pages (English Abstract).
Berg et al., "Rapid establishment of stable retroviral packaging cells and recombinant susceptible target cell lines employing novel transposon vectors derived from Sleeping Beauty," Virology, Feb. 23, 2019, 531:40-47.
Liu et al., "Construction of a doxycycline inducible adipogenic lentiviral expression system.," Plasmid, Jan. 1, 2013, 69(1):96-103.
Office Action in Japanese Appln. No. 2022-564610, mailed Apr. 25, 2024, 9 pages (with English Translation).
Partial Supplementary European Search Report in European Appln. No. 20934080.1, mailed Jul. 4, 2024, 15 pages.
Rad et al., "PiggyBac Transposon Mutagenesis: A Tool for Cancer Gene Discovery in Mice," American Association for the Advancement of Science, Nov. 1, 2010, 333(6007):1104-1107.
Woodard et al., "PiggyBac-ing models and new therapeutic strategies," Trends in Biotechnology, Sep. 1, 2015, 33(9):525-533.
Yamada et al., "Light Control of the Tet Gene Expression System in Mammalian Cells," Cell Reports, Oct. 9, 2018, 25(2):487-500.
Furushima et al., "Insertional Mutagenesis by a Hybrid PiggyBac and Sleeping Beauty Transposon in the Rat," Genetics, Dec 2012, 192:1235-1248.
Search Report and Written Opinion in Singaporean Appln. No. 11202254004W, mailed on Nov. 28, 2025, 14 pages.

* cited by examiner

PRODUCER CELL AND PACKAGING CELL FOR RETROVIRAL VECTOR AND PREPARATION METHOD THEREOF

CROSS-REFERENCE TO RELATED APPLICATIONS

This application is a National Stage application under 35 U.S.C. § 371 of International Application No. PCT/CN2020/115522, filed Sep. 16, 2020, which claims priority to Chinese Application No. 202010366440.4, filed Apr. 30, 2020, both of which are considered part of the disclosure of this application, and are incorporated in their entirety into this application.

SEQUENCE LISTING

This application contains a Sequence Listing that has been submitted electronically as an ASCII text file named 52392-0003US1_ST25.txt. The ASCII text file, created on Aug. 26, 2025, is 53,282 bytes in size. The material in the ASCII text file is hereby incorporated by reference in its entirety.

FIELD

The present disclosure relates to the field of viral vectors, in particular to the field of retroviral vectors, in particular to lentiviral vectors; more particularly, it relates to a method for preparing a retroviral, especially lentiviral vector, and relates to a producer/packaging cell for the preparation of a retroviral, especially a lentiviral vector and to a method for preparing said cell.

BACKGROUND

Retroviruses belong to RNA viruses and are enveloped double-stranded RNA viruses, characterized primarily by their ability to "reverse transcribe" their genome from RNA to DNA. Virions are typically about 100 nm in diameter and contain a dimeric genome (with two identical single positive-stranded RNAs) that forms a complex with a Nucleocapsid (NC) protein. The genome is encapsulated in a protein capsid (CA) which further contains proteins with enzymatic activities, i.e. reverse transcriptase (RT), integrase (IN) and protease (PR), which are essential for viral infection. A matrix protein (MA) forms a layer outside the capsid, wherein the layer interacts with an envelope which is a lipid bilayer derived from the host cell membrane and surrounding the viral core particle. Anchored to the envelope is a viral envelope glycoprotein (Env), which is responsible for recognizing specific receptors on the host cell and initiating the infection process. The envelope protein is formed by two subunits, a transmembrane (TM) subunit anchoring the protein into the lipid membrane and a surface (SU) subunit binding to the cellular receptor, respectively.

Gamma-retroviral vector is the most commonly used retroviral vector, accounting for 17.3% of all the transfection methods used in clinical trial of gene therapy submitted for approval in 2017. Currently, there is increasing interest in lentiviral vectors derived from complex retroviruses such as human immunodeficiency virus (HIV-1), from 2.9% of gene therapy clinical trials in 2012 to 7.3% in 2017. This is because lentiviruses are capable of transducing non-divided cells, which is a property distinguishing them from other virus vectors (including gamma-retrovirus vectors). In addition, lentiviruses have a more favorable lineage of gene insertion site than other retroviruses. The most attractive properties of retroviral and lentiviral vectors are: as a gene delivery tool, the gene delivery capacity can reach 9 kb; less immune reaction in a patient and better clinically proved safety; high transduction efficiency in vivo and in vitro; and the ability to permanently integrate foreign genes into the target cell genome, resulting in long-lasting expression of the delivered genes.

The prototype lentivirus vector system was developed based on the HIV-1 virus, which is a well studied human pathogenic virus. In addition to HIV-1, other lentiviruses have also been developed for use as a gene transfer vector (TV), but most of them have not reached a clinical research stage, such as HIV-2, Simian immunodeficiency virus (SIV), or non-primate lentiviruses, including feline immunodeficiency virus (FIV), bovine immunodeficiency virus (BIV) or goat arthritis-encephalitis virus (CAEV). Only the vector based on equine infectious anemia virus (EIAV) has been developed and reached clinical stage for the treatment of Parkinson's disease (ProSavin).

Mainly due to the safety problem caused by the pathogenicity of HIV-1 in human beings, three generations of lentivirus vector systems are currently being developed. The first generation of lentiviral vector system is represented by a three-plasmid system consisting of 3 plasmids, that is, a packaging plasmid, an envelope plasmid, and a transfer vector plasmid having a viral genome transcriptional cassette carrying a nucleic acid fragment of interest. The packaging plasmid is derived from HIV-1 proviral genome, wherein the 5'LTR thereof is replaced with cytomegalovirus early promoter, the 3' LTR is replaced with simian virus-40 poly A (SV40 polyA) sequence, and the envelope gene env of HIV-1 is deleted. The packaging plasmid expresses rev, vif, vpr, vpu and nef helper genes simultaneously. The deleted HIV-1 envelope gene is replaced with VSV-G (an envelope protein gene of vesicular stomatitis virus), and expressed by the envelope plasmid. The transfer vector plasmid having a viral genome transcriptional cassette carrying a nucleic acid fragment of interest carries a 5' LTR of HIV-1, and an entire 5' untranslated region, a 5' gag gene of about 300 bp, a central polypurine tract (cppt) fragment, as well as a Rev Response Element (RRE) fragment. The transfer vector plasmid is used to clone the nucleic acid fragment of interest and provide viral genomic RNA during viral assembly. The second-generation lentivirus vector system is obtained by modifying the first generation, wherein all the helper genes (vif, vpr, vpu, and nef genes) of HIV-1 are deleted from the packaging plasmid. The removal of these auxiliary genes does not affect the titer and infectivity of the virus, and simultaneously increases the safety of the vector. The third-generation lentivirus vector system consists of four plasmids, which removes the rev gene from the packaging plasmid and places it separately in another packaging plasmid. Furthermore, the third-generation lentiviral vector system has two more safety features: the first safety feature is construction of self-inactivating lentiviral transfer vector plasmid, that is, a U3 region of 3'LTR in the viral genome transcriptional cassette is deleted, so that the lentiviral vector permanently loses the enhancer and promoter fragments of the U3 region of 5' LTR and 3' LTR after completion of the reverse transcription reaction, and so that even if all the viral proteins are present at the time, the virus cannot be successfully packaged because the viral genomic RNA cannot be transcribed. Therefore, the third-generation transfer vector plasmids is also called self-inactivating (SIN) transfer vector plasmids. At the same time, deleting the U3 region also greatly reduces the carcinogenicity of the vector gene inserted into the host cell. The second safety feature is that the tat gene with transcriptional transactivation function is removed, and that the viral genomic RNA is transcribed by replacing the enhancer and promoter sequence of U3 region of 5' LTR with a heterologous promoter sequence, wherein the heterologous promoter cannot be transcribed by itself when transcribing the lentiviral genomic RNA, thus further ensuring that the lentivirus vector can only be packaged and transfected once. The third-generation lentiviral system only retains gag, pol and rev gene sequences of the original HIV-1 genome, and thus the third-generation lentiviral vector system is safer.

Retroviral/lentiviral vectors can have different pseudotypes by replacement with different heterologous envelope glycoproteins, for example, replacement with envelope protein of lentivirus (such as human, ape, feline or bovine immunodeficiency virus, goat arthritis-encephalitis virus, equine infectious anemia virus, etc.), envelope protein of retrovirus (such as murine leukemia virus (10A1, 4070A), gibbon ape leukemia virus, feline leukemia virus (RD114), amphotropic retrovirus, ecotropic retrovirus, baboon ape leukemia virus, etc.), envelope protein of paramyxoviruses (such as measles virus, nipah virus, etc.), envelope protein of rhabdoviruses (such as rabies virus, mokola virus, etc.), envelope protein of filoviruses (such as Ebola Zaire virus, etc.), envelope protein of arenaviruses (such as lymphocytic choriomeningitis virus, etc.), envelope protein of baculovirus, envelope protein of alphaviruses (such as chikungunya virus, Ross River virus, Semliki Forest virus, Sindbis virus, Venezuelan equine encephalitis virus, Western equine encephalitis virus, etc.), envelope protein of Orthomyxoviruses (such as Influenza virus and Fowl plague virus, etc.), envelope protein of Vesiculoviruses (such as Vesicular stomatitis virus, Chandipura virus and Piry virus, etc.). Most lentiviral vectors are currently prepared by using the vesicular stomatitis virus envelope glycoprotein (VSV-G), since this glycoprotein makes the lentiviral vector have a wide range of transduction spectrum and a better stability during downstream processing.

Currently most retroviral/lentiviral vectors are preferably prepared using mammalian cell lines as host cells, wherein the most widely used are 293T or HEK293 cell lines as well as derived cell lines screened or engineered therefrom. HEK293 cell line is a human renal epithelial cell line transfected with adenovirus E1A gene; 293T cell is derived from HEK293 cell and expresses SV40 large T antigen, and a plasmid containing an SV40 replication initiation site and a promoter region can be replicated in 293T cell and maintain a high copy number in a period, so that the protein expression of the gene carried by the plasmid is increased. Furthermore, compared with HEK293 cell, 293T cell has a faster cell growth rate and higher transfection efficiency. The above features of 293T cell bring about a higher efficiency for preparing virus vectors. In addition, according to literature reports, the production/packaging cells for viral vectors also include mammalian cells HepG2 cells, CHO cells, BHK cells, COS cells, NIH/3T3 cells, Vero cells, HT1080 cells, Te671 cells, CEM cells, NSO cells and PerC6 cells.

At present, a method for preparing a retroviral/lentiviral vector generally involves respectively introducing a gag gene, a pol gene, a rev gene (for lentiviral vector), an envelope glycoprotein gene, and a viral genome transcriptional cassette carrying a nucleic acid fragment of interest (comprising a promoter for transcribing and packaging into the retrovirus/lentivirus RNA genome; various cis-acting sequences required for the packaging and transfection of retroviral/lentiviral genome, such as 5' LTR, PBS, Ψ packaging signal, cppt (for lentiviral vector), RRE (for lentiviral vector), ppt and 3' LTR sequence, etc.; a nucleic acid fragment of interest to be transduced, 3' polyA signal, etc.) into a mammalian host cell, usually a murine or human cell. This can be achieved by transient transfection of the above construct (such as a plasmid) containing the above gene into a host cell and then producing viral vectors for 24-72 hours and harvesting them (transient production), or by stable integration of the above gene into a host cell genome to form a stable producer cell line for continuous production (stable production).

In transient production, the viral gene construct is introduced by a transfection plasmid, wherein a cationic reagent that can form a complex with negatively charged DNA is used, allowing it to be taken up by a cell via endocytosis. Polyethyleneimine (PEI) is one of the most widely used and most efficient cationic reagents. At present, the method of PEI transfection is mostly used for introducing the above construct clinically and industrially, but the main problem of such a method is unstability, low titer and the like after process amplification. Other methods, such as calcium phosphate precipitation, cationic liposome complexation, and non-liposome transfection reagents, such as Lipofectamine and FuGENE®, may also be used. However, these methods can only be used for small-scale production or only for research purposes, as they are either difficult to scale up or too expensive. Alternatively, viral infection has also been developed and validated for producing retroviral/lentiviral vector, which uses baculovirus or adenovirus to introduce lentiviral gene constructs. However, this method requires additional downstream isolation of retroviral/lentiviral vector and baculovirus or adenovirus to meet clinical-grade standard for virus production, and the process of preparing retroviral/lentiviral vectors by using baculovirus or adenovirus is complicated and the final transfection titer is not high compared to the method of plasmid DNA transfection. Alternatively, a technique of continuous electroporation has also been developed for large-volume cell transfection. In principle, it can also be used for transient transfection of retroviruses/lentiviruses, but this technique is still limited by the scale-up capability and expensive equipment and consumables.

Construction of stable retroviral/lentiviral producer cell lines relies on the integration of viral gene constructs into the cell genome to allow constitutive or regulated expression. Usually, gag, pol, rev (for lentiviral vectors) and env genes are firstly introduced into cells simultaneously or sequentially and then cells in which the above genes are stably inserted into the genome and highly expressed are selected by corresponding resistance screening and clonal selection, thus packaging cell lines are established. Thereafter, a viral genome transcriptional cassette carrying a nucleic acid fragment of interest is introduced to construct a viral vector-producer cell line carrying the nucleic acid fragment of interest. This can be achieved directly by viral infection if non-SIN (self-inactivating) vectors that can replicate after reverse transcription are used; otherwise, in order to obtain a producer cell line in which a viral genome transcriptional cassette carrying the nucleic acid fragment of interest is stably integrated into the genome of packaging cells, it is necessary to perform plasmid chemical transfection followed by resistance screening and clonal selection. An efficient method for quickly constructing a producer cell line which stably produces a virus vector carrying a nucleic acid fragment of interest comprises the following steps: inserting the lentiviral genome transcriptional cassette containing a (selectable) marker gene into an original cell, and selecting the producer cell line in which the virus vector is stably integrated and expressed at a high level and for a long term via the marker gene, and then replacing the marker gene used for constructing the above producer cell line with a nucleic acid fragment of interest by site-specific recombinase, such as FLP-FRT or Cre-lox recombinase system. This method was demonstrated to allow establishing a producer cell line of human-derived retroviral vector with a high-titer (Schucht, R., et al. (2006). "A new generation of retroviral producer cells: predictable and stable virus production by Flp-mediated site-specific integration of retroviral vectors." *Mol Ther* 14(2): 285-292; Loew, R., et al. (2010). "A new PG13-based packaging cell line for stable production of clinical-grade self-inactivating gamma-retroviral vectors using targeted integration." *Gene Ther* 17(2): 272-280). In addition, a platform of viral vector packaging cell line or producer cell line for rapid replacement of nucleic acid fragments of interest and/or envelope proteins can be developed by using similar principles. Development of stable producer cell lines of retroviral/lentiviral vector is a time-consuming and labor-intensive complex system engineer, which requires one year or more to fully develop and characterize the cell line platform, and due to the complexity of the work, many of the published work has ultimately failed to meet industrial needs due to issues such as titer, stability of cell lines, culture adaptation, etc. However, as a compensation, once a stable virus producer cell line is successfully developed and obtained, the stable virus producer cell line has irreplaceable advantages in the aspects of process reliability, process scale-up capacity, production cost, safety of virus product and the like in the fields of clinical and industrial applications compared with a production process of transient transfection. Firstly, the production process of stable producer cell line is more stable, and can provide a fully characterized production platform to produce safer viral vectors with low batch-to-batch differences; secondly, the process is easier to be scaled up, and will not lead to a rapid reduction of production titer along with the increase of culture volume, as occurs in a transient production system; in addition, because no raw materials or auxiliary materials such as DNA plasmids and transfection reagents are needed, there is no need to establish an additional GMP production line for plasmid production; finally, the process has higher unit yield and simpler quality control for production process. When expanding the production scale, a production process based on the stable producer cell line will further highlight its advantages in aspects of research and development, production, management, operation and maintenance, costs and the like. These advantages are beneficial for facilitating the technical and pharmaceutical industrialization in the fields of gene therapy and cell therapy.

The use of stable producer cell lines to produce retroviral vectors has been in the scientific research and clinical trials for over a decade. However, the establishment of a stable packaging cell line and producer cell line of lentiviral vector remains challenging, since many HIV-1 encoded proteins, including rev, tat, nef, env, vpr, and PR proteases, are cytotoxic and can lead to cell death, among which rev and PR proteases are still necessary in current packaging systems, and the pseudotyped envelope protein VSV-G commonly used in lentiviral systems is also highly cytotoxic. At the laboratory level, transient production by plasmid transfection is a common solution to avoid cytotoxic proteins from affecting virus production. However, in the development of a stable producer cell line of lentivirus, the expression of the above-mentioned cytotoxic protein must be strictly controlled, for example, by using an inducible expression system, otherwise all high-expressing cell lines will die and it is difficult to form a stable producer cell line.

The titer of retroviral/lentiviral vector in the pre-purified cell stock currently available is from $10^6$ to $10^7$ infectious particles/mL medium. However, the average amount of vector required to treat a patient in clinical trial is at the level of $10^{10}$ infectious particles per patient. In addition, virus production is generally characterized by a low infectious particle/physical particle ratio (less than 1:100); at the same time, these virus vectors are very sensitive and will lose their infectivity rapidly in cell culture supernatants at 37° C. with a half-life of about 8-12 hours, which further increases the demand for virus productivity. It is estimated that each patient requires approximately 10-100L of culture volume to produce viral vectors based on the existing transient transfection platform, and the existing production technology is difficult to be substantially improved both in titer and process scale-up. Therefore, the performance of the current production system of retroviral/lentiviral vector is far below therapeutic requirements, and the key to solve the problem of productivity is to construct a more productive stable producer cell line and to achieve the large-scale production process.

However, it is quite technically difficult to construct a stable producer cell line of retroviral/lentiviral vectors. The existing method for constructing a stable producer cell line usually requires the introduction of a large number of resistance genes for simultaneous or stepwise screening due to the low efficiency of stable gene insertion. Many screening processes are carried out under serum-containing adherent culture conditions, and the screened cell line may not be adapted to the suspension culture condition of serum-free medium, and thus does not meet the technical development trend and safety requirements of the international biopharmaceutical industry. In addition, during the construction of the producer cell line, due to insufficient regulation and expression optimization of each reverse transcription/lentiviral packaging gene, the final stable cell line or the virus titer is not high or there is a high leaky expression, and the high leaky expression will lead to an unstable producer cell line and that the cell growth quality is affected by the cytotoxicity caused by the leaky expression of the packaging gene during cell culture expansion, and thus it is difficult to meet the requirement of process scale-up.

Thus, there is an urgent need in the art for an efficient method for constructing a stable retroviral and lentiviral vector producer cell line, and a viral packaging/producer cell line constructed based on this method.

SUMMARY

The disclosure solves the problems by stably inserting gag, pol and rev (used for lentiviral vectors) required by virus packaging into the genome of a host cell (such as 293T cell) through a Sleeping Beauty (SB) transposon system combined with a PiggyBac (PB) transposon system, and then developing an inducible and controllable virus producer system in combination with an inducible expression system (such as a Tet-On system and/or a Cumate system).

When using a retrovirus/lentiviral vector for transduction, the nucleic acid fragment of interest needs to be loaded into the RNA genome packaged into the retrovirus/lentivirus. The term "nucleic acid fragment of interest" may generally refer to a gene, such as a nucleic acid sequence encoding a protein; it may be a functional ribonucleic acid (RNA), such as a small interfering RNA (siRNA), a long non-coding RNA (LncRNA), a guide RNA (gRNA) of the CRISPR gene editing system, a transfer RNA (tRNA), a Ribosomal RNA (rRNA) or other coding sequences of functional RNAs; it may be other functional nucleic acid sequences, such as homologous recombination sequences, DNA or RNA sequences capable of binding to proteins, DNA or RNA sequences capable of binding to other nucleic acid fragments (e.g., primers or probes); it may be any natural nucleic acid sequence or artificial nucleic acid sequence; it may also be a combination of one or more of the above nucleic acid sequences; the nucleic acid fragment of interest may also contain nucleic acid sequences for regulating gene expression, such as a promoter, an enhancer, an insulator, a polyA signal, etc. The RNA genome of a retrovirus and/or lentivirus refers to a ribonucleic acid fragment that can be packaged into a virus when constructing a retroviral/lentiviral vector, and generally comprises sequences necessary for virus packaging and transduction, such as a ψ packaging signal, a Long Terminal Repeat (LTR). The RNA genome of lentivirus generally contains all 5'-untranslated regions, about 300 bp of 5'-gag gene, a central polypurine tract (cppt) fragment, and also contains a Rev Response Element (RRE) fragment; the absence of one or more of these fragments may severely affect the packaging or transduction efficiency of the lentivirus. In the preparation of retroviral/lentiviral vectors, the RNA fragment of viral genome carrying the nucleic acid fragment of interest is typically obtained by constructing a viral genome transcriptional cassette carrying the nucleic acid fragment of interest, wherein the transcriptional cassette comprises a nucleic acid sequence with a promoter function (which may be a retroviral/lentiviral LTR sequence or other heterologous promoters), a DNA sequence corresponding to the RNA genome of the virus, and typically comprises a polyA signal sequence that regulates the termination of transcription. In the preparation of retrovirus/lentivirus vectors, a construct with the viral genome transcriptional cassette carrying a nucleic acid fragment of interest (e.g., the transcriptional cassette is constructed into a transfer vector plasmid) is delivered into a host cell; and then through the transcriptional molecular mechanism of the host cell, it is transcribed into a corresponding viral genome RNA fragment that can be packaged into the viral vector and carries the nucleic acid fragment of interest.

In the present disclosure, the retrovirus includes, but is not limited to, lentiviruses such as Murine Leukemia Virus (MLV), Human Immunodeficiency Virus (HIV), Equine Infectious Anemia Virus (EIAV), Mouse Mammary Tumor Virus (MMTV), Rous Sarcoma Virus (RSV), Fujinami sarcoma virus (FuSV), Moloney murine leukemia virus (Mo-MLV), FBR murine sarcoma virus (FBR MSV), Moloney murine sarcoma virus (Mo-MSV), Abelson murine leukemia virus (A-MLV), avian myelomatosis virus-29 (MC29), and Avian Encephalomyelitis Virus (AEV), Simian immunodeficiency virus (SIV), Feline immunodeficiency virus (FIV), Bovine immunodeficiency virus (BIV), Caprine arthritis-encephalitis virus (CAEV), Gibbon ape leukemia virus, Feline leukemia virus, Amphotropic retrovirus, Ecotropic retrovirus, Baboon ape leukemia virus, and all other viruses of retroviridae.

Transposon refers to a DNA sequence that can change its position within the genome. The transposon can produce or reverse mutations and alter the size of the cell genome. DNA transposons can be translocated from one DNA site to another in a simple cut-and-paste manner by the action of expressed transposase. Transposition is an accurate process in which the defined DNA fragments, usually Direct Repeats (DR) at both ends of a transposon and Invert Repeats (IR) linked to them, as well as Insert Sequences (IS), are cut out from one DNA molecule and moved to another site in the same or a different DNA molecule or genome.

The "Sleeping Beauty (SB) transposon system" consists of an SB transposase and a transposon, which are capable of inserting specific DNA insertion sequences into the genome of vertebrates. SB transposase can insert the transposon into a TA dinucleotide base pair in the receptor DNA sequence. The insertion site can be located in another position of the same DNA molecule (or chromosome) or in another DNA molecule (or chromosome). There are approximately 200 million TA sites in the mammalian (including human) genome. The TA insertion site is replicated during transposon integration. This replication of the TA sequence is a marker of transposition and is used to determine the mechanism in some experiments. The SB transposon consists of an insertion sequence of interest and an IR/DR sequence (itself containing short direct repeats (DR) and inverted repeats (IR), for example, as shown in SEQ ID NO: 23 or its complementary sequence) which is located at both ends for recognition by an SB transposase. The transposase can be encoded within the transposon, or the transposase can be provided by another source. Wild-type and different variants of transposase, IR/DR sequences and transposons in the SB transposon system are known in the art. The published plasmids containing Sleeping Beauty transposon include: pT/HB (Addgene, #26555), pT2/HB (Addgene, #26557), pT3 (Yant, S. R., et al. (2004). "Mutational analysis of the N-terminal DNA-binding domain of sleeping beauty transposase: critical residues for DNA binding and hyperactivity in mammalian cells." Mol Cell Biol 24(20): 9239-9247) and the like. Variants of SB transposase include, but are not limited to, SB10, SB11, SB100X (the coding sequence is shown in SEQ ID NO: 30), and the like (see, e.g., WO9840510A1, WO2003089618A2, WO2009003671A2, WO2017046259A1, WO2017158029A1, etc., which are incorporated herein by reference). As used herein, the term "Sleeping Beauty (SB) transposon system" may include an SB transposon system containing wild-type and different variants of SB transposase and wild-type and different variants of SB transposon.

The "PiggyBac (PB) transposon system" derived from *Trichoplusia ni* is composed of a PB transposase and a transposon, and it can be transposed efficiently between vectors and chromosomes through a cut-and-paste mechanism. In the process of transposition, PB transposase recognizes the transposon-specific inverted terminal repeat (referred to as ITR for short, wherein, 3'ITR is such as the sequence of SEQ ID NO: 24 or its complement sequence, and 5'ITR is such as the sequence of SEQ ID NO: 25 or its complementary sequence) located at both ends of the transposon vector, and effectively moves the inserted sequence between the 5'ITR and 3'ITR from the original site and effectively integrates it into the TTAA site of the chromosome. The powerful activity of the PiggyBac transposon system allows the insertion sequence of interest between two ITRs in the PB transposon vector to be easily moved into the target genome. Wild-type and different variants (e.g., ePiggyBac, with the coding sequence as set forth in SEQ ID NO: 31) of transposases and transposons in the PB transposon system are known in the art. Information about the PiggyBac transposon system can be found, for example, in patent documents such as U.S. Pat. Nos. 6,218,185B1, 6,551,825B1, 7,105,343B1, US2002173634A1, US2010240133A1, WO2006122442, WO2010085699, WO2010099296, WO2010099301, WO2012074758, U.S. Pat. No. 8,592,211, etc., and non-patent documents such as Lacoste, A., et al. (2009). "An efficient and reversible transposable system for gene delivery and lineage-specific differentiation in human embryonic stem cells." Cell Stem Cell 5(3): 332-342; Yusa, K., et al. (2011). "A hyperactive piggyBac transposase for mammalian applications." Proc Natl Acad Sci USA 108(4): 1531-1536 (the above documents are hereby incorporated by reference). As used herein, the term "Piggybac (PB) transposon system" can include a PB transposon system containing wild-type and different variants of PB transposase and wild-type and different variants of PB transposon.

In the present disclosure, the inducible expression system is used to control the transcription and expression of related genes in the nucleic acid construct introduced into the host cell. Examples of inducible expression systems that may be used in the present disclosure include, but are not limited to, a Tet-off inducible expression system in tetracycline inducible system (see, e.g., Gossen, M. and H. Bujard (1992). "Tight control of gene expression in mammalian cells by tetracycline-responsive promoters." Proc Natl Acad Sci USA 89(12): 5547-5551; Yu, H., et al. (1996). "Inducible human immunodeficiency virus type 1 packaging cell lines." J Virol 70(7): 4530-4537; Kaul, M., et al. (1998). "Regulated lentiviral packaging cell line devoid of most viral cis-acting sequences." Virology 249(1): 167-174 (which are incorporated by reference)), a Tet-On inducible expression system in tetracycline inducible system (see, e.g., WO0075347A2, WO2007058527A2 (which are incorporated by reference), a Cumate system (see, e.g., WO02088346A2, WO2006037215A1 (which are incorporated by reference), a Cumate inducible expression system (see, Mullick, A., et al. (2006). "The cumate gene-switch: a system for regulated expression in mammalian cells." BMC Biotechnol 6: 43; WO02088346A2, WO2006037215A1 (which are incorporated by reference)), or a combination thereof. In one aspect, the inducible expression system for inducible expression is a Tet-On inducible expression system or a Cumate inducible expression system. In another aspect, the inducible expression system for inducible expression is a combination of the Tet-On inducible expression system and the Cumate inducible expression system. In the Tet-On inducible expression system, only in the presence of tetracycline or tetracycline derivatives such as doxycycline (Dox), a reverse tetracycline controlled transactivator (rtTA) can bind to a TRE response element (a nucleic acid sequence containing multiple copies of a contiguous TetO operator sequence and a minimal promoter sequence, hereinafter referred to as a TRE) of Tet-On inducible expression system to initiate the transcription of a regulated nucleic acid fragment linked downstream. The currently used Tet-On inducible expression systems include the second-generation Tet-On inducible expression system (Tet-On Advanced, Clontech, wherein the transactivator rtTA and the Tet responsive element (TRE) are hereinafter referred to as $rtTA_{adv}$ (encoding nucleic acid sequence: SEQ ID NO: 29) and $TRE_{adv}$ (SEQ ID NO: 21), respectively), and the third-generation Tet-On inducible expression system (Tet-On 3G, Clontech, wherein the transactivator rtTA and the Tet responsive element (TRE) are hereinafter referred to as $rtTA_{3G}$ (encoding nucleic acid sequence: SEQ ID NO: 28) and $TRE_{3G}$ (SEQ ID NO: 19), respectively). The transactivator rtTA and TRE in the second-generation and third-generation Tet-On inducible expression systems can be used in combination, for example, $rtTA_{adv}$ can be used in combination with $TRE_{3G}$, and $rtTA_{3G}$ can also be used in combination with $TRE_{adv}$. Cumate inducible expression system is developed from *Pseudomonas putida*'s p-cym operon, and it consists of a CuO operator downstream of a TATA box of a promoter and a suppressor CymR protein which can bind to the CuO operator depending on Cumate and derivatives thereof. In the absence of Cumate, the CymR protein binds to the CuO operator to inhibit the transcription and expression of the nucleic acid sequence of interest linked downstream; when the CymR protein binds to Cumate, the affinity of the CymR protein to the CuO operator is reduced, and the CymR protein and the CuO operator are separated, so that the transcription and expression of the nucleic acid sequence of interest linked downstream are not inhibited. In the present disclosure, when the Tet-On inducible expression system is used in combination with the Cumate inducible expression system, a complex response element sequence is constructed, which contains multi-copy continuous TetO operator sequences, a minimal promoter sequence containing a TATA box and a CuO operator sequence. Wherein, a $TRE_{adv}$CuO (SEQ ID NO: 22) complex response element is designed based on the multi-copy continuous TetO operator sequences in the $TRE_{adv}$ sequence of the second-generation Tet-On inducible expression system; a $TRE_{3G}$CuO complex response element (SEQ ID NO: 20) is designed based on the multi-copy continuous TetO operator sequences in the $TRE_{3G}$ sequence of the third-generation Tet-On inducible expression system. When the Tet-On inducible expression system is used in combination with the Cumate inducible expression system, a transactivator rtTA protein of the Tet-On inducible expression system and a repressor CymR protein of the Cumate inducible expression system need to be simultaneously expressed, wherein the Tet-On transactivator used can be $rtTA_{adv}$ or $rtTA_{3G}$. Preferably, $rtTA_{3G}$ (SEQ ID NO: 28) and CymR (SEQ ID NO: 27) sequences optimized based on human coding codons are used. In one aspect, the inducible expression system that can be used for the purpose of the present disclosure may also include metal ion inducible, hormone inducible and temperature inducible expression systems.

In one aspect of the present disclosure, the transcription of one or more of gag and pol genes (gag/pol in the Examples representing that gag and pol genes are located in the same construct and expressed by frameshift), the rev gene, the coding sequence of the viral envelope protein (e.g., VSV-G) and the viral genome transcription cassette carrying a nucleic acid fragment of interest is under control by placing the genes or sequences under the control of an inducible expression system, preferably by placing the genes or sequences under the control of a Tet-On and/or Cumate inducible expression system, more preferably under the dual control of the Tet-On inducible expression system and the Cumate inducible expression system or under the single control of the third-generation Tet-On inducible expression system. In one aspect of the present disclosure, all the transcription of gag and pol genes, the rev gene, the coding sequence of the viral envelope protein and the viral genome transcription cassette carrying a nucleic acid fragment of interest is controlled by placing the genes or sequences under the control of an inducible expression system, preferably by placing the genes or sequences under the control of a Tet-On and/or Cumate inducible expression system, more preferably under the dual control of the Tet-On inducible expression system and the Cumate inducible expression system or under the single control of the third-generation Tet-On inducible expression system. In one aspect of the present disclosure, among gag and pol genes, the rev gene, the coding sequence of the viral envelope protein (VSV-G) and the viral genome transcription cassette carrying a nucleic acid fragment of interest, the transcription of the rev gene and the coding sequence of the viral envelope protein (VSV-G) is under control by placing the gene or the sequence under the control of an inducible expression system, preferably by placing the gene or the sequence under the control of a Tet-On and/or Cumate inducible expression system, more preferably under the dual control of the Tet-On inducible expression system and the Cumate inducible expression system or under the single control of the third-generation Tet-On inducible expression system.

The expression level of the regulated nucleic acid fragment under induction condition and the leaky expression level under non-induction condition are two important indicators for evaluating the quality of an inducible expression system. A good inducible expression system needs to have a higher induction expression and a lower leaky expression. The inventor finds that the induction expression level and leaky expression level of the Tet-On inducible expression system alone or the Tet-On and Cumate complex inducible expression system are affected by the following factors: (1) the minimal promoter sequence in the TRE response element; (2) selection of mutants of rtTA transactivator; (3) whether a spliceable intron sequence is linked between the 3' end of the response element of inducible system and the 5' end of the nucleic acid sequence of interest to be regulated. The present disclosure designs and uses four response elements ($TRE_{adv}$, $TRE_{3G}$, $TRE_{adv}$CuO and $TRE_{3G}$CuO) and two transactivators ($rtTA_{adv}$ and $rtTA_{3G}$). The control of the third-generation $TRE_{3G}$ response element is more stringent than that of the second-generation $TRE_{adv}$ response element, and the regulated nucleic acid fragment has a lower leaky expression level, but a lower induction expression level as compared to $TRE_{adv}$. The control of the Tet-On and Cumate complex inducible expression system response elements of the present disclosure, $TRE_{adv}$CuO (SEQ ID NO: 22) and $TRE_{3G}$CuO (SEQ ID NO: 20), is more stringent than that of any response element in a single Tet-On inducible system, so that the leaky expression level of the regulated nucleic acid fragment is significantly reduced, and the induction expression level of the regulated nucleic acid fragment is also significantly reduced. Compared with $rtTA_{adv}$, the transactivator $rtTA_{3G}$ has similar transcriptional activation activity under induction conditions, while, under non-induction conditions, the basic leaky transcription activation activity of $rtTA_{3G}$ is lower. The intron linked to the 3' end of the promoter in the expression plasmid can generally increase the stability of messenger RNA (mRNA) and increase the efficiency of transport of the mRNA out of the nucleus (see Akef, A., et al. (2015). "Splicing promotes the nuclear export of beta-globin mRNA by overcoming nuclear retention elements." RNA 21(11): 1908-1920) and increase the expression of the regulated nucleic acid fragment. The present inventor has found that linking a spliceable intron between the 3' end of the response element and the 5' end of the regulated nucleic acid fragment in a single inducible expression system can increase the induction expression of the regulated nucleic acid fragment, but also significantly increase the leaky expression of the regulated nucleic acid fragment. In the Tet-On and Cumate complex inducible system of the present disclosure, inserting a spliceable intron sequence between the 3' end of the response element and the 5' end of the regulated nucleic acid fragment can significantly increase the induction expression under inducible conditions without significantly increasing the leaky expression under non-inducible conditions.

When constructing a lentivirus producer cell line, it is necessary to balance the expression levels, the relative ratio of the expression levels, the cytotoxicity of the expressed protein or the transcribed nucleic acid, and the sequence of expression or transcription of the rev gene, the VSV-G gene, gag and pol genes and the viral genome transcription cassette carrying a nucleic acid fragment of interest, and thus it is necessary to optimize the promoter or inducible expression system response element for each gene and the viral genome transcriptional cassette carrying a nucleic acid fragment of interest. Among the lentiviral rev gene, VSV-G gene, gag and pol genes to be expressed and the viral genome transcription cassette carrying a nucleic acid fragment of interest, the rev and the membrane protein VSV-G are significantly cytotoxic, and the rev also regulates the expression of gag and pol genes which generally contain RRE sequence, so the strict control with an inducible expression system is required. The expression of gag and pol genes does not have to be strictly regulated under the condition of rev being controlled, but controlling the expression of gag and pol genes with an inducible expression system may further reduce viral titers of leaky expression under non-inducible conditions, especially where the expression of rev and VSV-G is under control by a single Tet-On inducible expression system. In view of the above, based on 4 response elements and presence or absence of a spliceable intron sequence between the 3' end of the response element and the 5' end of the regulated nucleic acid fragment, 8 regulatory sequences for lentiviral gene expression are designed and tested in the present disclosure: $TRE_{adv}$ (wherein, the inducible system response element is a $TRE_{adv}$ sequence (SEQ ID NO: 21) and there is no intron between the 3' end of the response element and the 5' end of the regulated nucleic acid fragment), $TRE_{adv}$CuO (wherein, the inducible system response element is a $TRE_{adv}$CuO sequence (SEQ ID NO: 22) and there is no intron between the 3' end of the response element and the 5' end of the regulated nucleic acid fragment), $TRE_{3G}$ (wherein, the inducible system response element is a $TRE_{3G}$ sequence (SEQ ID NO: 19) and there is no intron between the 3' end of the response element and the 5' end of the regulated nucleic acid fragment), $TRE_{3G}$CuO (wherein, the inducible system response element is a $TRE_{3G}$CuO sequence (SEQ ID NO: 20) and there is no intron between the 3' end of the response element and the 5' end of the regulated nucleic acid fragment), $TRE_{adv}$-intron (wherein, the inducible system response element is a $TRE_{adv}$ sequence and a spliceable intron is linked between the 3' end of the response element and the 5' end of the regulated nucleic acid fragment), $TRE_{adv}$-CuO-intron (wherein, the inducible system response element is a $TRE_{adv}$CuO sequence, and a spliceable intron is linked between the 3' end of the response element and the 5' end of the regulated nucleic acid fragment), $TRE_{3G}$-intron (wherein, the inducible system response element is a $TRE_{3G}$ sequence, and a spliceable intron is linked between the 3' end of the response element and the 5' end of the regulated nucleic acid fragment), and $TRE_{3G}$CuO-intron (wherein, the inducible system response element is a $TRE_{3G}$CuO sequence, and a spliceable intron is linked between the 3' end of the response element and the 5' end of the regulated nucleic acid fragment), to optimize the optimal combination for regulating the expression of each gene of the lentivirus. In the present disclosure, the intron between the 3' end of the response element and the 5' end of the regulated nucleic acid fragment controlled by the response element may or may not be directly linked to the response element and the regulated nucleic acid fragment controlled by the response element, which can be adjusted by those skilled in the art according to the disclosure as required; in the case of not being directly linked, those skilled in the art will understand that the distance between the response element and the regulated nucleic acid fragment controlled by the response element should not affect the control of transcription of the regulated nucleic acid fragment by the response element. In one aspect of the present disclosure, in the case of a single Tet-On inducible regulatory system, the regulatory sequence of rev is preferably $TRE_{3G}$; the regulatory sequence of VSV-G is preferably $TRE_{3G}$-intron; the regulatory sequence of gag and pol is preferably CMV promoter (or other eukaryotic promoter commonly used in the art)-intron or $TRE_{3G}$-intron, and more preferably $TRE_{3G}$-intron; rtTA transactivator is preferably $rtTA_{3G}$. Under the above conditions, transient transfection of the related plasmids can reach 6.94E+05 RLU and 176 times of induction/leaky virus-producing titer ratio; compared with the second-generation Tet-On system (4.64E+05 RLU, 7 times of induction/leaky titer ratio), the virus-producing titer is improved by 49.6%, and the control of virus leaky expression is improved by 25 times. In one aspect of the present disclosure, in the case of the Tet-On and Cumate complex inducible regulation system, the regulatory sequence of rev is preferably $TRE_{adv}$CuO, $TRE_{adv}$CuO-intron, $TRE_{3G}$, $TRE_{3G}$CuO or $TRE_{3G}$CuO-intron, more preferably $TRE_{3G}$, $TRE_{3G}$CuO or $TRE_{3G}$CuO-intron, and still more preferably $TRE_{3G}$; the regulatory sequence of VSV-G is preferably $TRE_{adv}$CuO, $TRE_{adv}$CuO-intron, $TRE_{3G}$-intron or $TRE_{3G}$CuO-intron, more preferably $TRE_{adv}$CuO-intron, $TRE_{3G}$-intron or $TRE_{3G}$CuO-intron, and still more preferably $TRE_{3G}$CuO-intron; the regulatory sequence of gag and pol is preferably an intron-containing regulatory sequence, including CMV promoter (or other eukaryotic promoters commonly used in the art)-intron, $TRE_{adv}$-intron, $TRE_{adv}$-CuO-intron, $TRE_{3G}$-intron, or $TRE_{3G}$CuO-intron, more preferably $TRE_{3G}$CuO-intron; the rtTA transactivator is preferably $rtTA_{3G}$. Under the above conditions, transient transfection of the related plasmids can reach 1.46E+06 RLU and 12032 times of induction/leaky virus-producing titer ratio; compared with the second-generation Tet-On system (4.64E+05 RLU, 7 times of induction/leaky virus-producing titer ratio), the titer is improved by 214.7%, and the control of virus leaky expression is improved by 1719 times.

There is no specific limitation on the selection of the above-mentioned spliceable intron sequence linked between the 3' end of the response element and the 5' end of the regulated nucleic acid fragment, and those skilled in the art will understand that any sequence capable of performing RNA splicing in mammalian cells can achieve the above functions. Intron sequences that may be selected include, but are not limited to, introns in common cloning vectors, such as a rabbit β-globulin intron, a hybrid intron derived from human β-globulin and immunoglobulin heavy chain intron, EF-1 α intron A, SV40 intron, a hybrid intron derived from adenovirus and immunoglobulin heavy chain intron, a modified human cytomegalovirus intron, a hybrid intron derived from chicken β-actin (CBA) and mouse microvirus (MMV) intron, a chimera derived from chicken β-actin and rabbit β-globulin intron, and a mP1 intron; or any intron of any gene of any eukaryote; or an artificial intron sequence designed based on the intron splicing rules. The intron sequence used in the examples of the present disclosure may be, for example, the human β-globulin intron sequence (BGI sequence) as set forth in SEQ ID NO: 26.

In the present disclosure, gag and pol genes, the rev gene, the coding sequence of the viral envelope protein (VSV-G) and the viral genome transcription cassette carrying a nucleic acid fragment of interest are stably integrated into the host cell genome by using a transposon system(s). In one aspect of the present disclosure, when one or more of gag and pol genes, the rev gene, the coding sequence of the viral envelope protein (VSV-G) and/or the viral genome transcription cassette carrying a nucleic acid fragment of interest are under the control of a Tet-On and/or Cumate inducible expression system, gag and pol genes, the rev gene, the coding sequence of the viral envelope protein (VSV-G), and the viral genome transcription cassette carrying a nucleic acid fragment of interest, as well as the coding sequence of Tet-On transactivator rtTA protein and/or the coding sequence of repressor CymR protein of the Cumate operon, are integrated into the host cell genome by using a transposon system(s). In one aspect of the disclosure, gag and pol genes, the rev gene, the coding sequence of the viral envelope protein (VSV-G), the viral genome transcription cassette carrying a nucleic acid fragment of interest, and the coding sequence of activator or repressor protein of an inducible expression system (for example, the coding sequence of Tet-On transactivator protein and/or the coding sequence of repressor CymR protein of the Cumate operon) are all integrated into the host cell genome at one step by using SB transposon system or PB transposon system, to directly construct a producer cell line for producing lentivirus. In one aspect of the disclosure, the genes and sequences described above are introduced into host cells by using both SB and PB transposon systems. In a preferred aspect of the disclosure, gag and pol genes, the rev gene, the coding sequence of the viral envelope protein (VSV-G) and the viral genome transcription cassette carrying a nucleic acid fragment of interest (and, in the case of using a Tet-On and/or Cumate inducible expression system, the coding sequence of Tet-On transactivator protein and/or the coding sequence of repressor CymR protein of the Cumate operon) are integrated into the host cell genome in two separate steps. In the first step, one or more of gag and pol genes, the rev gene, the coding sequence of the viral envelope protein (VSV-G) and the viral genome transcription cassette carrying a nucleic acid fragment of interest (and, in the case of using a Tet-On and/or Cumate inducible expression system, the coding sequence of Tet-On transactivator protein and/or the coding sequence of repressor CymR protein of the Cumate operon) are integrated into the host cell genome by using any one of the SB transposon system and the PB transposon system to construct a packaging cell line; and, in the second step, the remaining one or more of gag and pol genes, the rev gene, the coding sequence of the viral envelope protein (VSV-G) and the viral genome transcription cassette carrying a nucleic acid fragment of interest (and, in the case of using a Tet-On and/or Cumate inducible expression system, the coding sequence of Tet-On transactivator protein and/or the coding sequence of repressor CymR protein of the Cumate operon) are integrated into the genome of the above packaging cell line by using the other unused transposon system of the SB and PB transposon system, to construct a producer cell line. In a preferred aspect of the disclosure, firstly, gag and pol genes, the rev gene, the coding sequence of the viral envelope protein (VSV-G) (preferably, and the coding sequences of the activator and/or repressor proteins of the inducible expression system, for example, in the case of using a Tet-On and/or Cumate inducible expression system, the coding sequence of Tet-On transactivator protein and/or the coding sequence of repressor CymR protein of the Cumate operon) are integrated into the host cell genome by using any one of the SB transposon system and the PB transposon system, to construct a packaging cell line; and, secondly, the viral genome transcription cassette carrying a nucleic acid fragment of interest is integrated into the genome of the above packaging cell line which is already integrated with gag and pol genes, the rev gene, the coding sequence of the viral envelope protein (VSV-G) (preferably, and the coding sequences of the activator and/or repressor proteins of the inducible expression system, for example, in the case of using a Tet-On and/or Cumate inducible expression system, the coding sequence of Tet-On transactivator protein and/or the coding sequence of repressor CymR protein of the Cumate operon) in its genome by using the other unused transposon system of the SB and PB transposon system, to construct a producer cell line. In this case, a lentiviral vector producer cell line for preparing a lentiviral vector carrying a nucleic acid fragment of interest can be constructed by the following steps: introducing a construct of the viral genome transcription cassette carrying a nucleic acid fragment of interest into a constructed stable packaging cell which is already integrated with gag and pol genes, the rev gene, the coding sequence of the viral envelope protein (VSV-G) (preferably, and the coding sequences of the activator and/or repressor proteins of the inducible expression system) in its genome, and then simply screening for cell clones stably integrated with the construct in their genome. The present inventors have found that if all of the above genes and sequences are sequentially integrated into the host cell genome using only one transposon system (either SB system only or PB system only), upon transfer of the latter one or more of the genes or sequences, the transposase may act on the former one or more of the genes or sequences that have been introduced into the host cell and integrated into the host genome, thereby causing the former one or more of the genes or sequences to be spliced out of the host genome, and thereby reducing the efficiency of preparing a packaging/production cell line containing all genes and sequences. The inventors have found that using different transposon systems to integrate the genes or sequences into the host cell genome in two steps can effectively avoid the above-mentioned adverse effects. Thus, in the present disclosure, using different transposon systems to integrate the genes or sequences into the host cell genome in two steps means that, for example, firstly one or more of the genes or sequences are integrated into the host cell genome by using the SB system, and then the remaining one or more of the genes or sequences are integrated into the host cell genome by using the PB system; or firstly one or more of the genes or sequences are integrated into the host cell genome by using the PB system, and then the remaining one or more of the genes or sequences are integrated into the host cell genome by using the SB system. In a preferred aspect of the disclosure, firstly, gag and pol genes, the rev gene, the coding sequence of the viral envelope protein (VSV-G) (preferably, and the coding sequences of the activator and/or repressor proteins of the inducible expression system, for example, in the case of using a Tet-On and/or Cumate inducible expression system, the coding sequence of Tet-On transactivator protein and/or the coding sequence of repressor CymR protein of the Cumate operon) are integrated into the host cell genome by using SB transposon system, to construct a packaging cell; secondly, the viral genome transcription cassette carrying a nucleic acid fragment of interest is integrated into the genome of the packaging cell which is already stably integrated with gag and pol genes, the rev gene, the coding sequence of the viral envelope protein (VSV-G) (preferably, and the coding sequences of the activator and/or repressor proteins of the inducible expression system, for example, in the case of using a Tet-On and/or Cumate inducible expression system, the coding sequence of Tet-On transactivator protein and/or the coding sequence of repressor CymR protein of the Cumate operon) in its genome, by using PB transposon system, to construct a producer cell.

Unlike traditional transfection and screening methods for constructing stably transfected cell lines, both PB and SB transposon systems have the function of actively integrating inserted sequence fragments into the host cell genome. After optimization, a single transient transfection can achieve an average successful stable integration efficiency of more than 40% in the cell population under non-resistant screening conditions, and cell clones which stably integrate more than 20 copies of inserted sequence fragments in the cell genome can be obtained in one transfection operation, and multiple copies of inserted sequence fragments with different sizes and sequences can be integrated into the genome of cells in one operation. On the other hand, the efficiency of integrating the inserted sequence fragments into the host cell genome by using PB and SB transposon systems is related to the molar ratio of total transposon constructs and transposase constructs at the time of introducing each transposon construct into the cell, the amount of transposon construct introduced and the length of the inserted sequence fragments in the transposon. In general, the transposon construct may be a DNA plasmid, a minicircle DNA, a linear DNA fragment or a viral vector; the transposase construct may be a DNA plasmid, a minicircle DNA, a linear DNA fragment, a viral vector, a RNA or a protein. When a DNA plasmid is used as the construct for transposon and transposase, increasing the molar ratio of transposon/transposase plasmid at the time of transient transfection to 5:1 or more can significantly improve the efficiency of stable integration of the inserted sequence fragment in the genome of cells. In addition, the integration efficiency of the transposon in cell genomes is reduced along with the increase of the inserted sequence fragment length. There is a relatively stable linear relationship between the two. In the operation of simultaneously integrating a plurality of inserted sequence fragments in the cell genome, the copy number and molar ratio of each inserted sequence fragment finally integrated into the cell genome can be controlled by adjusting the added amount and relative molar ratio of each transposon construct according to the length of the inserted sequence fragments. In one aspect of the disclosure, gag and pol genes, the rev gene, the coding sequence of the viral envelope protein (VSV-G) (preferably, and the coding sequences of the activator and/or repressor proteins of the inducible expression system, for example, in the case of using a Tet-On and/or Cumate inducible expression system, the coding sequence of Tet-On transactivator protein and/or the coding sequence of repressor CymR protein of the Cumate operon) are first integrated into the host cell genome, preferably by using the SB transposon system. In the construction process, the above packaging cell line is constructed by transiently transfecting transposon plasmids containing the above genes and protein-coding sequences and an SB transposase plasmid under conditions of the molar ratio of the total transposon plasmids to the SB transposase plasmid being 5:1 or more, more preferably 10:1 to 40:1. The genome of constructed packaging cell line is stably integrated with at least one copy of gag and pol genes, the rev gene, the coding sequence of the viral envelope protein (VSV-G) (preferably, and the coding sequences of the activator and/or repressor proteins of the inducible expression system, for example, in the case of using a Tet-On and/or Cumate inducible expression system, the coding sequence of Tet-On transactivator protein and/or the coding sequence of repressor CymR protein of the Cumate operon); preferably adjusting the copy number of gag and pol genes integrated into the host cell genome to 2 copies or more per cell, and adjusting the copy ratio of gag and pol gene sequences to the coding sequence of VSV-G protein integrated into the host cell genome to 1:1 to 3:1; more preferably, adjusting the copy number of gag and pol genes integrated into the host cell genome to 4-6 copies per cell, and adjusting the copy ratio of gag and pol gene sequences to the coding sequence of VSV-G protein integrated into the host cell genome to 2:1 to 3:1. After the packaging cell line is constructed by the SB transposon system, the viral genome transcription cassette carrying a nucleic acid fragment of interest is integrated into the genome of the packaging cell line by using the PB transposon system. In the construction process, a stable lentivirus producer cell line is constructed by transiently transfecting a transposon plasmid containing the viral genome transcriptional cassette carrying a nucleic acid fragment of interest and a PB transposase plasmid under conditions of the molar ratio of the transposon plasmid to the PB transposase plasmid being 5:1 or more, more preferably 10:1 to 40:1. At least one copy of the viral genome transcription cassette carrying a nucleic acid fragment of interest is stably integrated in the genome of constructed producer cell line. The method of constructing a producer cell line by using the PB and SB double-transposon system has the following advantages: increasing the copy number of the inserted genes, accurately adjusting the molar ratio of each inserted sequence fragment integrated into the host cell genome, increasing the success rate of constructing and screening an optimal high-yielding producer cell line, reducing the steps and time of cell screening, reducing the number of resistance genes, and the like.

In one aspect of the disclosure, gag gene, the pol gene, the rev gene, the coding sequence of the viral envelope protein (VSV-G), the viral genome transcription cassette carrying a nucleic acid fragment of interest, and the coding sequences of the activator and/or repressor proteins of the inducible expression system (for example, the coding sequence of Tet-On transactivator rtTA protein and/or the coding sequence of repressor CymR protein of the Cumate operon) are respectively constructed in a different transposon construct; in one aspect of the disclosure, any two of the above genes or sequence fragments are constructed in one transposon construct; in one aspect of the disclosure, any three of the above genes or sequence fragments are constructed in one transposon construct; in one aspect of the disclosure, any four of the above genes or sequence fragments are constructed in one transposon construct; in one aspect of the disclosure, any five of the above genes or sequence fragments are constructed in one transposon construct; in one aspect of the disclosure, any six of the above genes or sequence fragments are constructed in one transposon construct; in one aspect of the disclosure, all of the above genes or sequence fragments are constructed in one transposon construct. In order to reduce the possibility of producing a replication-competent lentivirus (RCL) by the producer line and to facilitate optimization of the copy number ratio of each viral packaging gene and sequence fragment integrated in the host cell genome, gag gene and the pol gene are preferably constructed in the same transposon construct, and the rev gene, the coding sequence of virus envelope protein (VSV-G) and the viral genome transcription cassette carrying a nucleic acid fragment of interest are respectively constructed in three independent transposon constructs; in the case of using the Tet-On inducible expression system alone, the coding sequence of the Tet-On transactivator rtTA protein is constructed in an independent transposon construct; in the case of using the complex inducible expression system of Tet-On and Cumate, the coding sequence of the Tet-On transactivator rtTA protein and the coding sequence of the repressor CymR protein of the Cumate operon are preferably constructed in the same transposon construct.

In the present disclosure, one or more of the constructs having gag and pol genes, the rev gene, the coding sequence of the viral envelope protein (VSV-G), the viral genome transcription cassette carrying a nucleic acid fragment of interest, and the coding sequence of activator or repressor protein of an inducible expression system (for example, the coding sequence of Tet-On transactivator protein and/or the coding sequence of repressor CymR protein of the Cumate operon) further carry a screening gene sequence. In the present disclosure, the screening gene sequence is a screening gene sequence for eukaryotic cells. In one aspect of the disclosure, the screening gene may be selected from, for example, a hygromycin resistance gene, a puromycin resistance gene, a neomycin resistance gene, a blasticidin resistance gene, a bleomycin resistance gene; or the screening gene is a metabolic-pathway screening gene, for example, selected from a nucleic acid sequence encoding dihydrofolate reductase, glutamine synthetase and thymidine kinase. In one aspect of the disclosure, the expression of the screening gene can be regulated by a promoter, an internal ribosome entry site (IRES) or a P2A self-splicing polypeptide sequence, preferably by a SV40 promoter. In one aspect of the disclosure, in the step of firstly integrating gag and pol genes, the rev gene, the coding sequence of the viral envelope protein (VSV-G) (preferably, and the coding sequences of the activator and/or repressor proteins of the inducible expression system, for example, in the case of using a Tet-On and/or Cumate inducible expression system, the coding sequence of Tet-On transactivator rtTA protein and/or the coding sequence of repressor CymR protein of the Cumate operon) into the host cell genome by an SB transposon system, one or more of the constructs may carry different screening gene sequences; preferably, only one screening gene sequence is used, which can be located in any of the above construct, for example, in a construct having the coding sequences of the activator and/or repressor proteins of the inducible expression system (for example, in the case of using a Tet-On inducible expression system alone, the construct of the coding sequence of Tet-On transactivator rtTA protein carries a screening gene sequence (for example, a hygromycin resistance gene (HygroR)); or in the case of using a Tet-On and Cumate complex inducible expression system, the construct having both the coding sequence of Tet-On transactivator rtTA protein and the coding sequence of repressor CymR protein of the Cumate operon carries a screening gene sequence (for example, a hygromycin resistance gene (HygroR)). Later, in the step of construction of a producer cell line by integrating the viral genome transcription cassette carrying a nucleic acid fragment of interest into the genome of the packaging cell line by using PB transposon system, the construct of the viral genome transcription cassette carrying a nucleic acid fragment of interest preferably carries another resistance gene sequence (e.g., puromycin resistance gene (PuroR)) different from the previous one. In one aspect of the disclosure, the construct of the coding sequence of the viral envelope protein (VSV-G) carries a third resistance gene sequence (e.g., the blasticidin resistance gene (BSD)) that is different from the above two. In one aspect of the disclosure, under conditions of sufficiently high-throughput monoclonal cell screening, the constructs of the present disclosure may contain no screening gene, and stable high-yielding packaging/producer cell lines can be screened solely by the virus-producing ability of the monoclonal cells.

In the present disclosure, the lentiviral genome transcriptional cassette carrying a nucleic acid fragment of interest may be derived from a transfer vector plasmid of the second-generation lentiviral vector such as pLVPRT-tTR-KRAB (Addgene, #11648), pLenti CMVlight eGFP Puro (w771-1) (Addgene, #26431), or from a transfer vector plasmid of the third-generation lentiviral vector such as pSLIK-Hygro (Addgene, #25737), pHIV-EGFP (Addgene, #21373), pSico (Addgene, #11578), pRRLSIN.cPPT.PGK-GFP. WPRE (Addgene, #12252), Tet-pLKO-puro (Addgene, #21915), pLenti-puro (Addgene, #39481), pLVUT-tTR-KRAB (Addgene, #11651) and the like. Most of the viral genome transcriptional cassettes of the third-generation lentiviral vector and the second-generation lentiviral vector share nucleic acid sequences that play key roles in virus packaging and transduction, such as LTR, 5' non-encoding fragment, HIV-1 Ψ packaging signal, RRE, cPPT and part of gag sequences; and the main difference of the third-generation lentiviral genome transcriptional cassette from the second-generation lentiviral genome transcription cassette is that a constitutively active promoter such as CMV or RSV is used to replace the U3 sequence which acts as a promoter in the 5' LTR sequence, and the U3 sequence of the 3'-LTR sequence is deleted, so that the lentiviral transfer vector becomes a SIN (self-inactivating) vector. In the third-generation lentiviral genome transcriptional cassette, the lentiviral genomic RNA is transcribed by CMV promoter in pSLIK-Hygro, pHIV-EGFP, pSico vectors, while the lentiviral genomic RNA is transcribed by RSV promoter in pRRLSIN.cPPT.PGK-GFP. WPRE, Tet-pLKO-puro, pLenti-puro. Compared with other third-generation lentiviral transfer vector plasmids, the Tet-pLKO-puro and pLenti-puro do not contain WPRE sequence in the lentiviral genome transcriptional cassettes. The lentiviral genome transcriptional cassettes in the lentiviral transfer vector plasmids described above are all in principle applicable to the method of constructing cell lines that are stable for lentiviral production as described in the present disclosure. In one aspect of the disclosure, the sequence of lentiviral genome transcriptional cassette used in the disclosure is designed based on the nucleic acid sequence in the transfer vector plasmid of pRRLSIN.cPPT.PGK-GFP. WPRE (Addgene, #12252), and a plasmid construct containing this sequence is constructed.

The method for constructing a retrovirus/lentivirus producer cell line of the present disclosure can also construct a virus producer cell line for rapidly replacing a nucleic acid sequence of interest and/or an envelope protein, including but not limited to a rapid replacement virus producer cell line constructed by using a site-specific recombination strategy. Site-specific recombination, also known as conservative site-specific recombination, is a genetic recombination in which DNA strand exchange occurs between fragment sequences with at least a certain degree of homology. Many different genome modification strategies, such as recombinase-mediated cassette exchange (RMCE), rely on site-directed recombination, which is an advanced method for targeted introducing a transcriptional cassette or a nucleic acid fragment of interest to specific sites in a predetermined genome. Site-specific recombination generally consists of a site-specific recombinase (SSR) and a specific site sequence recognized by the site-specific recombinase and subjected to homologous recombination. Based on amino acid sequence homology and the correlation of recombinase catalytic mechanisms, most site-specific recombinases can be classified as tyrosine (Tyr) recombinases or serine (Ser) recombinases. Common tyrosine recombinases are Cre or FLP; and common serine recombinases are the classical members such as gamma-delta and Tn3 catabolic enzymes and the newly discovered φ C31-, Bxb1-, and R4 integrases. The specific site sequence that binds to the site-specific recombinase and is subjected to homologous recombination is generally 30 to 200 bases in length, and is composed of two partially inverted and repeated symmetric sequences to which the site-specific recombinase binds and an intermediate sequence flanked by the two partially inverted and repeated symmetric sequences and subjected to homologous recombination. Site-specific recombination typically occurs between two identical specific site sequences, but there are exceptions (e.g., at the attP and attB sites of the lambda phage integrase system). Cre-lox and FLP-FRT site-specific recombination systems are commonly used mature systems for recombinase-mediated cassette exchange. The Cre-lox system consists of a Cre recombinase and a loxp sequence recognized by Cre; the FLP-FRT system consists of a flippase recombinase (FLP) and a short flippase recognition target (FRT) recognized by the FLP. The two site-specific recombination systems can achieve the excision, insertion, translocation and inversion of a nucleic acid sequence fragment of interest based on the number and direction of the recognition site sequences of site-specific recombinases and the design strategy for nucleic acid mutation of the same or different DNA molecules and recognition sites. In designing a recombinase-mediated cassette exchange strategy, site-specific recombinase recognition sequences are typically set at both ends of the nucleic acid sequence to be replaced (which may itself contain a marker gene or be linked to a marker gene (the first marker gene)) (the first marker gene and the nucleic acid sequence of interest to be replaced are both located between the two specific recombinase recognition site sequences), and the cell line is screened based on the characteristics of the first marker gene. The nucleic acid sequence of interest for replacement (preferably linked to a second marker gene different from the first marker gene) is typically set in a vector (such as a plasmid or virus vector), and also has site-specific recombinase recognition sequences at both ends (the second marker gene and the nucleic acid sequence of interest for replacement are located between the two specific recombinase recognition site sequences). When a vector carrying a nucleic acid fragment of interest for replacement and a corresponding expression vector for the site-specific recombinase (e.g., a plasmid, a virus vector, a RNA carrying the coding sequence of site-specific recombinase, or a site recombinase protein) are simultaneously delivered into a cell line screened based on the first marker gene, the original nucleic acid fragment to be replaced is replaced with the nucleic acid fragment of interest for replacement carrying the second marker gene under the catalysis of the site-specific recombinase. After screening based on the characteristics of the second marker gene, a cell line of interest that successfully completes recombinase-mediated cassette exchange can be obtained. A similar strategy can be used to construct a rapid replacement virus-producer cell line for rapid replacement of a nucleic acid fragment of interest and/or an envelope protein. For example, a rapid replacement virus producer cell line is first constructed according to the method of the present disclosure based on the original nucleic acid fragment (which may itself contain a marker gene or be linked to a marker gene (the first marker gene A)) and/or the coding sequence of original envelope protein linked to a marker gene (the first marker gene B), wherein the site-specific recombinase-recognition site sequence is set at both ends of the original nucleic acid fragment (which may itself contain a marker gene or be linked to a marker gene), and/or at both ends of the coding sequence of original envelope protein linked to a marker gene. When rapidly replacing the nucleic acid fragment of interest and/or the coding sequence of the envelope protein, a vector comprising the nucleic acid fragment of interest for replacement and/or the coding sequence of the envelope protein for replacement (wherein, the nucleic acid fragment of interest for replacement and/or the coding sequence of the envelope protein for replacement has a specific recombinase-recognition site sequence at both ends and is linked to a marker gene (the second marker gene)) and a corresponding site-specific recombinase-expression vector are simultaneously delivered into the above rapid replacement virus-producer cell line, wherein the maker gene (the second marker gene A) and the nucleic acid fragment of interest for replacement are both located between two specific recombinase-recognition site sequences, and/or the maker gene (the second marker gene B) and the coding sequence of the envelope protein for replacement are both located between two specific recombinase-recognition site sequences, and the second marker gene (A and/or B) linked to the sequence for replacement is different from the first marker gene (A and/or B) used in the producer cell line that has been constructed; and then based on the second marker gene (A and/or B) linked to the nucleic acid fragment of interest for replacement and/or the coding sequence of the envelope protein for replacement, a producer cell line which successfully accomplishes recombinase-mediated cassette exchange and is capable of producing a virus containing a novel nucleic acid fragment of interest and/or a novel envelope protein is screened. The maker gene is for example a resistance gene sequence for a eukaryotic cell selected from, for example, a hygromycin resistance gene, a puromycin resistance gene, a neomycin resistance gene, a blasticidin resistance gene, a bleomycin resistance gene; or the marker gene is for example a metabolic pathway screening gene selected from, for example, a gene encoding a dihydrofolate reductase, a glutamine synthetase or a thymidine kinase; or the marker gene is for example a fluorescent protein marker gene selected from, for example, a gene sequence encoding a Green Fluorescent Protein (EGFP), a red fluorescent protein (dsRed), a cherry fluorescent protein (mcherry), a cyan fluorescent protein (ECFP), a yellow fluorescent protein (EYFP), and other mutated proteins derived from fluorescent proteins; or the marker gene is for example a protease gene used for the detection of a reporter gene selected from, for example, a gene sequence encoding a luciferase, a β-galactosidase or a chloramphenical acetyltransferase; or the marker gene is, for example, any combination of the above marker genes.

In the present disclosure, host cells that can be used to construct the retrovirus/lentivirus packaging cell line and producer cell line are mammalian cells. Examples of host cells suitable for use in the present disclosure are 293T cells, HepG2 cells, CHO cells, BHK cells, HEK293 cells, COS cells, NIH/3T3 cells, Vero cells, HT1080 cells, Te671 cells, CEM cells, NSO cells or PerC6 cells, as well as derivatives thereof. In one aspect, the host cell is a HEK293 cell or a cell derived from HEK293 cell. In one aspect, the host cell is a 293T cell. In one aspect, the producer/packaging cell can be cultured adherently or in suspension. In one aspect, the producer/packaging cell can be cultured with serum or without serum.

In the present disclosure, the tetracycline and derivatives thereof for the Tet-On inducible expression system comprise compounds similar to tetracycline in structure which can bind to the tetracycline-dependent transactivator rtTA described herein with an association constant Ka of at least $10^{-6}$ M; preferably, $10^{-9}$M or more. The derivatives of tetracycline may be selected from, for example, doxycycline (Dox), anhydrotetracycline (Atc), chlorotetracycline, oxytetracycline, and deoxytetracycline.

In the present disclosure, the Cumate functional analog which binds to the repressor CymR and can be used in the Cumate inducible expression system, can be selected from, for example, p-ethylbenzoic acid, p-propylbenzoic acid, p-isopropylbenzoic acid, p-isobutylbenzoic acid, p-tert-butylbenzoic acid, p-n-dimethylaminobenzoic acid, p-n-ethylaminobenzoic acid, and other Cumate functional analogs such as those described in U.S. Pat. No. 7,745,592.

In one aspect, the disclosure provides the following items:

Item 1. A method for preparing a producer cell for producing a retroviral vector carrying a nucleic acid fragment of interest, comprising:

integrating one or more but not all of sequences of gag and pol genes of a retrovirus, a coding sequence of a viral envelope protein, and a viral genome transcriptional cassette sequence carrying the nucleic acid fragment of interest into the genome of a host cell using a Sleeping Beauty (SB) transposon system, and further integrating the remaining one or more of the sequences of gag and pol genes of the retrovirus, the coding sequence of the viral envelope protein, and the viral genome transcriptional cassette sequence carrying the nucleic acid fragment of interest into the genome of the host cell using a PiggyBac (PB) transposon system, or integrating one or more but not all of sequences of gag and pol genes of a retrovirus, a coding sequence of a viral envelope protein, and a viral genome transcriptional cassette sequence carrying the nucleic acid fragment of interest into the genome of a host cell using a PB transposon system, and further integrating the remaining one or more of the sequences of gag and pol genes of the retrovirus, the coding sequence of the viral envelope protein, and the viral genome transcriptional cassette sequence carrying the nucleic acid fragment of interest into the genome of the host cell using a SB transposon system.

Item 2. A method for preparing a producer cell for producing a lentiviral vector carrying a nucleic acid fragment of interest, comprising:

integrating one or more but not all of sequences of gag, pol and rev genes of a lentivirus, a coding sequence of a viral envelope protein, and a viral genome transcriptional cassette sequence carrying the nucleic acid fragment of interest into the genome of a host cell using an SB transposon system, and further integrating the remaining one or more of the sequences of gag, pol and rev genes of the lentivirus, the coding sequence of the viral envelope protein, and the viral genome transcriptional cassette sequence carrying the nucleic acid fragment of interest into the genome of the host cell using a PB transposon system, or integrating one or more but not all of sequences of gag, pol and rev genes of a lentivirus, a coding sequence of a viral envelope protein, and a viral genome transcriptional cassette sequence carrying the nucleic acid fragment of interest into the genome of a host cell using a PB transposon system, and further integrating the remaining one or more of the sequences of gag, pol and rev genes of the lentivirus, the coding sequence of the viral envelope protein, and the viral genome transcriptional cassette sequence carrying the nucleic acid fragment of interest into the genome of the host cell using an SB transposon system.

Item 3. The method of item 2, wherein the integrating of the sequences of gag, pol and rev genes of the lentivirus and the coding sequence of the viral envelope protein into the genome of the host cell is achieved using the SB transposon system, and the further integrating of the viral genome transcriptional cassette sequence carrying the nucleic acid fragment of interest into the genome of the host cell is achieved using the PB transposon system, or the integrating of the sequences of gag, pol and rev genes of the lentivirus and the coding sequence of the viral envelope protein into the genome of the host cell is achieved using the PB transposon system, and the further integrating of the viral genome transcriptional cassette sequence carrying the nucleic acid fragment of interest into the genome of the host cell is achieved using the SB transposon system.

Item 4. The method of item 2, wherein the sequences of gag, pol and rev genes of the lentivirus, the coding sequence of the viral envelope protein, and the viral genome transcriptional cassette sequence carrying the nucleic acid fragment of interest are located in two or more constructs.

Item 5. The method of item 4, wherein the sequences of gag and pol genes are located in one construct, and the sequence of rev gene is located in another construct, and the coding sequence of the viral envelope protein is located in a third construct, and the viral genome transcriptional cassette sequence carrying the nucleic acid fragment of interest is located in a fourth construct.

Item 6. The method of item 2, wherein the gag, pol, and rev genes of the lentivirus are gag, pol, and rev genes of HIV-1 virus.

Item 7. The method of item 2, wherein the viral envelope protein is selected from the group consisting of feline leukemia virus (RD114) envelope protein, amphotropic retrovirus envelope protein, ecotropic retrovirus envelope protein, Baboon ape leukemia virus envelope protein, nipah virus envelope protein, Mokola virus envelope protein, Lymphocytic choriomeningitis virus envelope protein, chikungunya virus envelope protein, Ross river virus envelope protein, Semliki forest virus envelope protein, Sindbis virus envelope protein, Venezuelan equine encephalitis virus envelope protein, Western equine encephalitis virus envelope protein, influenza virus envelope protein, Fowl Plague Virus envelope protein, Chandipura virus and Piry virus envelope protein, simian immunodeficiency virus envelope protein, feline immunodeficiency virus envelope protein, equine infectious anemia virus envelope protein, Ebola virus envelope protein, rabies virus envelope protein, baculovirus envelope protein, hepatitis C virus envelope protein, feline endogenous retrovirus envelope protein, measles virus envelope protein, murine leukemia virus facultative 4070A and 10A1, Gibbon ape leukemia virus envelope protein, human immunodeficiency virus gp120 and a vesicular stomatitis virus glycoprotein (VSV-G).

Item 8. The method of item 2, wherein the viral envelope protein is a vesicular stomatitis virus glycoprotein (VSV-G).

Item 9. The method of item 2, wherein SB100X is used as a transposase in the SB system, and/or ePiggyBac is used as a transposase in the PB system.

Item 10. The method of item 2, wherein the transcription of one or more of the gag, pol and rev genes, the coding sequence of the viral envelope protein, and the viral genome transcriptional cassette carrying the nucleic acid fragment of interest is controllable.

Item 11. The method of item 10, wherein the viral envelope protein is VSV-G and the transcription of the rev gene and the coding sequence of VSV-G is controllable.

Item 12. The method of item 10, wherein the viral envelope protein is VSV-G and the transcription of the gag, pol and rev genes and the coding sequence of VSV-G is controllable.

Item 13. The method of item 10, wherein the controllable transcription is achieved by placing the gene or sequence under the control of an inducible expression system.

Item 14. The method of item 13, wherein the inducible expression system is selected from the group consisting of a tetracycline inducible expression system and a Cumate inducible expression system.

Item 15. The method of item 14, wherein the genes or sequences are under a single control of a Tet-On inducible expression system or under a dual control of a Tet-On inducible expression system and a Cumate inducible expression system.

Item 16. The method of item 15, wherein, when under the single control of the Tet-On inducible expression system, the transcription of rev is under the control of a $TRE_{3G}$ sequence, and/or the transcription of the coding sequence of VSV-G is under the control of a $TRE_{3G}$-intron sequence, and/or the transcription of gag and pol is under the control of a eukaryotic promoter-intron sequence or a $TRE_{3G}$-intron sequence;

when under the dual control of the Tet-On inducible expression system and the Cumate inducible expression system, the transcription of rev is under the control of a $TRE_{adv}$CuO sequence, a $TRE_{adv}$CuO-intron sequence, a $TRE_{3G}$ sequence, a $TRE_{3G}$CuO sequence or a $TRE_{3G}$CuO-intron sequence, and/or the transcription of VSV-G is under the control of a $TRE_{adv}$CuO sequence, a $TRE_{adv}$CuO-intron sequence, a $TRE_{3G}$-intron sequence or a $TRE_{3G}$CuO-intron sequence, and/or the transcription of gag and pol is under the control of a eukaryotic promoter-intron sequence, a $TRE_{adv}$-intron sequence, a $TRE_{adv}$CuO-intron sequence, a $TRE_{3G}$-intron sequence or a $TRE_{3G}$CuO-intron sequence.

Item 17. The method of item 16, wherein, when under the single control of the Tet-On inducible expression system, the transcription of rev is under the control of a $TRE_{3G}$ sequence, and the transcription of the coding sequence of VSV-G is under the control of a $TRE_{3G}$-intron sequence, and the transcription of gag and pol is under the control of a eukaryotic promoter-intron sequence or a $TRE_{3G}$-intron sequence;

when under the dual control of the Tet-On inducible expression system and the Cumate inducible expression system, the transcription of rev is under the control of a $TRE_{3G}$ sequence or a $TRE_{3G}$CuO sequence, and the transcription of VSV-G is under the control of a $TRE_{3G}$CuO-intron sequence, and the transcription of gag and pol is under the control of a eukaryotic promoter-intron sequence or a $TRE_{3G}$CuO-intron sequence.

Item 18. The method of item 17, wherein, when under the dual control of the Tet-On inducible expression system and the Cumate inducible expression system, the transcription of rev is under the control of a $TRE_{3G}$ sequence, and the transcription of VSV-G is under the control of a $TRE_{3G}$CuO-intron sequence, and the transcription of gag and pol is under the control of a $TRE_{3G}$CuO-intron sequence; and the copy number of gag/pol gene inserted into the genome of the host cell is 2-8 copies/cell, and the ratio of the copy number of gag/pol to VSV-G inserted into the genome of the host cell is 1:1 to 4:1.

Item 19. The method of item 18, wherein the copy number of gag/pol gene inserted into the genome of the host cell is 4-6 copies/cell, and the ratio of the copy number of gag/pol to VSV-G inserted into the genome of the host cell is 2:1 to 3:1.

Item 20. The method of item 15, wherein a coding sequence of a Tet-On transactivator protein, or a coding sequence of a Tet-On transactivator protein and a coding sequence of a repressor CymR protein of Cumate operon, is/are integrated into the genome of the host cell using an SB transposon system or a PB transposon system.

Item 21. The method of item 20, wherein the Tet-On transactivator protein is $rtTA_{3G}$.

Item 22. The method of item 15, wherein the sequences of gag, pol and rev genes of the lentivirus, the coding sequence of the viral envelope protein, and the coding sequence of the Tet-On transactivator protein, or the coding sequence of the Tet-On transactivator protein and the coding sequence of the repressor CymR protein of Cumate operon are integrated into the genome of the host cell using an SB transposon system, and then the viral genome transcriptional cassette sequence carrying the nucleic acid fragment of interest is further integrated into the genome of the host cell using a PB transposon system; or the sequences of gag, pol and rev genes of the lentivirus, the coding sequence of the viral envelope protein, and the coding sequence of the Tet-On transactivator protein, or the coding sequence of the Tet-On transactivator protein and the coding sequence of the repressor CymR protein of Cumate operon are integrated into the genome of the host cell using a PB transposon system, and then the viral genome transcriptional cassette sequence carrying the nucleic acid fragment of interest is further integrated into the genome of the host cell using an SB transposon system.

Item 23. A producer cell prepared by the method of any one of items 1-22.

Item 24. The producer cell of item 23, wherein the producer cell was deposited at the China General Microbiological Culture Collection Center (CGMCC) on Apr. 13, 2020 with CGMCC No. 19675.

Item 25. A producer cell for producing a retroviral vector carrying a nucleic acid fragment of interest, wherein the producer cell is integrated in the genome thereof with a sequence of gag and pol genes of a retrovirus, a coding sequence of a viral envelope protein, and a viral genome transcriptional cassette sequence carrying the nucleic acid fragment of interest; wherein each of the sequence of the gag and pol genes, the coding sequence of the viral envelope protein, and the viral genome transcriptional cassette sequence carrying the nucleic acid fragment of interest has IR/DR sequences for recognition by an SB transposase or ITR sequences for recognition by a PB transposase at both ends thereof, and both the IR/DR sequences and the ITR sequences are present in the producer cell.

Item 26. The producer cell of item 25, wherein each of the sequence of the gag and pol genes and the coding sequence of the viral envelope protein has IR/DR sequences for recognition by an SB transposase at both ends thereof, and the viral genome transcriptional cassette sequence carrying the nucleic acid fragment of interest has ITR sequences for recognition by a PB transposase at both ends thereof, or each of the sequence of the gag and pol genes and the coding sequence of the viral envelope protein has ITR sequences for recognition by a PB transposase at both ends thereof, and the viral genome transcriptional cassette sequence carrying the nucleic acid fragment of interest has IR/DR sequences for recognition by an SB transposase at both ends thereof Item 27. The producer cell of item 25, wherein the retrovirus is a lentivirus, and the producer cell is further integrated in the genome thereof with a sequence of rev gene of a lentivirus, and the sequence of the rev gene has IR/DR sequences for recognition by an SB transposase or ITR sequences for recognition by a PB transposase at both ends thereof.

Item 28. The producer cell of item 27, wherein the retrovirus is an HIV-1 virus.

Item 29. The producer cell of item 27, wherein each of the sequence of the gag and pol genes, the sequence of the rev gene and the coding sequence of the viral envelope protein has IR/DR sequences for recognition by an SB transposase at both ends thereof, and the viral genome transcriptional cassette sequence carrying the nucleic acid fragment of interest has ITR sequences for recognition by a PB transposase at both ends thereof; or each of the sequence of the gag and pol genes, the sequence of the rev gene and the coding sequence of the viral envelope protein has ITR sequences for recognition by a PB transposase at both ends thereof, and the viral genome transcriptional cassette sequence carrying the nucleic acid fragment of interest has IR/DR sequences for recognition by an SB transposase at both ends thereof.

Item 30. The producer cell of item 25, wherein the viral envelope protein is a vesicular stomatitis virus glycoprotein (VSV-G).

Item 31. The producer cell of item 23 or item 25, wherein the nucleic acid fragment of interest has recognition sequences for a site-specific recombinase system at both ends thereof and/or the coding sequence of the envelope protein has recognition sequences for a site-specific recombinase system at both ends thereof.

Item 32. A system for replacing a nucleic acid fragment of interest and/or an envelope protein in a retroviral vector, comprising: the producer cell of item 31, a site-specific recombinase system, and a nucleic acid fragment of interest and/or a coding sequence of an envelope protein for replacement.

Item 33. The system of item 32, wherein the site-specific recombinase system is FLP-FRT or Cre-lox recombinase system.

Item 34. The system of item 32, wherein the original nucleic acid fragment of interest in the producer cell comprises or is linked to a marker gene and/or the coding sequence of the original envelope protein in the producer cell is linked to a marker gene, and the marker gene linked to the nucleic acid fragment of interest for replacement and/or to the coding sequence of the envelope protein for replacement is different from the original marker gene in the producer cell.

Item 35. The system of item 34, wherein the maker gene is a resistance gene sequence for a eukaryotic cell, a metabolic pathway screening gene, a fluorescent protein marker gene, a protease gene used for reporter gene detection, or any combination thereof.

Item 36. The system of item 35, wherein the resistance gene sequence is selected from a hygromycin resistance gene, a puromycin resistance gene, a neomycin resistance gene, a blasticidin resistance gene, a bleomycin resistance gene.

Item 37. The system of item 35, wherein the metabolic pathway screening gene is selected from a gene encoding dihydrofolate reductase, glutamine synthetase or thymidine kinase.

Item 38. The system of item 35, wherein the fluorescent protein marker gene is selected from a gene sequence encoding Green Fluorescent Protein (EGFP), red fluorescent protein (dsRed), cherry fluorescent protein (mcherry), cyan fluorescent protein (ECFP), yellow fluorescent protein (EYFP), and the derivatives thereof.

Item 39. The system of item 35, wherein the protease gene used for reporter gene detection is selected from a gene sequence encoding luciferase, β-galactosidase or chloramphenical acetyltransferase.

Item 40. A method for replacing a nucleic acid fragment of interest and/or an envelope protein in a retrovirus producer cell, comprising: providing the producer cell of item 31, and replacing the original nucleic acid fragment of interest and/or a coding sequence of the original envelope protein in the producer cell with a nucleic acid fragment of interest for replacement and/or a coding sequence of an envelope protein for replacement using a site-specific recombinase system.

Item 41. The method of item 40, wherein the site-specific recombinase system is a FLP-FRT or Cre-lox recombinase system.

Item 42. The method of item 40, wherein the original nucleic acid fragment of interest in the producer cell comprises or is linked to a marker gene and/or the coding sequence of the original envelope protein in the producer cell is linked to a marker gene, and the marker gene linked to the nucleic acid fragment of interest for replacement and/or the coding sequence of the envelope protein for replacement is different from the original marker gene in the producer cell.

Item 43. The method of item 42, wherein the maker gene is a resistance gene sequence for a eukaryotic cell, a metabolic pathway screening gene, a fluorescent protein marker gene, a protease gene used for reporter gene detection, or any combination thereof.

Item 44. The method of item 43, wherein the resistance gene sequence is selected from hygromycin resistance gene, puromycin resistance gene, neomycin resistance gene, blasticidin resistance gene, bleomycin resistance gene.

Item 45. The method of item 43, wherein the metabolic pathway screening gene is selected from a gene encoding dihydrofolate reductase, glutamine synthetase or thymidine kinase.

Item 46. The method of item 43, wherein the fluorescent protein marker gene is selected from a gene sequence encoding Green Fluorescent Protein (EGFP), red fluorescent protein (dsRed), cherry fluorescent protein (mcherry), cyan fluorescent protein (ECFP), yellow fluorescent protein (EYFP), and the derivatives thereof.

Item 47. The method of item 43, wherein the protease gene used for reporter gene detection is selected from a gene sequence encoding luciferase, β-galactosidase or chloramphenical acetyltransferase.

Item 48. A retrovirus producer cell obtained by the method for replacing a nucleic acid fragment of interest and/or an envelope protein in a retrovirus producer cell of item 40.

Item 49. A method for producing a retroviral vector carrying a nucleic acid fragment of interest, comprising the following steps:

adding an inducer(s) of the inducible expression system(s) to the producer cell of any one of items 23-31 or the producer cell of item 48, and collecting and purifying the retroviral vector carrying the nucleic acid fragment of interest.

Item 50. The method of item 49, wherein the inducer(s) is(are) tetracycline or a derivative thereof and/or Cumate or a functional analogue thereof.

Item 51. The method of item 50, wherein the tetracycline derivative is doxycycline.

Item 52. A retroviral vector carrying a nucleic acid fragment of interest prepared by the method of item 49.

Item 53. Use of the producer cell of any one of items 23-31, the producer cell of item 48 or the retroviral vector carrying a nucleic acid fragment of interest of item 52 in the preparation of a reagent for delivering a nucleic acid fragment of interest into a cell.

Item 54. A method for preparing a lentiviral vector packaging/producer cell, comprising: introducing sequences of gag, pol and rev genes of a lentivirus and a coding sequence of a vesicular stomatitis virus glycoprotein (VSV-G) into a host cell, wherein the transcription of one or more of the gag, pol and rev genes and the coding sequence of VSV-G is under a single control of a Tet-On inducible expression system or under a dual control of a Tet-On inducible expression system and a Cumate inducible expression system, when under the single control of the Tet-On inducible expression system, the transcription of rev is under the control of a $TRE_{3G}$ sequence, and/or the transcription of the coding sequence of VSV-G is under the control of a $TRE_{3G}$-intron sequence, and/or the transcription of gag and pol is under the control of a eukaryotic promoter-intron sequence or a $TRE_{3G}$-intron sequence; when under the dual control of the Tet-On inducible expression system and the Cumate inducible expression system, the transcription of rev is under the control of a $TRE_{adv}$CuO sequence, a $TRE_{adv}$CuO-intron sequence, a $TRE_{3G}$ sequence, a $TRE_{3G}$CuO sequence or a $TRE_{3G}$CuO-intron sequence, and/or the transcription of VSV-G is under the control of a $TRE_{adv}$CuO sequence, a $TRE_{adv}$CuO-intron sequence, a $TRE_{3G}$-intron sequence or a $TRE_{3G}$CuO-intron sequence, and/or the transcription of gag and pol is under the control of a eukaryotic promoter-intron sequence, a $TRE_{adv}$-intron sequence, a $TRE_{adv}$CuO-intron sequence, a $TRE_{3G}$-intron sequence or a $TRE_{3G}$CuO-intron sequence.

Item 55. The method of item 54, wherein, when under the single control of the Tet-On inducible expression system, the transcription of rev is under the control of a $TRE_{3G}$ sequence, and the transcription of the coding sequence of VSV-G is under the control of a $TRE_{3G}$-intron sequence, and the transcription of gag and pol is under the control of a eukaryotic promoter-intron sequence or a $TRE_{3G}$-intron sequence; when under the dual control of the Tet-On inducible expression system and the Cumate inducible expression system, the transcription of rev is under the control of a $TRE_{3G}$ sequence or a $TRE_{3G}$CuO sequence, and the transcription of VSV-G is under the control of a $TRE_{3G}$CuO-intron sequence, and the transcription of gag and pol is under the control of a eukaryotic promoter-intron sequence or a $TRE_{3G}$CuO-intron sequence.

Item 56. The method of item 54, wherein the sequences of the gag, pol and rev genes of the lentivirus and the coding sequence of VSV-G are integrated into the genome of the host cell.

Item 57. The method of item 56, wherein the sequences of the gag, pol and rev genes of the lentivirus and the coding sequence of VSV-G are integrated into the genome of the host cell by an SB or PB transposon system.

Item 58. The method of item 56, wherein, when under the dual control of the Tet-On inducible expression system and the Cumate inducible expression system, the transcription of rev is under the control of a $TRE_{3G}$ sequence, and the transcription of VSV-G is under the control of a $TRE_{3G}$CuO-intron sequence, and the transcription of gag and pol is under the control of a $TRE_{3G}$CuO-intron sequence; and the copy number of gag/pol gene inserted into the genome of the host cell is 2-8 copies/cell, and the ratio of the copy number of gag/pol to VSV-G inserted into the genome of the host cell is 1:1 to 4:1.

Item 59. The method of item 58, wherein the copy number of gag/pol gene inserted into the genome of the host cell is 4-6 copies/cell, and the ratio of the copy number of gag/pol to VSV-G inserted into the genome of the host cell is 2:1 to 3:1.

Item 60. The method of item 56, wherein after the sequences of gag, pol and rev genes of the lentivirus and the coding sequence of VSV-G being integrated into the genome of the host cell by the SB or PB transposon system, a viral genome transcriptional cassette sequence carrying a nucleic acid fragment of interest is further integrated into the genome of the host cell by the same transposon system or is further introduced into the host cell using a transient transfection method.

Item 61. A lentiviral vector packaging/producer cell, comprising sequences of gag, pol and rev genes of a lentivirus and a coding sequence of a vesicular stomatitis virus glycoprotein (VSV-G), wherein the transcription of one or more of the gag, pol and rev genes and the coding sequence of VSV-G is under a single control of a Tet-On inducible expression system or under a dual control of a Tet-On inducible expression system and a Cumate inducible expression system, when under the single control of the Tet-On inducible expression system, the transcription of rev is under the control of a $TRE_{3G}$ sequence, and/or the transcription of the coding sequence of VSV-G is under the control of a $TRE_{3G}$-intron sequence, and/or the transcription of gag and pol is under the control of a eukaryotic promoter-intron sequence or a $TRE_{3G}$-intron sequence; when under the dual control of the Tet-On inducible expression system and the Cumate inducible expression system, the transcription of rev is under the control of a $TRE_{adv}$CuO sequence, a $TRE_{adv}$CuO-intron sequence, a $TRE_{3G}$ sequence, a $TRE_{3G}$CuO sequence or a $TRE_{3G}$CuO-intron sequence, and/or the transcription of VSV-G is under the control of a $TRE_{adv}$CuO sequence, a $TRE_{adv}$CuO-intron sequence, a $TRE_{3G}$-intron sequence or a $TRE_{3G}$CuO-intron sequence, and/or the transcription of gag and pol is under the control of a eukaryotic promoter-intron sequence, a $TRE_{adv}$-intron sequence, a $TRE_{adv}$CuO-intron sequence, a $TRE_{3G}$-intron sequence or a $TRE_{3G}$CuO-intron sequence.

Item 62. The lentiviral vector packaging/producer cell of item 61, wherein the sequence of the gag gene and/or the sequence of the pol gene and/or the sequence of the rev gene of the lentivirus and/or the coding sequence of the vesicular stomatitis virus glycoprotein (VSV-G) are integrated into the genome of the packaging/producer cell.

Item 63. The lentiviral vector packaging/producer cell of item 61, wherein, when under the single control of the Tet-On inducible expression system, the transcription of rev is under the control of a $TRE_{3G}$ sequence, and the transcription of the coding sequence of VSV-G is under the control of a $TRE_{3G}$-intron sequence, and the transcription of gag and pol is under the control of a eukaryotic promoter-intron sequence or a $TRE_{3G}$-intron sequence; when under the dual control of the Tet-On inducible expression system and the Cumate inducible expression system, the transcription of rev is under the control of a $TRE_{3G}$ sequence or a $TRE_{3G}$CuO sequence, and the transcription of VSV-G is under the control of a $TRE_{3G}$CuO-intron sequence, and the transcription of gag and pol is under the control of a eukaryotic promoter-intron sequence or a $TRE_{3G}$CuO-intron sequence.

Item 64. The lentiviral vector packaging/producer cell of item 61, wherein, when under the dual control of the Tet-On inducible expression system and the Cumate inducible expression system, the transcription of rev is under the control of a $TRE_{3G}$ sequence, and the transcription of VSV-G is under the control of a $TRE_{3G}$CuO-intron sequence, and the transcription of gag and pol is under the control of a $TRE_{3G}$CuO-intron sequence, and the copy number of gag/pol gene inserted into the genome of the packaging/producer cell is 2-8 copies/cell, and the ratio of the copy number of gag/pol to VSV-G inserted into the genome of the packaging/producer cell is 1:1 to 4:1.

Item 65. The lentiviral vector packaging/producer cell of item 64, wherein the copy number of gag/pol gene inserted into the genome of the packaging/producer cell is 4-6 copies/cell, and the ratio of the copy number of gag/pol to VSV-G inserted into the genome of the host cell is 2:1 to 3:1.

Item 66. The lentiviral vector packaging/producer cell of item 61, wherein the packaging/producer cell was deposited at the China General Microbiological Culture Collection Center (CGMCC) on Apr. 13, 2020 with CGMCC No. 19674.

Item 67. A method for producing a lentiviral vector, comprising culturing the packaging/producer cell of any one of items 61 to 66 under conditions suitable for producing a lentiviral vector.

BRIEF DESCRIPTION OF THE DRAWINGS

FIG. 7A shows the effect of the copy number of $rtTA_{3G}$-CymR fragment integrated into genome on the virus-producing ability, FIG. 7B shows the effect of the copy number of rev fragment integrated into genome on the virus-producing ability, FIG. 7C shows the effect of the copy number of VSV-G fragment integrated into genome on the virus-producing ability, and FIG. 7D shows the effect of the copy number of gag/pol fragment integrated into genome on the virus-producing ability.

DETAILED DESCRIPTION

The following examples are provided to illustrate the technical solutions of the present disclosure and shall not be construed as limiting the scope and spirit of the present disclosure.

Example 1: Methods for Constructing Plasmids

Figure 1:
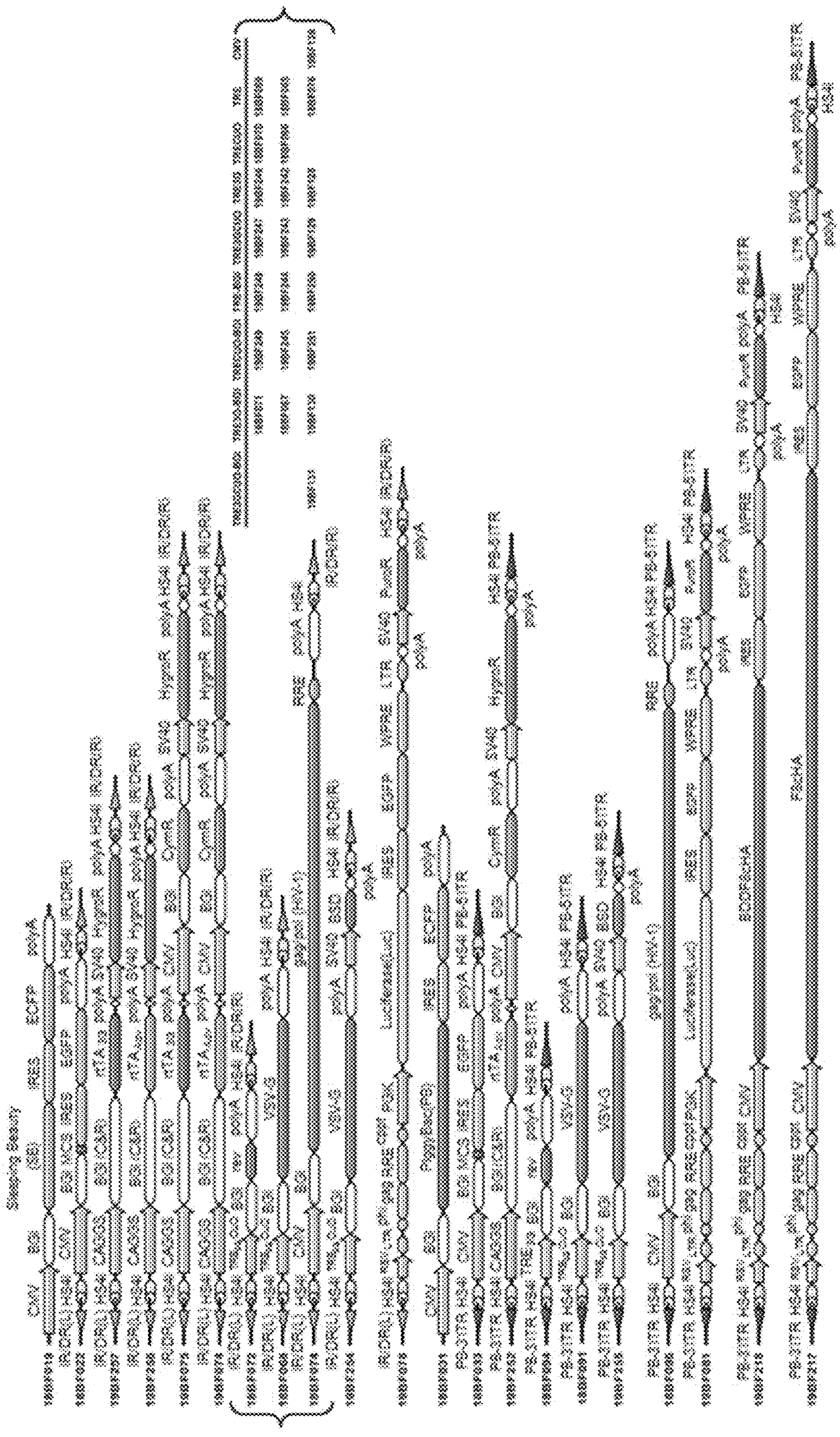
FIG. 1 shows a map of some plasmids used in the Examples.

Molecular cloning techniques used in the following examples, such as PCR amplification of DNA fragments, restriction enzyme digestion of DNA fragments, gel recovery of DNA fragments, T4 DNA ligase ligation of two or more DNA fragments, transformation of ligation-competent cells, plasmid miniprep and identification, are all well known in the art. The following reagents are involved in the examples below: PCR enzyme (Thermo, F-530S); restriction enzyme (NEB); T4 DNA ligase (Invitrogen, 15224041); DNA fragment gel recovery kit (Omega, D2500-02); plasmid mini kit (TIANGEN, DP 105-03); competent cells (XL-10 Gold, Hu Nanfenghui Biotech Co., Ltd., JZ 011); the nucleic acid sequences as set forth in SEQ ID NO: 1 to SEQ ID NO: 18 were synthesized by GenScript and used in the construction of the plasmids of the present disclosure, and the plasmid sequencing and identification was performed by Invitrogen. Maps of some of the plasmids used in the following examples are shown in FIG. 1; Table 1 shows the primer information for plasmid construction; Table 2 shows the element composition of the sequences SEQ ID NO: 1 to SEQ ID NO: 31; Table 3 is a description of the functional elements in the plasmids; Table 4 shows the numbers and corresponding names of the plasmids constructed according to the present disclosure. The sequence information of functional element adopted by each plasmid involved in the following examples is an example to carry out the present disclosure, and those skilled in the art may expect that the effect of the present disclosure can be achieved by replacing the sequence of functional element on the plasmid used in the examples below with other sequences of element having similar biological functions, including but not limited to backbone sequences (such as replication origin, resistance genes, etc.), restriction site sequences, transposon repeat sequences, response element sequences of inducible system, insulator sequences, promoter sequences, intron sequences, polyadenylation signal (PolyA) sequences, different codon-optimized gene sequences, mutants of the above sequences of functional elements and gene sequences, and the cloning positions, cloning sequences and cloning directions of the sequences of functional elements and gene sequences. The specific methods for constructing plasmids are as follows:

1. Construction of plasmids 18BF007 and 18BF004: the synthetic sequences SEQ ID NO: 2 (2900 bp) and SEQ ID NO: 3 (1386 bp) were digested with NotI and AsiSI, and ligated to NotI and AsiSI restriction sites of plasmid 18BF003 (SEQ ID NO: 1, 1893 bp), respectively, to construct plasmids 18BF007 and 18BF004, respectively.
2. Construction of plasmids 18BF011 and 18BF063: the 18BF007 plasmid was digested by MluI and SphI; and a fragment of 1730 bp was recovered by gel and ligated to MluI and SphI restriction sites of plasmid 18BF003, to construct a plasmid 18BF011. The synthetic sequence SEQ ID NO: 4 (915 bp) was digested by MluI and ClaI and ligated to MluI and ClaI restriction sites of 18BF007 to replace a CMV promoter, to construct a plasmid 18BF063.
3. Construction of plasmids 18BF072, 18BF071, 19BF249, 19BF248, 19BF247, 19BF246, 18BF070 and 18BF069: the rev gene fragment (380 bp) was PCR-amplified using pRSV-Rev (Addgene, #12253) as a template, C-rev-F (SEQ ID NO: 34) and C-rev-R (SEQ ID NO: 35) as primers, and then digested with ClaI and XhoI and ligated to ClaI and XhoI restriction sites of plasmid 18BF063, to construct a plasmid 18BF072. The synthetic sequences SEQIDNO:5 (887 bp), SEQIDNO:6 (897 bp) and SEQIDNO:7 (852 bp) were digested by MluI and ClaI and ligated to MluI and ClaI restriction sites of 18BF072 to replace a $TRE_{3G}$CuO-BGI fragment, and thereby constructing plasmids 18BF071, 19BF249 and 19BF248, respectively. Plasmids 18BF072, 18BF071, 19BF249 and 19BF248 were digested with BstBI, and fragments of 4147 bp (18BF072), 4119 bp (18BF071), 4129 bp (19BF249) and 4084 bp (19BF248) were recovered by gel and ligated with T4 ligase to construct plasmids 19BF247, 19BF246, 18BF070 and 18BF069, respectively.
4. Construction of plasmids 18BF068, 18BF067, 19BF245, 19BF244, 19BF243, 19BF242, 18BF066, 18BF065 and 19BF254: the VSV-G gene fragment (1565 bp) was PCR-amplified using pMD2.G (Addgene, #12259) as a template, C-VSVG-F (SEQ ID NO: 32) and C-VSVG-R (SEQ ID NO: 33) as primers, and then digested with ClaI and XhoI and ligated to ClaI and XhoI restriction sites of plasmid 18BF063, to construct a plasmid 18BF068. The synthetic sequences SEQIDNO:5 (887 bp), SEQIDNO:6 (897 bp) and SEQIDNO:7 (852 bp) were digested by MluI and ClaI and ligated to MluI and ClaI restriction sites of 18BF068 to replace a $TRE_{3G}$CuO-BGI fragment, and thereby constructing plasmids 18BF067, 19BF245 and 19BF244, respectively. Plasmid 18BF068 was digested with ClaI and XhoI, and a 1550 bp fragment was recovered by gel and ligated to the ClaI and XhoI sites of plasmids 19BF247, 19BF246, 18BF070 and 18BF069 to replace the rev gene, and thereby constructing plasmids 19BF243, 19BF242, 18BF066 and 18BF065, respectively. The synthetic sequence SEQ ID NO: 8 (887 bp) was digested by SpeI and PvuII, and ligated to AvrII and PmeI restriction sites of plasmid 18BF068, to construct a plasmid 19BF254.
5. Construction of plasmids 18BF074, 19BF131, 19BF130, 19BF251, 19BF250, 19BF126, 19BF129, 19BF128 and 18BF076: RRE fragment (400 bp) was PCR-amplified using pMDLg/pRRE (Addgene, #12251) as a template, C-RRE-F (SEQ ID NO:36) and C-RRE-R (SEQ ID NO:37) as primers; gag/pol gene fragment (4336 bp) was PCR-amplified using C-GagPol-F (SEQ ID NO:38) and C-GagPol-R (SEQ ID NO:39) as primers; and then the above two DNA fragments were respectively digested with XbaI/XhoI and EcoRI/XbaI, and ligated to EcoRI and XhoI restriction sites of plasmid 18BF007 to construct a plasmid 18BF074. The synthetic sequences SEQIDNO:4 (915 bp), SEQIDNO:5 (887 bp), SEQIDNO:6 (897 bp) and SEQIDNO:7 (852 bp) were digested by MluI and EcoRI and ligated to MluI and EcoRI restriction sites of 18BF074 to replace a CMV-BGI fragment, and thereby constructing plasmids 19BF131, 19BF130, 19BF251 and 19BF250, respectively. Plasmids 18BF074, 19BF131, 19BF130 and 19BF250 were digested with BstBI, and fragments of 8758 bp (18BF074), 8494 bp (18BF131), 8466 bp (19BF130) and 8421 bp (19BF250) were recovered by gel and ligated with T4 ligase to construct plasmids 19BF126, 19BF129, 19BF128 and 18BF076, respectively.
6. Construction of plasmids 19BF257, 19BF256, 19BF075 and 19BF074: the synthetic sequences SEQ ID NO: 9 (633 bp) and SEQ ID NO: 10 (1496 bp) were digested with the ClaI and XhoI and the SpeI and AgeI, respectively, and ligated in sequence to the ClaI and XhoI restriction sites and the AvrII and AgeI restriction sites of the plasmid 18BF007 to construct a plasmid 19BF073. The synthetic sequence SEQ ID NO: 11 (1979 bp) was digested by MluI and AgeI, and ligated to MluI and AgeI restriction sites of the 18BF007 plasmid to replace a CMV-BGI-MCS-pA fragment, and thereby constructing a plasmid 18BF008. The synthetic sequences SEQ ID NO: 12 (768 bp) and SEQ ID NO:

13 (765 bp) were respectively digested by ClaI and XhoI, and then respectively ligated to the ClaI and XhoI restriction sites of plasmid 18BF008, to construct plasmids 18BF085 and 18BF084 respectively. The synthetic sequence SEQ ID NO: 10 (1496 bp) was digested by SpeI and AgeI, and then respectively ligated to AvrII and AgeI restriction sites of plasmid 18BF085 and plasmid 18BF084, to construct plasmids 19BF257 and 19BF256 respectively. The plasmid 19BF073 was digested with SpeI and AgeI, and a fragment of 3821 bp was recovered by gel and respectively ligated to AvrII and AgeI restriction sites of plasmids 18BF085 and 18BF084 to construct plasmids 19BF075 and 19BF074 respectively.

7. Construction of plasmids 18BF019 and 18BF031: the synthetic sequences SEQ ID NO: 15 (1044 bp) and SEQ ID NO: 14 (1320 bp) were respectively digested by the BamHI and XhoI and the XhoI and BglII, and ligated to BamHI and BglII restriction sites of plasmid 18BF011 to construct a plasmid 18BF019. The synthetic sequences SEQ ID NO: 16 (1806 bp) and SEQ ID NO: 14 (1320 bp) were respectively digested by the BamHI and XhoI and the XhoI and BglII, and ligated to BamHI and BglII restriction sites of plasmid 18BF011 to construct a plasmid 18BF031.

8. Construction of plasmids 18BF094, 19BF255, 18BF091, 18BF096 and 19BF252: plasmids 18BF071 and 19BF254 were digested with PacI and AvrII respectively, and the DNA fragments of 1762 bp and 3838 bp were recovered by gel, and the two recovered fragments were ligated to PacI and AvrII restriction sites of plasmid 18BF004, to construct plasmids 18BF094 and 19BF255 respectively. The plasmid 18BF068 was digested with PacI, AvrII and PvuI, and a DNA fragment of 2975 bp was recovered by gel, and the recovered fragment was ligated to the PacI and AvrII restriction sites of plasmid 18BF004 to construct a plasmid 18BF091. The plasmid 18BF074 was digested with PacI and PmeI, and a DNA fragment of 6428 bp was recovered by gel and ligated to the PacI and PmeI restriction sites of plasmid 18BF004 to construct a plasmid 18BF096. The plasmid 19BF074 was digested with SpeI and PmeI, and a DNA fragment of 6513 bp was recovered by gel and ligated to the SpeI and PmeI restriction sites of plasmid 18BF004 to construct a plasmid 19BF252.

9. Construction of plasmids 19BF081, 19BF217 and 19BF218: a PGK gene fragment (706 bp) was PCR-amplified by using pRRLSIN.cPPT.PGK-GFP. WPRE (Addgene, #12252) as a template and hPGK-F (SEQ ID NO:40) and hPGK-R (SEQ ID NO:41) as primers; a luciferase gene fragment (1728 bp) was PCR-amplified by using pGL3-Basic (Promega, E1751) as a template and Luc-F (SEQ ID NO:42) and Luc-R (SEQ ID NO:43) as primers; and then the above two DNA fragments were respectively digested with the MluI and BamHI (a fragment of 538 bp by gel-recovery) and the BamHI and XhoI, and ligated to MluI and XhoI restriction sites of plasmid 19BF126 to replace the original fragment of plasmid DNA, thereby constructing a plasmid 18YYH26. The total RNA of HepG2 (ATCC HB-8065) cells and healthy human peripheral mononuclear cells (PBMC) was extracted and purified by TRIzol (ThermoFisher 15596026); a cDNA library was prepared by using the mixed total RNA of HepG2 and PBMC as a template according to the instruction of SuperScript IV (ThermoFisher 18090010); the gene fragment of F8cHA was PCR-amplified by using the cDNA library as a template and F8V1-F (SEQ ID NO:44) and F8V1HA-R(SEQ ID NO:45) as primers (7116 bp of PCR product in length, 18 bp to 7070 bp of PCR product is identical to 172 bp to 7224 bp in NM 000132.3 sequence by DNA sequencing); and then it is digested with ClaI and XhoI and ligated to ClaI and XhoI restriction sites of plasmid 19BF126 to replace the original fragment of plasmid DNA, thereby constructing a plasmid 19BF215. Two DNA fragments of 2317 bp and 2154 bp were PCR-amplified by using plasmid 19BF215 as a template and using the F8V1F (SEQ ID NO:44) and FP-BDDF8-R(SEQ ID NO:47) and the FP-BDDF8-F (SEQ ID NO:46) and F8V1HA-R(SEQ ID NO:45) as primers respectively; the two DNA fragments were ligated by fusion PCR, and a gene fragment of BDDF8cHA (4434 bp) was PCR-amplified by using F8V1F (SEQ ID NO:44) and F8V1HA-R (SEQ ID NO:45) as primers; and then it is digested with ClaI and XhoI and ligated to ClaI and XhoI restriction sites of plasmid 19BF126 to replace the original fragment of plasmid DNA, thereby constructing a plasmid 19BF216. The synthetic sequence SEQ ID NO: 18 (3610 bp) was digested by SpeI and AgeI, and ligated to SpeI and AgeI restriction sites of plasmid 18BF004, to construct a plasmid 19BF080. The synthetic sequence SEQ ID NO: 17 (1320 bp) was digested by XhoI and BglII, and ligated to Xho I and BamH I restriction sites of plasmid 19BF080, to construct a plasmid 19BF214. Plasmids 18YYH26, 19BF215, and 19BF216 were digested with Pac I and Xho I, respectively, and the DNA fragments of 2272 bp, 7792 bp and 5110 bp were recovered by gel, and the recovered fragments were ligated to the Pac I and Xho I restriction sites of plasmid 19BF214, to construct plasmids 19BF081, 19BF217 and 19BF218, respectively.

10. Construction of plasmids 18BF022, 18BF033 and 19BF078: the synthetic sequence SEQ ID NO: 17 (1320 bp) was digested with Xho I and Bgl II and ligated to the Xho I and Bgl II restriction sites of plasmid 18BF007 to construct plasmid 18BF022. The plasmid 18BF022 was digested with Mlu I, Age I and Pvu I, and a DNA fragment of 3052 bp was recovered by gel and ligated to the Mlu I and Age I restriction sites of plasmid 18BF004 to construct a plasmid 18BF033. The synthetic sequence SEQ ID NO: 18 (3610 bp) was digested by Spe I and Age I, and ligated to Spe I and Age I restriction sites of plasmid 18BF007 to replace the original fragment of plasmid DNA, thereby constructing a plasmid 19BF077. The plasmid 19BF081 was digested with Pac I and Nde I, and a DNA fragment of 3598 bp was recovered by gel and ligated to the Pac I and Nde I restriction sites of plasmid 19BF077 to construct a plasmid 19BF078.

TABLE 1

Information for Primers

| SEQ ID NO: | primer name | primer sequence (5'-3') |
|---|---|---|
| 32 | C-VSVG-F | GCTCATCGATGCCACCATGAAGT GCCTTTTGTACTTAG |
| 33 | C-VSVG-R | CAGGCTCGAGCTATTACTTTCCA AGTCGGTTCATC |

TABLE 1-continued

| Information for Primers | | |
|---|---|---|
| SEQ ID NO: | primer name | primer sequence (5'-3') |
| 34 | C-rev-F | CGATATCGATGCCACCATGGCAG GAAGAAGCGGA |
| 35 | C-rev-R | CATGCTCGAGTTACTATTCTTTA GCTCCTGACTC |
| 36 | C-RRE-F | CATGGATCTAGAAGGAGCTTTGT TCCTTG |
| 37 | C-RRE-R | CAGGCTCGAGAAGCTTGTGTAAT TGTTAATTTC |
| 38 | C-GagPol-F | GCACGAATTCGCCACCATGGGTG CGAGAGCGTC |
| 39 | C-GagPol-R | GCAGTCTAGACTATTAATCCTCA TCCTGTCTACTTG |
| 40 | hPGK-F | CATACGCGTGCTTGATATCGAAT TCCACG |
| 41 | hPGK-R | CAGATGAACTTCAGGGTCAGCTT G |
| 42 | Luc-F | TCAGGATCCATCTGCGATCTAAG TAAGCTTG |
| 43 | Luc-R | TCAACTCGAGCTAGAATTACACG GCGATC |
| 44 | F8V1-F | GTCAGATCGATGCCACCATGCAA ATAGAG |
| 45 | F8V1HA-R | CCTGCTCGAGTCATGCATAATCA GGCACGTCATAGGGGTAGCTGCC GTAGAGGTCCTGTG |
| 46 | FP-BDDF8-F | CCATTGAACCAAGAAGCTTCTCT CAAAACCCACCAGT |
| 47 | FP-BDDF8-R | ACTGGTGGGTTTTGAGAGAAGCT TCTTGGTTCAATGG |

TABLE 2

| Description of sequence elements | |
|---|---|
| SEQ ID NO: | Description of sequence elements |
| 1 | 18BF003_pma-MCS plasmid sequence (1893 bp) |
| 2 | NotI-IR/DR-HS4I-CMV-BGI-MCS-hGHpA-HS4I-IR/DR-AsiSI (2900 bp) |
| 3 | NotI- PB3'ITR-HS4I-MCS-HS4I-PB5'ITR-AsiSI (1386 bp) |
| 4 | MluI-TRE$_{3G}$CuO-BGI-ClaI-EcoRI (915 bp) |
| 5 | MluI-TRE$_{3G}$-BGI-ClaI-EcoRI (887 bp) |
| 6 | MluI-TRE$_{adv}$CuO-BGI-ClaI-EcoRI (897 bp) |
| 7 | MluI-TRE$_{adv}$-BGI-ClaI-EcoRI (852 bp) |
| 8 | SpeI-SV40p-optiBSD-SV40pA-PvuII-AgeI (887 bp) |
| 9 | ClaI-optiCymR-XhoI (633 bp) |
| 10 | SpeI-SV40p-optiHygroR-SV40pA-AgeI (1496 bp) |
| 11 | MluI-CAGGS-BGI(C&R)-MCS-SV40pA-AgeI (1979 bp) |
| 12 | ClaI-optirtTA$_{3G}$-XhoI (768 bp) |
| 13 | ClaI-rtTA$_{adv}$-XhoI (765 bp) |
| 14 | XhoI-IRES-ECFP-BglII(1320 bp) |
| 15 | BamHI-optiSB-XhoI (1044 bp) |
| 16 | BamHI-optiPB-XhoI (1806 bp) |
| 17 | XhoI-IRES-EGFP-BglII (1320 bp) |
| 18 | SpeI-RSV-LTR-phi-Gag (334)-RRE-cppt-MCS-WPRE-ppt-LTR-SV40pA-SV40p-optiPuorR-SV40pA-AgeI (3610 bp) |
| 19 | TRE$_{3G}$ response element sequence used in the present disclosure |
| 20 | TRE$_{3G}$CuO complex response element sequence used in the present disclosure |
| 21 | TRE$_{adv}$ response element sequence used in the present disclosure |
| 22 | TRE$_{adv}$CuO complex response element sequence designed in the present disclosure |
| 23 | IR/DR sequence of SB transposon |
| 24 | PB3'ITR sequence of PB transposon |
| 25 | PB5'ITR sequence of PB transposon |
| 26 | intron sequence of human β-globulin (BGI) |
| 27 | nucleic acid sequence encoding CymR |
| 28 | nucleic acid sequence encoding rtTA$_{3G}$ |
| 29 | nucleic acid sequence encoding rtTA$_{adv}$ |
| 30 | nucleic acid sequence encoding SB transposase |
| 31 | nucleic acid sequence encoding PB transposase |

TABLE 3

| Description of functional elements of plasmids | |
|---|---|
| | Description of functions |
| IR/DR(L/R) | inverted repeat (IR) and direct repeat (DR) of SB transposon system, SEQ ID NO: 23 or its complementary sequence |
| PB3'ITR/PB5'ITR | inverted terminal repeat of PB transposon system (3 terminal/5 terminal), SEQ ID NO: 24/SEQ ID NO: 25 or the complementary sequence thereof |
| HS4I | 4 core isolator sequence of chicken beta-globulin highly sensitive position |
| BGI | intron sequence of human β-globulin, SEQ ID NO: 26 |
| CMV | strong expression promoter sequence of human cytomegalovirus |
| RSV | promoter sequence of respiratory syncytial virus |
| MCS | multiple cloning site of restriction enzyme |
| CAGGS | chimeric promoter sequence of cytomegalovirus promoter enhancer part and chicken β-actin promoter |
| BGI (C&R) | chimeric intron sequence of chicken β-actin and rabbit β-globulin |
| TRE$_{3G}$CuO | response element sequence of Tet-On (based on TRE$_{3G}$) and Cumate complex inducible expression system designed in the present disclosure, SEQ ID NO: 20 |
| TRE$_{adv}$CuO | response element sequence of Tet-On (based on TRE$_{adv}$) and Cumate complex inducible expression system designed in the present disclosure, SEQ ID NO: 22 |
| TRE$_{3G}$/TRE$_{adv}$ | response element sequence of Tet-On inducible expression system, TRE$_{3G}$: SEQ ID NO: 19/TRE$_{adv}$: SEQ ID NO: 21 |
| SV40p | Simian vacuolar virus 40 promoter sequence |
| hPGK | promoter sequence derived from human phosphoglycerate kinase gene |
| IRES | ribosome entry site sequence |
| gag/pol | gene sequence encoding type I HIV virus gag and pol (identical to Addgene#12251 sequence) |
| phi | packaging signal sequence of lentiviral RNA genome |

TABLE 3-continued

| Description of functional elements of plasmids | |
|---|---|
| | Description of functions |
| RRE | rev protein response element sequence |
| LTR | long terminal repeat sequence of lentivirus, sequence containing the cis-acting element required for reverse transcription replication, the 3'LTR sequence in the present disclosure with deleted U3 sequence. |
| gag (334) | 1-334 bp sequence at the 5'terminal of HIV-1 gag protein coding sequence, containing 10 stop codons designed by point-mutations. |
| cppt | central polypurine tract sequence |
| ppt | polypurine tract sequence |
| VSV-G | gene sequence encoding vesicular stomatitis vims G glycoprotein (with the same sequence as Addgene, #12259) |
| rev | gene sequence encoding rev protein (with the same sequence as Addgene, #12253) |
| WPRE | post-transcriptional regulatory sequence of woodchuck hepatitis virus |
| optiPB | codon-optimized gene sequence encoding PiggyBac (PB) transposase, SEQ ID NO: 31 |
| optiSB | codon-optimized gene sequence encoding Sleeping Beauty (SB) transposase, SEQ ID NO: 30 |
| EGFP | gene sequence encoding green fluorescent protein |
| ECFP | Gene sequence encoding cyan fluorescent protein |
| Luciferase (Luc) | Gene sequence encoding luciferase |
| polyA (hGHpA/SV40pA) | polyadenylation sequence of transcription terminator (hGHpA human growth factor terminator/SV40pA simian vacuolar virus 40 terminator) |
| optiCymR | codon-optimized coding sequence for repressor CymR protein of Cumate inducible expression system, SEQ ID NO: 27 |
| optirtTA$_{3G}$ | codon-optimized coding sequence for Tet-On Inducible Expression System rtTA$_{3G}$ transactivator, SEQ ID NO: 28 |
| rtTA$_{adv}$ | coding sequence for Tet-On Inducible Expression System rtTA$_{adv}$ transactivator, SEQ ID NO: 29 |
| optiBSD | codon optimized sequence encoding blasticidin resistance gene |
| optiHygroR | codon optimized sequence encoding hygromycin resistance gene |
| optiPuroR | codon optimized sequence encoding puromycin resistance gene |
| F8cHA | gene sequence encoding human coagulation factor 8 (with C-terminal HA tag, consistent with NM_000132.3 sequence) |
| BDDF8cHA | gene sequence encoding human coagulation factor 8 with deletion of B protein domain(with C-terminal HA tag) |

TABLE 4

| Plasmid numbers and names | |
|---|---|
| | Plasmid name |
| 18BF003 | pma-MCS |
| 18BF007 | pmaSBT3-2xHS4I-CMV-BGI-MCS |
| 18BF004 | pmaHPBT-2xHS4I-MCS |
| 18BF011 | pmaCMV-BGI-MCS |
| 18BF063 | pmaSBT3-2xHS4I-TRE$_{3G}$CuO-BGI-MCS |
| 18BF072 | pmaSBT3-2xHS4I-TRE$_{3G}$CuO-BGI-rev |
| 18BF071 | pmaSBT3-2xHS4I-TRE$_{3G}$-BGI-rev |
| 19BF249 | pmaSBT3-2xHS4I-TRE$_{adv}$CuO-BGI-rev |
| 19BF248 | pmaSBT3-2xHS4I-TRE$_{adv}$-BGI-rev |
| 19BF247 | pmaSBT3-2xHS4I-TRE$_{3G}$CuO-rev |
| 19BF246 | pmaSBT3-2xHS4I-TRE$_{3G}$-rev |
| 18BF070 | pmaSBT3-2xHS4I-TRE$_{adv}$CuO-rev |
| 18BF069 | pmaSBT3-2xHS4I-TRE$_{adv}$-rev |
| 18BF068 | pmaSBT3-2xHS4I-TRE$_{3G}$CuO-BGI-VSVG |
| 18BF067 | pmaSBT3-2xHS4I-TRE$_{3G}$-BGI-VSVG |
| 19BF245 | pmaSBT3-2xHS4I-TRE$_{adv}$CuO-BGI-VSVG |
| 19BF244 | pmaSBT3-2xHS4I-TRE$_{adv}$-BGI-VSVG |
| 19BF243 | pmaSBT3-2xHS4I-TRE$_{3G}$CuO-VSVG |
| 19BF242 | pmaSBT3-2xHS4I-TRE$_{3G}$-VSVG |
| 18BF066 | pmaSBT3-2xHS4I-TRE$_{adv}$CuO-VSVG |
| 18BF065 | pmaSBT3-2xHS4I-TRE$_{adv}$-VSVG |
| 19BF254 | pmaSBT3-2xHS4I-TRE$_{3G}$CuO-BGI-VSVG-optiBSD |
| 18BF074 | pmaSBT3-2xHS4I-CMV-BGI-gag/pol-RRE |
| 19BF131 | pmaSBT3-2xHS4I-TRE$_{3G}$CuO-BGI-gag/pol-RRE |
| 19BF130 | pmaSBT3-2xHS4I-TRE$_{3G}$-BGI-gag/pol-RRE |
| 19BF251 | pmaSBT3-2xHS4I-TRE$_{adv}$CuO-BGI-gag/pol-RRE |
| 19BF250 | pmaSBT3-2xHS4I-TRE$_{adv}$-BGI-gag/pol-RRE |
| 19BF126 | pmaSBT3-2xHS4I-CMV-gag/pol-RRE |
| 19BF129 | pmaSBT3-2xHS4I-TRE$_{3G}$CuO-gag/pol-RRE |
| 19BF128 | pmaSBT3-2xHS4I-TRE$_{3G}$-gag/pol-RRE |
| 18BF076 | pmaSBT3-2xHS4I-TRE$_{adv}$-gag/pol-RRE |
| 19BF073 | pmaSBT3-2xHS4I-CMV-BGI-optiCymR-optiHygroR |
| 18BF008 | pmaSBT3-2xHS4I-CAGGS-BGI (C&R)-MCS |

TABLE 4-continued

| Plasmid numbers and names | |
|---|---|
| | Plasmid name |
| 18BF085 | pmaSBT3-2xHS4I-CAGGS-BGI (C&R)-optirtTA$_{3G}$ |
| 18BF084 | pmaSBT3-2xHS4I-CAGGS-BGI (C&R)-rtTA$_{adv}$ |
| 19BF257 | pmaSBT3-2xHS4I-CAGGS-BGI (C&R)-optirtTA$_{3G}$-optiHygroR |
| 19BF256 | pmaSBT3-2xHS4I-CAGGS-BGI (C&R)-rtTA$_{adv}$-optiHygroR |
| 19BF075 | pmaSBT3-2xHS4I-CAGGS-BGI (C&R)-optirtTA$_{3G}$-CMV-BGI-optiCymR-optiHygroR |
| 19BF074 | pmaSBT3-2xHS4I-CAGGS-BGI (C&R)-rtTA$_{adv}$-CMV-BGI-optiCymR-optiHygroR |
| 18BF019 | pmaCMV-BGI-optiSB-IRES-ECFP |
| 18BF031 | pmaCMV-BGI-optiPB-IRES-ECFP |
| 18BF094 | pmaHPBT-2xHS4I-TRE$_{3G}$-BGI-rev |
| 19BF255 | pmaHPBT-2xHS4I-TRE$_{3G}$CuO-BGI-VSVG-optiBSD |
| 18BF091 | pmaHPBT-2xHS4I-TRE$_{3G}$CuO-BGI-VSVG |
| 18BF096 | pmaHPBT-2xHS4I-CMV-BGI-gag/pol-RRE |
| 19BF252 | pmaHPBT-2xHS4I-CAGGS-BGI(C&R)-rtTA$_{adv}$-CMV-BGI-optiCymR-optiHygroR |
| 18YYH26 | pmaSBT3-2xHS4I-hPGK-Luc |
| 19BF215 | pmaSBT3-2xHS4I-CMV-F8cHA |
| 19BF216 | pmaSBT3-2xHS4I-CMV-BDDF8cHA |
| 19BF080 | pmaHPBT-2xHS4I-LVRSV-MCS-optiPuroR |
| 19BF214 | pmaHPBT-2xHS4I-LVRSV-MCS-IRES-EGFP-optiPuroR |
| 19BF081 | pmaHPBT-2xHS4I-LVRSV-hPGK-Luc-IRES-EGFP-optiPuroR |
| 19BF217 | pmaHPBT-2xHS4I-LVRSV-CMV-F8cHA-IRES-EGFP-PuroR |
| 19BF218 | pmaHPBT-2xHS4I-LVRSV-CMV-BDDF8cHA-IRES-EGFP-optiPuroR |
| 18BF022 | pmaSBT3-2xHS4I-CMV-BGI-MCS-IRES-EGFP |
| 18BF033 | pmaHPBT-2xHS4I-CMV-BGI-MCS-IRES-EGFP |
| 19BF077 | pmaSBT3-2xHS4I-LVRSV-MCS-optiPuroR |
| 19BF078 | pmaSTB3-2xHS4I-LVRSV-hPGK-Luc-IRES-EGFP-optiPuroR |

Example 2: Construction of Lentivirus Producer Cell Lines by Using SB and PB Double-Transposon System

1. Verification of the Specificity of SB and PB Transposon Systems

Before constructing a lentivirus producer cell line by using the SB and PB double-transposon system, it is necessary to demonstrate the specificity of the SB and PB transposon system, that is, whether the SB and PB transposase can only recognize the respective transposon binding sequence. The specificity verification experiment was carried out by transfecting SB/PB transposon plasmid (18BF022/18BF033) and SB/PB transposase plasmid (18BF019/18BF031) carrying EGFP into 293T cells, and then detecting the EGFP signal loss rate in 293T cells in serial passage to evaluate whether the two sets of transposon systems can work in a cross way, and the specific steps were as follows:

293T cells (ATCC, CRL3216) were cultured at 37° C. and 5% $CO_2$, and the medium was a DMEM complete medium (DMEM (Sigam, D6429) supplemented with 10% FBS (ExCell, 11H 116). 293T cells were seeded in a 6-well plate (Corning, 3516) at 8E5 cells per well. After 24 hours of culture, a transfection reagent was prepared in accordance with the calcium phosphate transfection protocol as described in “MolecμLar Cloning: A Laboratory Manual (Fourth edition) Chapter 15, Michael R. Green, Cold Spring Harbor Laboratory Press, 2012”, and 200 μL of the transfection reagent containing 0.12 mol/L calcium chloride, 1×HEPES buffer and 5.5 μg total plasmid was added into per well. Wherein the transposon plasmids of SB and PB were 18BF022 and 18BF033, respectively, and the reporter genes were both EGFP. The SB and PB transposase plasmids were 18BF019 and 18BF031, respectively. The transposon plasmid and the transposase plasmid were co-transfected with calcium phosphate at a molar mass of 10:1. A total of 6 co-transfection combinations were set up in the experiment, namely, (1) SB transposon and SB transposase (18BF022+18BF019); (2) PB transposon and PB transposase (18BF033+18BF031); (3) SB transposon and PB transposase (18BF022+18BF031); (4) PB transposon and SB transposase (18BF033+18BF019); (5) SB transposon and empty plasmid (18BF022+18BF003); (6) PB transposon and empty plasmid (18BF033+18BF003). After 6 hours of transfection, the medium was changed to a new DMEM complete medium. After 24 hours of transfection, the cells were digested with pancreatin (Sigam, T4799) and flow cytometry (ACEA, NovoCyte3130) was used to detect the EGFP-positive proportion and the median fluorescence intensity (MFI) of the cells, and this data was recorded as data for generation P1. Then, the cells were cultured under the condition of no screening pressure and maintained for passage every three days, the EGFP-positive proportion and the MFI value were detected by flow cytometry for each passage, and a total of 5 consecutive passages were recorded.

Figure 2:
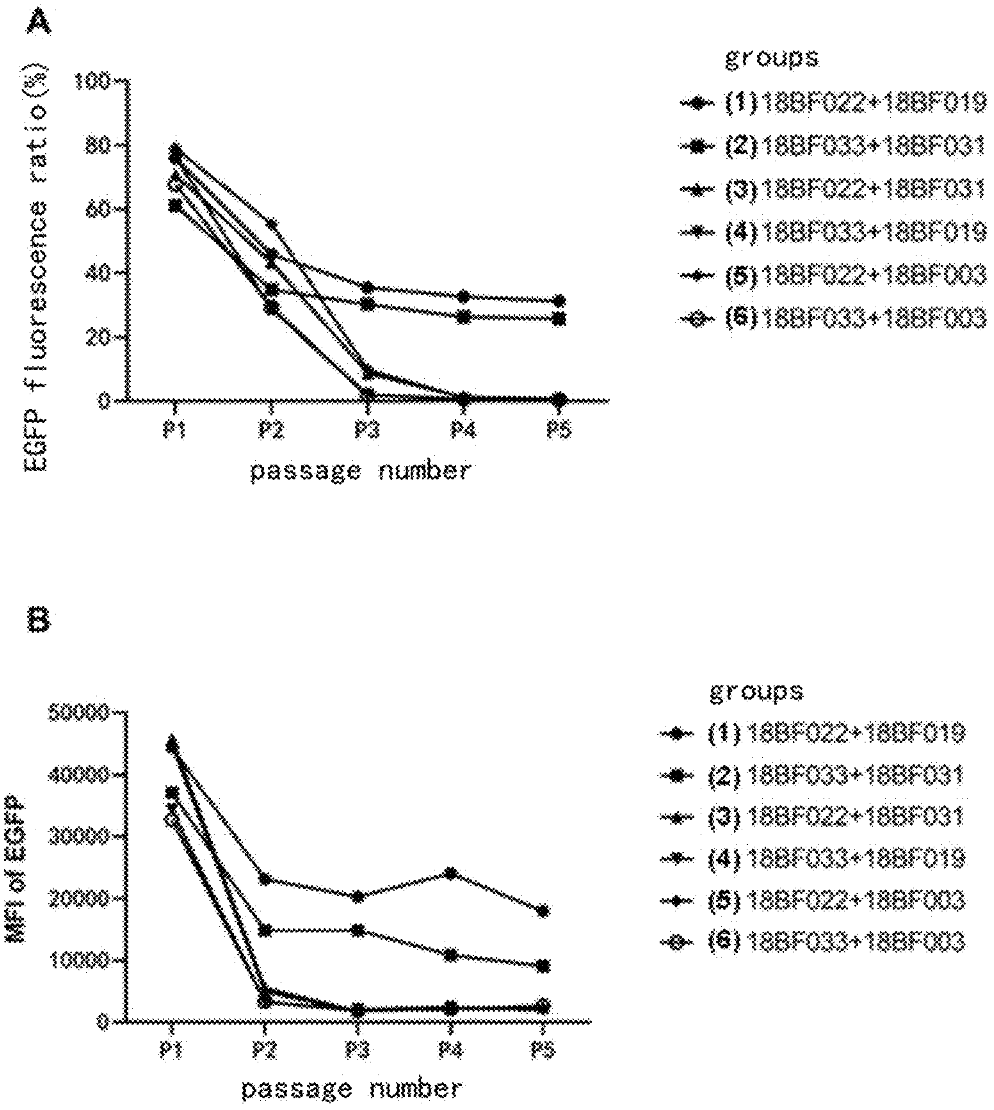
FIG. 2 shows the verification of the transposition specificity of the SB and PB transposon systems in Example 2. The abscissa represents the cell passage number, and the ordinate represents the EGFP-positive proportion of cells of various co-transfected combinations (FIG. 2A) and the median fluorescence intensity (MFI) (FIG. 2B).

FIG. 2 shows the result of specificity verification of the SB and PB. The abscissa represents the cell passage number, and the ordinate represents the EGFP-positive proportion of cells of various co-transfected combinations (FIG. 2A) and the median fluorescence intensity (MFI) (FIG. 2B). As shown in the figure: the EGFP-positive proportion in the P1 generation of the 6 groups of samples after transfection is between 61.1% and 79.1%, and the MFI is between 32685 and 44827. Then during the continuous culture without screening pressure, the EGFP-positive proportion rapidly decreases, but the decrease of EGFP in the SB experimental group 18BF022+18BF019 and the PB experimental group 18BF033+18BF031 significantly slowed down after the P2 generation; the EGFP-positive proportion is stabilized at 31.3% (SB experimental group) and 25.8% (PB experimental group) at P5 generation, and the MFI is stabilized at 18007(SB) and 9085 (PB). The EGFP-positive proportion and the MFI values of 4 experimental groups, namely an SB transposon and PB transposase cross-over group, a PB transposon and SB transposase cross-over group, an SB transposon and empty plasmid, and a PB transposon and empty plasmid, were continuously reduced; at the P5 generation, the EGFP-positive proportion was decreased to about 0.5%, and the MFI was decreased to below 3000. There was no significant difference in the results of the four groups. This result demonstrates that the SB and PB transposon systems can efficiently and stably transfect mammalian cells, and that both systems are specific.

Figure 3:
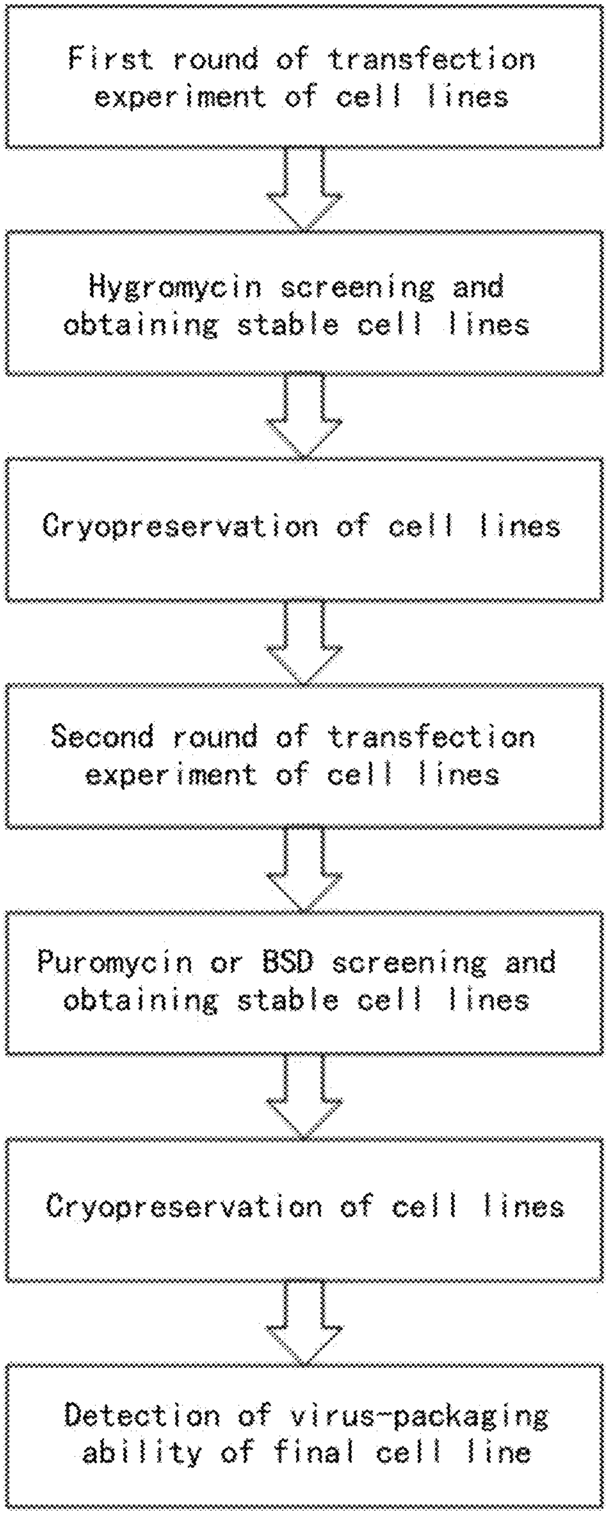
FIG. 3 shows a flow chart for constructing a producer cell stably producing a lentiviral vector in Example 2.

2: Construction of Lentivirus Producer Cell Lines by Using SB and PB Double-Transposon System with Different Plasmid Combinations In this example, by utilizing the characteristics of the SB and PB transposon systems that can efficiently integrate gene fragments into the cell genome and do not interfere with each other, the genes rev, VSV-G, gag/pol used for lentivirus packaging, the viral genome transcriptional cassette carrying a nucleic acid fragment of interest, and the coding sequence of activator rtTA and/or repressor CymR protein in the inducible expression system were combined in different ways, and then were transfected by SB and/or PB transposon system for one time or two times; and then the cells were screened to construct a producer cell line for stably producing a lentivirus vector, wherein the experimental flow refers to FIG. 3. The combination described in this example is only an example, and those skilled in the art can easily implement other combinations through the method as shown in this example. In this example, the method for constructing a stable lentivirus producer cell line of the present disclosure was developed and verified by using the hPGK-Luciferase-IRES-EGFP sequence as a nucleic acid fragment of interest, which can be any nucleic acid fragment of interest in principle without being limited by a specific nucleic acid fragment of interest.

The first round of transfection and screening experiment of cell lines: 293T cells were seeded in a 60 mm culture dish with 1.5E6 cells per culture dish and were cultured in 3 ml DMEM complete medium at 37° C. and 5% $CO_2$ for 24 hours. Cells were transfected according to the PEI method as follows: 500 μL of transfection reagent was added to each 60 mm culture dish during transfection, wherein the transfection reagent contains 9.5 μg of total plasmid; regarding the amount of plasmid added in each experimental group, please refers to Table 5, and the mass ratio of the total plasmid to PEI MAX (Polysciences, 24765-1) was 1:4; the plasmids and PEI MAX were uniformly mixed, and added to the culture dish after standing for 15 minutes; after 3 hours of transfection, the culture medium was changed to a DMEM complete culture medium, and the transfection operation was completed. After 24 hours of transfection, the cells were digested by pancreatin and were all seeded in a 100 mm petri dish (Corning, 430167). Cell drug-screening was performed by the screening resistance as shown in Table 5, and continuous screening was performed under the drug pressure for at least 3 passages until the cell line was stable, wherein the screening concentration of hygromycin (Shenggong A600230-0001) was 200 μg/ml. After the cells grew stably, the drug was removed and the cells were introduced into a DMEM complete medium for culture.

The second round of transfection and screening experiment of cell lines: the 8 cell lines constructed in the first round of transfection and screening experiment in Table 5, i. e., EuLV-F2 (deposited at the China General Microbiological Culture Collection Center (CGMCC, No. 3, No. 1 West Beichen Road, Chaoyang District, Beijing) on Apr. 13, 2020 with CGMCC No. 19674), EuLV-F3, EuLV-F4, EuLV-F5, EuLV-F7, EuLV-F8, EuLV-F9 and EuLV-F10, were respectively seeded in 8 60 mm culture dishes with 1.5E6 cells, and cultured for 24 hours. The cells were transfected according to the PEI method, and the amount of plasmid added in each experimental group was shown in Table 6. After 24 hours of transfection, the cells were digested by pancreatin and were all seeded in a 100 mm culture dish. Cell drug-screening was performed by the screening resistance as shown in Table 6, and continuous screening was performed under the drug pressure for at least 3 passages until the cell line was stable, wherein the screening concentration of puromycin (Aladdin P113126) was 2.5m/ml, and the screening concentration of Blasticidin (also known as Blasticidin S or Blastidin-S HCl, Aladdin B139600) was 10 μg/ml. After the cells grew stably, the drug was removed and the cells were introduced into a DMEM complete medium for culture. 8 cell lines, EuLV-F2-S2, EuLV-F3-S3, EuLV-F4-S4, EuLV-F5-S5, EuLV-F7-S7, EuLV-F8-S8, EuLV-F9-S9 and EuLV-F10-S10, were constructed in the second round of transfection and screening experiment. Among them, the EuLV-F2-S2 cell strain was deposited at the China General Microbiological Culture Collection Center (CGMCC, No. 3, No. 1 West Beichen Road, Chaoyang District, Beijing) on Apr. 13, 2020 with CGMCC No. 19675.

The virus-producing capacity of the stable lentivirus producer cell line was detected by a HT1080 cell Luciferase virus titer detection method. The 12 cell lines EuLV-NC-SB, EuLV-NC-PB, EuLV-F1, EuLV-F2-S2, EuLV-F3-S3, EuLV-F4-S4, EuLV-F5-S5, EuLV-F6, EuLV-F7-S7, EuLV-F8-S8, EuLV-F9-S9 and EuLV-F10-S10 were seeded in a 6-well plate (Corning 3516) with 8E+05 cells per well and cultured at 37° C. and 5% $CO_2$ in a DMEM complete medium. After 24 hours of culture, the medium was changed to a DMEM complete medium containing an inducer of 1 μg/ml DOX (doxycycline hydrochloride, Sangon Biotech (Shanghai), A600889), 200 μg/ml Cumate (Aladdin, I107765) and 5 mmol/L sodium butyrate (Sigma, 303410), to induce virus production. The lentivirus produced by a transient transfection of plasmid in 293T cell was set as a positive control, and the specific method was as follows: 293T cells were seeded at 8E+05 cells per well in a 6-well plate, and a transfection reagent (5 μg of total DNA, wherein the molar ratio of 19BF081: pMD2.G (Addgene 12259): pMDLg/PRRE (Addgene 12251): pRSV-Rev (Addgene 12253)=1:1:1:1, and the mass ratio of total DNA to PEI MAX was 1:4) was added after 24 hours of culture. 2 hours after transfection, the inducer (final concentration of 5 mmol/L sodium butyrate, 1 μg/ml DOX, 200 μg/ml Cumate) was added as above. The HT1080 cell Luciferase virus titer detection method was performed as follows: after 24 hours of adding the inducer to the cells of the experimental group and the control group, HT1080 cells were seeded into a 96-well plate (Corning 3916) with 1E4 cells per well in a DMEM complete medium. After 48 hours of induction of virus production, the medium containing the lentivirus was collected and centrifuged at 14000 rpm for 10 minutes to collect the virus supernatant. 1 hour before the addition of the virus samples, the medium of HT1080 cells was replaced with a DMEM complete medium containing 8 μg/ml polybrene (Sigam, H9268). After that, 50 μL of virus solution to be detected was added to each well of the 96-well plate, 50 μL of DMEM complete medium was added to a negative control well, and each sample and control was provided with duplicate wells. After 48 hours of culture, relative light unit RLU of each well was detected using a Steady-Glo® Luciferase Assay System (Promega, E2610) kit according to the instruction (Promega, FB037), wherein the detection instrument was a fluorescence microplate reader (Perkin Elmer Victor V).

Figure 4:
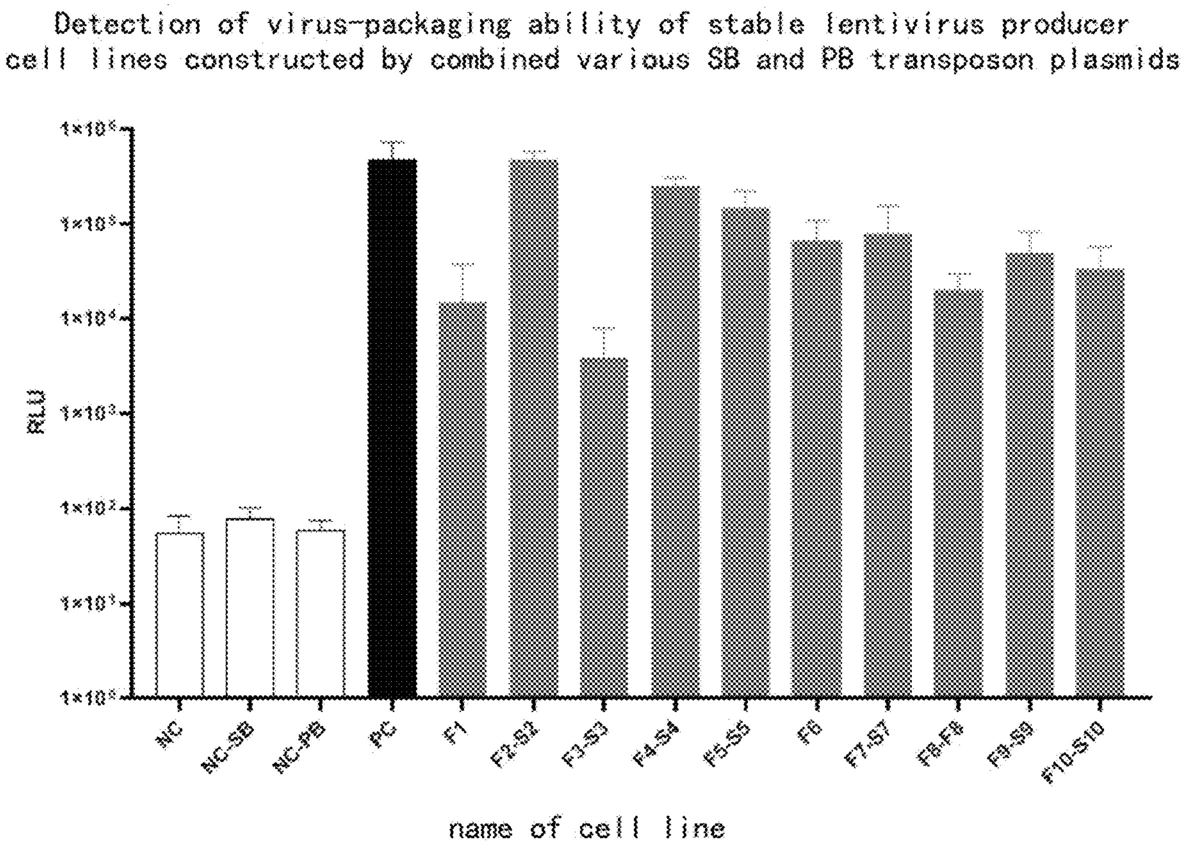
FIG. 4 shows the results of the virus-producing ability of the stable lentivirus producer cells constructed by different combinations of the SB and PB transposon systems in Example 2, wherein the abscissa shows the number of the constructed producer cells and the ordinate shows the RLU value of the Luciferase assay for determining the virus transfection titer.

FIG. 4 shows the RLU value of virus transfection titer measured by the HT1080 cell Luciferase virus titer detection method after the stable lentivirus producer cells constructed by different combinations of SB, PB transposon systems and lentivirus packaging genes were induced to produce viruses. The abscissa shows the cell line constructed by different combinations of plasmids, and the ordinate shows the relative expression value RLU of Luciferase after infecting HT1080 cells with the produced lentivirus. The results show that the stable lentivirus producer cell line can be quickly constructed by using different SB and/or PB transposons and different combinations of lentivirus packaging genes, and the virus titer can be obviously detected after the stable cell line constructed by various combinations is induced; whereas during transfection, no virus titer can be detected in the non-transposase control of NC-SB and NC-PB cells after screening, and the RLU value was not significantly different from the background control NC. In constructing a stable lentivirus producer cell line, a packaging cell containing the activator and/or repressor of an inducible expression system and the lentivirus packaging genes rev, VSV-G, gag/pol is generally constructed first, and then based on said packaging cell, a final stable lentivirus producer cell containing the lentiviral genome transcriptional cassette carrying a nucleic acid fragment of interest is constructed. Since the EuLV-F2-S2 cells exhibit optimal packaging capacity of lentiviral vector (4.68E+05 RLU), a stable lentivirus producer cell line was preferably constructed as follows in the present disclosure: firstly, a lentiviral vector packaging cell line (EuLV cells) was constructed by an SB transposon system, wherein the lentiviral vector packaging cell line contains the coding sequence of transactivator rtTA of Tet-ON inducible system and/or the coding sequence of repressor CymR of Cumate inducible system, and the lentivirus packaging gene rev, VSV-G, gag-pol gene; and then the lentiviral genome transcriptional cassette carrying a nucleic acid fragment of interest was stably inserted into the genome of the above lentiviral vector packaging cell line by a PB transposon system, to construct a stable lentivirus producer cell line.

TABLE 5

Plasmid information for the first round of cell transfection experiment in the cell line construction

| EuLV | original cell line | regulatory element (μg) 19BF074 | gag/pol (μg) 18BF074 | VSV-G (μg) 18BF068 | rev (μg) 18BF071 | transfer vector (μg) 19BF078 | transposase (μg) 18BF019 | empty plasmid (μg) 18BF003 | total plasmid (μg) | screening resistance |
|---|---|---|---|---|---|---|---|---|---|---|
| F1 | 293T | 0.68 | 3.37 | 0.49 | 0.34 | 3.63 | 0.55 | 0.45 | 9.50 | Hygromycin |
| F2 | 293T | 0.68 | 3.37 | 0.49 | 0.34 | 0.00 | 0.34 | 4.29 | 9.50 | Hygromycin |
| F3 | 293T | 0.68 | 3.37 | 0.00 | 0.34 | 3.63 | 0.51 | 0.98 | 9.50 | Hygromycin |
| F4 | 293T | 0.68 | 3.37 | 0.00 | 0.34 | 0.00 | 0.30 | 4.81 | 9.50 | Hygromycin |
| F5 | 293T | 0.68 | 0.00 | 0.49 | 0.34 | 0.00 | 0.13 | 7.87 | 9.50 | Hygromycin |
| NC-SB | 293T | 0.68 | 3.37 | 0.49 | 0.34 | 3.63 | 0.00 | 1.00 | 9.50 | Hygromycin |
| name of cell line EuLV | original cell line | regulatory element (μg) 19BF252 | gag/pol (μg) 18BF096 | VSV-G (μg) 18BF091 | rev (μg) 18BF094 | transfer vector (μg) 19BF081 | transposase (μg) 18BF031 | empty plasmid (μg) 18BF003 | total plasmid (μg) | screening resistance |
| F6 | 293T | 1.34 | 2.66 | 0.96 | 0.67 | 2.87 | 0.66 | 0.34 | 9.50 | Hygromycin |
| F7 | 293T | 1.34 | 2.66 | 0.96 | 0.67 | 0.00 | 0.47 | 3.39 | 9.50 | Hygromycin |
| F8 | 293T | 1.34 | 2.66 | 0.00 | 0.67 | 2.87 | 0.57 | 1.39 | 9.50 | Hygromycin |
| F9 | 293T | 1.34 | 2.66 | 0.00 | 0.67 | 0.00 | 0.38 | 4.45 | 9.50 | Hygromycin |
| F10 | 293T | 1.34 | 0.00 | 0.96 | 0.67 | 0.00 | 0.28 | 6.25 | 9.50 | Hygromycin |
| NC-PB | 293T | 1.34 | 2.66 | 0.96 | 0.67 | 2.87 | 0.00 | 1.00 | 9.50 | Hygromycin |

TABLE 6

Plasmid information for the second round of cell transfection in the cell line construction

| name EuLV | original cell line EuLV | regulatory element (μg) 19BF252 | gag/pol (μg) 18BF096 | VSV-G (μg) 19BF255 | rev (μg) 18BF094 | transfer vector (μg) 19BF081 | transposase (μg) 18BF031 | empty plasmid (μg) 18BF003 | total plasmid (μg) | screening resistance |
|---|---|---|---|---|---|---|---|---|---|---|
| F2-S2 | F2 | 0.00 | 0.00 | 0.00 | 0.00 | 3.63 | 0.24 | 5.63 | 9.50 | Puromycin |
| F3-S3 | F3 | 0.00 | 0.00 | 0.49 | 0.00 | 0.00 | 0.05 | 8.97 | 9.50 | Blasticidin |
| F4-S4 | F4 | 0.00 | 0.00 | 1.03 | 0.00 | 3.08 | 0.31 | 5.08 | 9.50 | Puromycin |
| F5-S5 | F5 | 0.00 | 3.37 | 0.00 | 0.00 | 3.63 | 0.48 | 2.02 | 9.50 | Puromycin |
| name of cell line EuLV | original cell line | regulatory element (μg) 19BF074 | gag/pol (μg) 18BF074 | VSV-G (μg) 19BF254 | rev (μg) 18BF071 | transfer vector (μg) 19BF078 | transposase (μg) 18BF019 | empty plasmid (μg) 18BF003 | total plasmid (μg) | screening resistance |
| F7-S7 | F7 | 0.00 | 0.00 | 0.00 | 0.00 | 2.87 | 0.17 | 6.47 | 9.50 | Puromycin |
| F8-S8 | F8 | 0.00 | 0.00 | 0.96 | 0.00 | 0.00 | 0.08 | 8.46 | 9.50 | Blasticidin |
| F9-S9 | F9 | 0.00 | 0.00 | 0.45 | 0.00 | 3.37 | 0.24 | 5.44 | 9.50 | Puromycin |
| F10-S10 | F10 | 0.00 | 2.66 | 0.00 | 0.00 | 2.87 | 0.34 | 3.63 | 9.50 | Puromycin |

Example 3: Optimization of Induced Expression of Lentiviral Genes Rev, VSV-G and gag/pol In this example, the induced expression of rev, VSV-G, and gag/pol genes was optimized. The main optimization conditions include three main aspects: (1) the selection of transactivator rtTA of the Tet-On inducible system; (2) the optimization of the inducible expression system includes the single control optimization of $TRE_{adv}$ and $TRE_{3G}$ response elements based on the Tet-On inducible system and the complex control optimization of $TRE_{adv}$CuO and $TRE_{3G}$CuO response elements based on the Tet-On and Cumate complex inducible expression system; (3) and whether a spliceable intron is linked between the 3' end of a promoter or a response element of inducible expression system and the 5' end of the regulated nucleic acid sequence. Based on the above three aspects, 8 combinations of inducible response element and intron and two Tet-On transactivators $rtTA_{adv}$ and $rtTA_{3G}$ were designed and tested to regulate the expression of lentivirus packaging genes gag/pol, VSV-G and rev, and the virus-producing titer and leaky titer of lentivirus were optimized based on various conditions. Refer to Example 1 for detailed information of plasmid construction, and the specific steps were as follows:

1. Construction of 293T-$rtTA_{adv}$-CymR and 293T-$rtTA_{3G}$-CymR Cells

Regarding the experimental procedures of 293T cell culture, PEI transfection and hygromycin screening, please refer to Example 2.293T cells were seeded at 1.5E+06 cells per 60 mm culture dish, and cultured in DMEM (Sigam, D6429) complete medium supplemented with 10% FBS (ExCell, 11H116) at 37° C. and 5% $CO_2$. After 24 hours of culture, transfection was carried out according to the PEI method, wherein the amount of total plasmid was 5.5 μg. The transfection was performed with plasmids 19BF074:18BF019 at a molar ratio of 10:1 to obtain 293T-$rtTA_{adv}$-CymR cells; and the transfection was performed with plasmids 19BF075:18BF019 at a molar ratio of 10:1 to obtain 293T-$rtTA_{3G}$-CymR cells. After transfection, a screening of 200 μg/ml hygromycin drug was performed for at least three passages. After the growth of cells under the pressure of drug screening was consistent with that of the original 293T cells, the following experiments were performed.

2. Screening and Optimization of the Gene Expression Regulation Mode of Rev, VSV-G and gag/pol by a Single Plasmid Replacement Method In 293T-$rtTA_{adv}$-CymR and 293T-$rtTA_{3G}$-CymR cells, 8 Rev plasmids, 8 VSV-G plasmids, and 9 gag/pol plasmids constructed in Example 1 were used to replace the plasmid pRSV-Rev (Addgene, #12253) expressing rev, the plasmid pMD2.G (Addgene, #12259) expressing VSV-G, and the plasmid pMDLg/pRRE (Addgene, #12251) expressing gag/pol, respectively; by using 19BF081 plasmid as a transfer vector plasmid of viral genome transcriptional cassette carrying a nucleic acid fragment of interest, viruses were prepared by PEI transient transfection in the presence or absence of DOX and Cumate inducers, and the virus-producing titer and leaky titer were evaluated by the method of HT1080 cell Luciferase virus titer detection. Under each experimental condition, only one test plasmid of inducible expression was replaced, and the other co-transformed plasmids were non-inducible expression plasmids. The eight rev test plasmids were 18BF072, 18BF071, 19BF249, 19BF248, 19BF247, 19BF246, 18BF070, and 18BF069; the eight VSV-G test plasmids were 18BF068, 18BF067, 19BF245, 19BF244, 19BF243, 19BF242, 18BF066 and 18BF065; the 9 gag/pol test plasmids were 18BF074, 19BF131, 19BF130, 19BF251, 19BF250, 19BF129, 19BF128, 18BF076 and 19BF126; the positive controls were plasmids pMD2.G, pRSV-Rev and pMDLg/pRRE. The experimental procedure was as follows:

The screened stable 293T-$rtTA_{adv}$-CymR and 293T-$rtTA_{3G}$-CymR cells were seeded in a 24-well plate at 1.5E+05 cells per well, and the culture volume was 500 μL. After 24 hours of culture, transfection was performed according to the PEI method, and 50 μl of transfection mixture was added to each well, which contained 0.8 μg of total plasmid and 3.2 μg of PEI. In the 0.8 μg of total plasmid, the molar ratio of corresponding plasmids of rev, VSV-G, gag/pol and 19BF081 was 1:1:1:1. The vector of the present disclosure was used to replace only pRSV-Rev plasmid in the rev optimization experimental group, to replace only pMD2.G plasmid in the VSV-G experimental group, to replace only pMDLg/pRRE plasmid in gag/pol experimental group; pMD2.G, pRSV-Rev and pMDLg/pRRE plasmids were transfected in the positive control group to prepare lentivirus. The plasmid and PEI were mixed well, allowed to stand for 15 minutes and added to a 24-well plate, and each sample was provided with duplicate wells. After 3 hours of transfection, the medium was changed to a complete medium containing 5 mmol/L sodium butyrate, and then 1 μg/ml DOX and 200 μg/ml Cumate inducers were added to one of the duplicate wells for each sample, which was set as an induction group; another well was added with an equal amount of medium, which was set as a non-induction group. After 48 hours of culture, the virus supernatant from each well was collected, and the RLU value of each sample under induction and non-induction conditions was detected according to the Luciferase virus titer detection method based on HT1080 cell in Example 2. The results were shown in FIG. 5.

Figure 5:
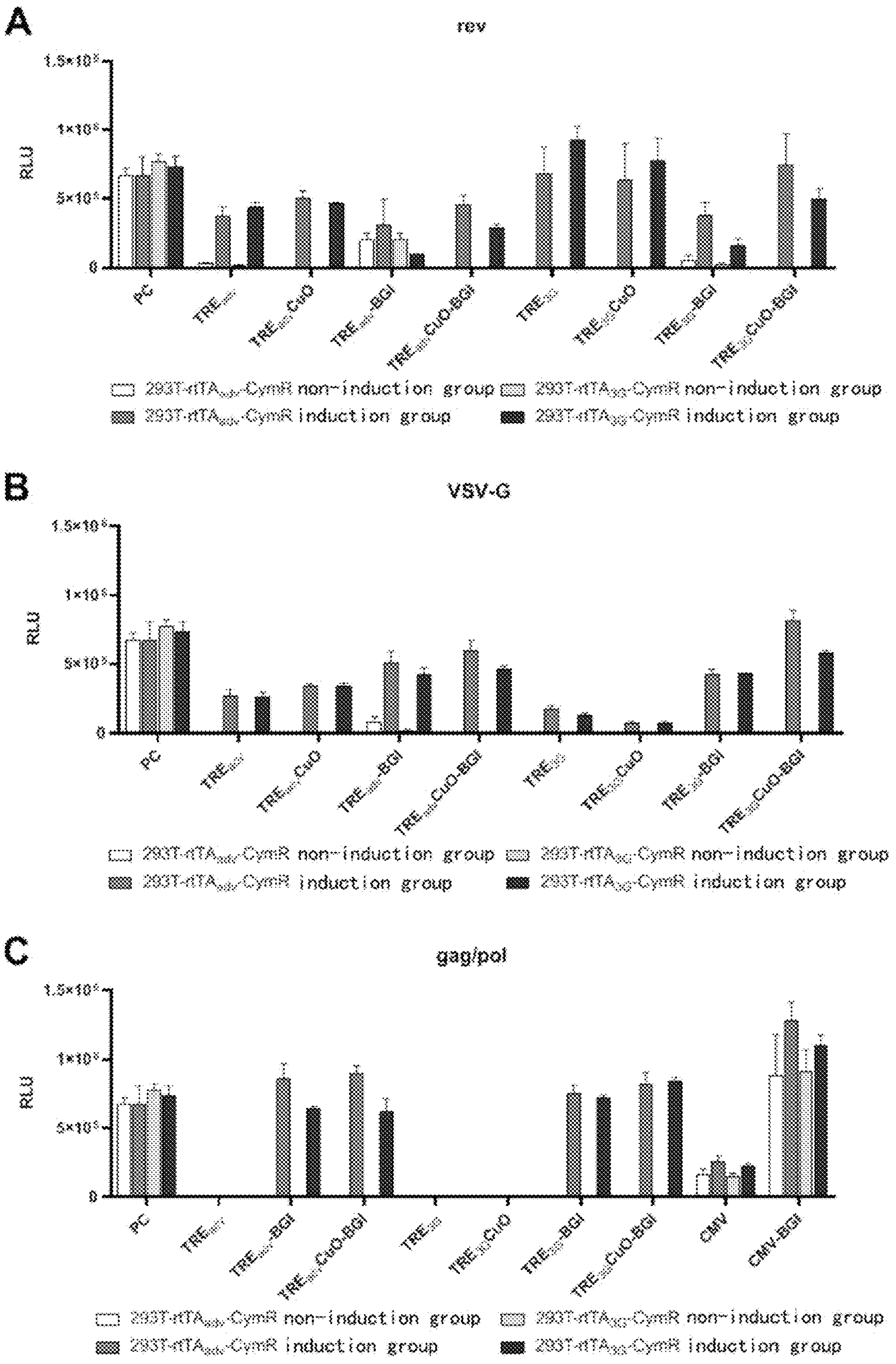
FIG. 5 shows the effect of different regulatory sequences on the virus-producing ability of a single lentiviral packaging gene in Example 3. The figure shows the result of virus titer detection, and the abscissa shows the names of different regulatory sequences to be detected; the ordinate shows the RLU value in the Luciferase assay for the detection of viral transfection titre. The detection results of induced virus-producing titer and non-induced leaky virus-producing titer of rev (FIG. 5A), VSV-G (FIG. 5B) and gag/pol (FIG. 5C) under the control of different regulatory sequences.

FIG. 5 shows Luciferase titer detection results of induced virus-producing titer and non-induced leaky titer of the lentivirus packaging genes rev (FIG. 5A), VSV-G (FIG. 5B) and gag/pol (FIG. 5C) in 293T-$rtTA_{adv}$-CymR or 293T-$rtTA_{3G}$-CymR cells under the regulation of different inducible expression system response elements and under the condition of whether a spliceable intron is linked between the 3' end of the response element and the 5' end of the regulated nucleic acid sequence.

Based on the results of induced virus-producing titer and non-induced leaky titer, the preferred regulatory elements for rev are $TRE_{adv}$CuO (18BF070), $TRE_{adv}$CuO-BGI (19BF249), $TRE_{3G}$(19BF246), $TRE_{3G}$CuO (19BF247) and $TRE_{3G}$CuO-BGI (18BF072), wherein $TRE_{3G}$, $TRE_{3G}$CuO and $TRE_{3G}$CuO-BGI are more preferred, and the corresponding average induced RLU and induced/leaky virus-producing titer ratio in 293T-$rtTA_{adv}$-CymR and 293T-$rtTA_{3G}$-CymR cells are (1) $TRE_{3G}$ (19BF246): 6.80E+05 RLU, 135 times and 9.24E+05 RLU, 322 times; (2) $TRE_{3G}$CuO (19BF247): 6.34E+05 RLU, 275 times and 7.79E+05 RLU, 279 times; (3) $TRE_{3G}$CuO-BGI (18BF072): 7.46E+05 RLU, 105 times and 4.96E+05 RLU, 68 times. Among them, for Tet-On single inducible system, the preferred transactivator is $rtTA_{3G}$, and the preferred response element is $TRE_{3G}$; for Tet-On and Cumate complex inducible system, the preferred response element is $TRE_{3G}$, $TRE_{3G}$CuO and $TRE_{3G}$CuO-BGI.

Based on the results of induced virus-producing titer and non-induced leaky titer, the preferred regulatory elements for VSV-G are $TRE_{adv}$CuO (18BF066), $TRE_{adv}$CuO-BGI (19BF245), $TRE_{3G}$-BGI (18BF067) and $TRE_{3G}$CuO-BGI (18BF068), and the corresponding average induced RLU and induced/leaky virus-producing titer ratio in 293T-rt- $TA_{adv}$-CymR and 293T-rt$TA_{3G}$-CymR cells are (1) $TRE_{adv}$ CuO (18BF066): 3.34E+05 RLU, 1323 times and 3.35E+05 RLU, 974 times; (2) $TRE_{adv}$CuO-BGI (19BF245): 5.96E+05 RLU, 506 times and 4.62E+05 RLU, 886 times; (3) $TRE_{3G}$-BGI (18BF067): 4.22E+05 RLU, 110 times and 4.27E+05 RLU, 629 times; and (4) $TRE_{3G}$CuO-BGI (18BF068): 8.09E+05 RLU, 1539 times and 5.76E5 RLU, 1260 times. Among them, for Tet-On single inducible system, the preferred transactivator is rt$TA_{3G}$, and the preferred response element is $TRE_{3G}$-BGI; for Tet-On and Cumate complex inducible system, the preferred response element is $TRE_{adv}$-CuO-BGI, $TRE_{3G}$CuO-BGI, $TRE_{3G}$CuO-BGI, and more preferably is $TRE_{3G}$CuO-BGI.

Based on the results of induced virus-producing titer and non-induced leaky titer, under the condition that no intron (BGI) sequence was linked between the 3' end of the response element and the 5' end of gag/pol coding sequence, the detection titer was below 1000 RLU, which was close to the background value, in the induction group and the non-induction group; in the absence of introns downstream from the CMV promoter (19BF126), the detection titer also decreased to 19.4% of that in the presence of introns (18BF074), indicating that the spliceable intron sequence linked between the promoter and gag/pol coding sequence was an important condition for high expression of gag/pol coding sequence. By transfection of gag/pol plasmid containing introns, the average induced RLU and induced/leaky virus-producing titer in 293T-rt$TA_{adv}$-CymR and 293T-rt$TA_{3G}$-CymR cells were (1) $TRE_{adv}$-BGI (19BF250): 8.60E+05 RLU, 87 times and 6.43E+05 RLU, 135 times; (2) $TRE_{adv}$CuO-BGI (19BF251): 9.01E+05 RLU, 413 times and 6.21E+05 RLU, 326 times; (3) $TRE_{3G}$-BGI (19BF130): 7.53E+05 RLU, 257 times and 7.16E+05 RLU, 333 times; and (4) $TRE_{3G}$CuO-BGI (19BF131): 8.22E+05 RLU, 641 times and 8.47E+0.5 RLU, 692 times; (5) CMV-BGI (18BF074): 1.28E+06 RUL and 1.10E+06 RLU. Since the expression of gag/pol coding sequence is also regulated by the rev protein, the regulation of gag/pol coding sequence was not necessary. Based on the above results, the regulatory elements of gag/pol coding sequence were preferably CMV-BGI, $TRE_{adv}$-BGI, $TRE_{adv}$-CuO-BGI, $TRE_{3G}$-BGI and $TRE_{3G}$CuO-BGI. For Tet-On single inducible system, the regulatory elements were preferably $TRE_{3G}$-BGI and CMV-BGI; for Tet-On and Cumate complex inducible system, the response elements were preferably CMV-BGI, $TRE_{adv}$-BGI, $TRE_{adv}$CuO-BGI, $TRE_{3G}$-BGI and $TRE_{3G}$CuO-BGI, more preferably CMV-BGI, $TRE_{adv}$CuO-BGI, $TRE_{3G}$CuO-BGI, and still more preferably CMV-BGI and $TRE_{3G}$CuO-BGI. With respect to the above results regarding the selection of the promoter for gag/pol coding sequence, those skilled in the art can reasonably expect that results similar to those of the CMV-BGI design can be obtained when the transcription of gag/pol is regulated using a combination of other eukaryotic promoters commonly used in the art (e.g., PGK, CAGGS, EF1a, RSV, SV40, etc.) other than the CMV promoter and other introns commonly used in the art other than BGI.

3. Comprehensive Optimization of Combinations of Rev, VSV-G and gag/pol Expression Plasmid Based on the Above Preferred Regulatory Elements According to the experimental results of the above single-plasmid-replacement method for screening and optimization of rev, VSV-G and gag/pol gene expression, (1) rev: plasmids of 18BF072, 19BF247 and 19BF246; (2) VSV-G: plasmids of 18BF068 and 18BF067; (3) gag/pol: plasmids of 18BF074, 19BF131, and 19BF130 were selected and combined as shown in Table 7 in 293T-rt$TA_{adv}$-CymR and 293T-rt$TA_{3G}$-CymR cells. According to the above method of preparing lentivirus by transient transfection in a 24-well plate, virus was prepared in the presence and absence of DOX and Cumate inducers, and the virus-producing titer and leaky titer were estimated by the HT1080 cell Luciferase virus titer detection method. The experimental conditions such as cell inoculation, the amount of plasmids and the molar ratio of each plasmid, PEI transfection, transfection and liquid exchange, induction of virus-producing, and HT1080 cell Luciferase titer detection were the same as that in the single-plasmid-replacement screening experiment of this Example, and the results were shown in FIG. 6.

Figure 6:
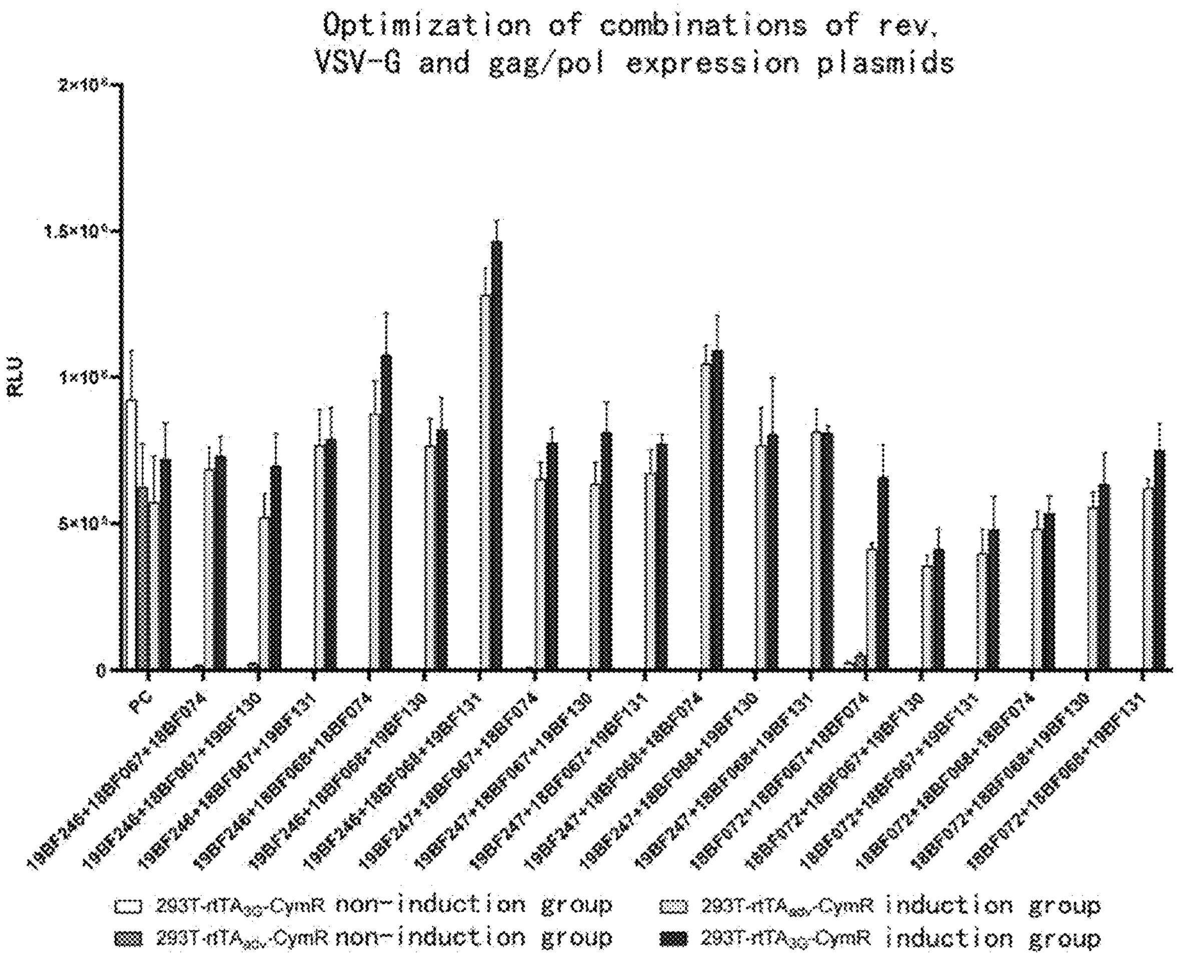
FIG. 6 shows the expression of rev, VSV-G and gag/pol regulated by optimized combinations of different regulatory sequences and comparison of induced virus-producing titer and non-induced leaky virus-producing titers in Example 3. The figure shows the results of virus titer detection. The abscissa shows the combination of plasmids with different regulatory sequences, the ordinate shows the RLU value in the Luciferase assay for the detection of virus transfection titer.

As shown in FIG. 6, based on the results of induced virus-producing titer and non-induced leaky titer, the preferred plasmid combination for Tet-On single induction was rev:19BF246, VSV-G:18BF067, and gag/pol:18BF074 or 19BF130. When 18BF074 plasmid was used, the corresponding average induced RLU and induced/leaky virus-producing titer ratio in 293T-rt$TA_{adv}$-CymR and 293T-rt$TA_{3G}$-CymR cells were 6.83E+05 RLU, 45 times and 7.28E+05 RLU, 167 times; when 19BF130 plasmid was used, the corresponding average induced RLU and induced/leaky virus-producing titer ratio in 293T-rt$TA_{adv}$-CymR and 293T-rt$TA_{3G}$-CymR cells were 5.20E+05 RLU, 24 times and 6.94E+05 RLU, 176 times, respectively. The experimental results showed that there was no significant difference in the average induced RLU and the induced/leaky virus-producing titer ratio between 18BF074 plasmid and 19BF130 plasmid, and rt$TA_{3G}$ can significantly reduce non-induced leakage compared to rt$TA_{adv}$ transactivator.

As shown in FIG. 6, regarding the optimal combination of plasmids in the Tet-On and Cumate complex inducible system, the three optimal average RLU values after induction were from the plasmid combination of 19BF246+18BF068+19BF131, 19BF246+18BF068+18BF074 and 19BF247+18BF068+18BF074. When the 19BF246+18BF068+19BF131 plasmid combination was used, the corresponding average induced RLU and induced/leaky virus-producing titer ratio in 293T-rt$TA_{adv}$-CymR and 293T-rt$TA_{3G}$-CymR cells were 1.28E+06 RLU, 1935 times and 1.46E+06 RLU, 12032 times; when the 19BF246+18BF068+18BF074 plasmid combination was used, the corresponding average induced RLU and induced/leaky virus-producing titer ratio in 293T-rt$TA_{adv}$-CymR and 293T-rt$TA_{3G}$-CymR cells were 8.75E+05 RLU, 262 times and 1.07E+06 RLU, 975 times; when the 19BF247+18BF068+18BF074 plasmid combination was used, the corresponding average induced RLU and induced/leaky virus-producing titer in 293T-rt$TA_{adv}$-CymR and 293T-rt$TA_{3G}$-CymR cells were 1.05E+06 RLU, 563 times and 1.09E+06 RLU, 839 times, respectively. Based on the above three sets of data and the data shown in FIG. 2, the preferred plasmid for rev was 19BF246 or 19BF247, more preferably 19BF246; the preferred plasmid for VSV-G was 18BF068; the preferred plasmid for gag/pol was 19BF131 and 18BF074, more preferably 19BF131; the transactivator was preferably rt$TA_{3G}$.

TABLE 7

Transfection combinations of Rev, VSV-G and gag/pol expression plasmid

| | sample number | rev | VSV-G | gag/pol | GOI | amount of total plasmid (μg) | molar ratio |
|---|---|---|---|---|---|---|---|
| 293T-rtTAadv-CymR | 19BF246 + 18BF067 + 18BF074 | 19BF246 | 18BF067 | 18BF074 | 19BF081 | 0.8 | 1:1:1:1 |
| | 19BF246 + 18BF067 + 19BF130 | 19BF246 | 18BF067 | 19BF130 | 19BF081 | 0.8 | 1:1:1:1 |
| | 19BF246 + 18BF067 + 19BF131 | 19BF246 | 18BF067 | 19BF131 | 19BF081 | 0.8 | 1:1:1:1 |
| | 19BF246 + 18BF068 + 18BF074 | 19BF246 | 18BF068 | 18BF074 | 19BF081 | 0.8 | 1:1:1:1 |
| | 19BF246 + 18BF068 + 19BF130 | 19BF246 | 18BF068 | 19BF130 | 19BF081 | 0.8 | 1:1:1:1 |
| | 19BF246 + 18BF068 + 19BF131 | 19BF246 | 18BF068 | 19BF131 | 19BF081 | 0.8 | 1:1:1:1 |
| | 19BF247 + 18BF067 + 18BF074 | 19BF247 | 18BF067 | 18BF074 | 19BF081 | 0.8 | 1:1:1:1 |
| | 19BF247 + 18BF067 + 19BF130 | 19BF247 | 18BF067 | 19BF130 | 19BF081 | 0.8 | 1:1:1:1 |
| | 19BF247 + 18BF067 + 19BF131 | 19BF247 | 18BF067 | 19BF131 | 19BF081 | 0.8 | 1:1:1:1 |
| | 19BF247 + 18BF068 + 18BF074 | 19BF247 | 18BF068 | 18BF074 | 19BF081 | 0.8 | 1:1:1:1 |
| | 19BF247 + 18BF068 + 19BF130 | 19BF247 | 18BF068 | 19BF130 | 19BF081 | 0.8 | 1:1:1:1 |
| | 19BF247 + 18BF068 + 19BF131 | 19BF247 | 18BF068 | 19BF131 | 19BF081 | 0.8 | 1:1:1:1 |
| | 18BF072 + 18BF067 + 18BF074 | 18BF072 | 18BF067 | 18BF074 | 19BF081 | 0.8 | 1:1:1:1 |
| | 18BF072 + 18BF067 + 19BF130 | 18BF072 | 18BF067 | 19BF130 | 19BF081 | 0.8 | 1:1:1:1 |
| | 18BF072 + 18BF067 + 19BF131 | 18BF072 | 18BF067 | 19BF131 | 19BF081 | 0.8 | 1:1:1:1 |
| | 18BF072 + 18BF068 + 18BF074 | 18BF072 | 18BF068 | 18BF074 | 19BF081 | 0.8 | 1:1:1:1 |
| | 18BF072 + 18BF068 + 19BF130 | 18BF072 | 18BF068 | 19BF130 | 19BF081 | 0.8 | 1:1:1:1 |
| | 18BF072 + 18BF068 + 19BF131 | 18BF072 | 18BF068 | 19BF131 | 19BF081 | 0.8 | 1:1:1:1 |
| | PC | pRSV-Rev | pMD2.G | pMDLg/pRRE | 19BF081 | 0.8 | 1:1:1:1 |
| 293T-rtTA3G-CymR | 19BF246 + 18BF067 + 18BF074 | 19BF246 | 18BF067 | 18BF074 | 19BF081 | 0.8 | 1:1:1:1 |
| | 19BF246 + 18BF067 + 19BF130 | 19BF246 | 18BF067 | 19BF130 | 19BF081 | 0.8 | 1:1:1:1 |
| | 19BF246 + 18BF067 + 19BF131 | 19BF246 | 18BF067 | 19BF131 | 19BF081 | 0.8 | 1:1:1:1 |
| | 19BF246 + 18BF068 + 18BF074 | 19BF246 | 18BF068 | 18BF074 | 19BF081 | 0.8 | 1:1:1:1 |
| | 19BF246 + 18BF068 + 19BF130 | 19BF246 | 18BF068 | 19BF130 | 19BF081 | 0.8 | 1:1:1:1 |
| | 19BF246 + 18BF068 + 19BF131 | 19BF246 | 18BF068 | 19BF131 | 19BF081 | 0.8 | 1:1:1:1 |
| | 19BF247 + 18BF067 + 18BF074 | 19BF247 | 18BF067 | 18BF074 | 19BF081 | 0.8 | 1:1:1:1 |
| | 19BF247 + 18BF067 + 19BF130 | 19BF247 | 18BF067 | 19BF130 | 19BF081 | 0.8 | 1:1:1:1 |
| | 19BF247 + 18BF067 + 19BF131 | 19BF247 | 18BF067 | 19BF131 | 19BF081 | 0.8 | 1:1:1:1 |
| | 19BF247 + 18BF068 + 18BF074 | 19BF247 | 18BF068 | 18BF074 | 19BF081 | 0.8 | 1:1:1:1 |
| | 19BF247 + 18BF068 + 19BF130 | 19BF247 | 18BF068 | 19BF130 | 19BF081 | 0.8 | 1:1:1:1 |
| | 19BF247 + 18BF068 + 19BF131 | 19BF247 | 18BF068 | 19BF131 | 19BF081 | 0.8 | 1:1:1:1 |
| | 18BF072 + 18BF067 + 18BF074 | 18BF072 | 18BF067 | 18BF074 | 19BF081 | 0.8 | 1:1:1:1 |
| | 18BF072 + 18BF067 + 19BF130 | 18BF072 | 18BF067 | 19BF130 | 19BF081 | 0.8 | 1:1:1:1 |
| | 18BF072 + 18BF067 + 19BF131 | 18BF072 | 18BF067 | 19BF131 | 19BF081 | 0.8 | 1:1:1:1 |
| | 18BF072 + 18BF068 + 18BF074 | 18BF072 | 18BF068 | 18BF074 | 19BF081 | 0.8 | 1:1:1:1 |
| | 18BF072 + 18BF068 + 19BF130 | 18BF072 | 18BF068 | 19BF130 | 19BF081 | 0.8 | 1:1:1:1 |
| | 18BF072 + 18BF068 + 19BF131 | 18BF072 | 18BF068 | 19BF131 | 19BF081 | 0.8 | 1:1:1:1 |
| | PC | pRSV-Rev | pMD2.G | pMDLg/pRRE | 19BF081 | 0.8 | 1:1:1:1 |

Example 4: Optimization of the Ratio of Stable Integration of rtTA-CymR, Rev, VSV-G and gag/pol Fragments in the Cell Genome High-efficiency production of lentivirus requires high expression level of viral gene after induction and an appropriate relative expression ratio of each viral gene. The expression level of each gene is mainly affected by the efficiency of the promoter or induction response element and the copy number of integrated into the cell genome. The efficiency of the transposon system to stably integrate the nucleic acid fragment of interest into the cell genome is affected by the length of gene fragment. The longer the nucleic acid fragment of interest is, the lower the integration efficiency becomes. Therefore, according to the length of the nucleic acid fragment of interest, the ratio of transposon plasmids during transient transfection when constructing a stable cell line can be adjusted to optimize the integration ratio of each fragment. In this Example, one preferred plasmid combination optimized in Example 3, 19BF075, 19BF246, 18BF068 and 19BF131 plasmids, was used as an example; firstly, by adjusting the molar ratio of rev, VSV-G and gag/pol single packaging gene plasmids for transient transfection during the cell line construction, the relationship between the amount of transfection plasmid added and the copy number integrated into the host cell, and the virus-producing capability of the constructed cells, were determined; then, by optimizing the molar ratio of single or multiple key genes for transient transfection during the cell line construction, the optimal copy number of genome integration and the optimal molar ratio of genome integration were determined. Based on the optimal ratio of genome integration determined in this Example, and according to the virus-producing efficiency of each promoter/response element shown in Example 3 or the compared expression-efficiency of other promoters/response elements not included in the present disclosure, the optimized insertion copy number and molar ratio of other plasmids or combinations can be derived, and thus falling within the scope of the claims supported by this Example.

1. The Effect of Adjusting the Ratio of Single-Gene Insertion on the Virus-Producing Ability of Packaging Cell Lines Regarding the experimental procedures of cell culture, PEI transfection and hygromycin screening, please refer to Examples 2.293T cells were seeded at 1.5E+06 cells per 60 mm culture dish, and cultured in DMEM (Sigam, D6429) complete medium supplemented with 10% FBS (ExCell, 11H116) at 37° C. and 5% $CO_2$. After 24 hours of culture, transfection was performed by PEI method and according to the contents of various plasmids as shown in Table 8 (the mass ratio of PEI to DNA was 4:1). After transfection, a screening of 200 μg/ml hygromycin drug was performed for at least three passages until the cell line grew stably, and a total of 17 lentivirus packaging cell lines from EuLV-R1 to R17 were constructed. After the cell lines are stabilized, referring to the method of preparing viruses in a 24-well plate in Example 3, EuLV-R1 to R17 cell lines were seeded in a 24-well plate with 1.5E+05 cells per well, and the 19BF081 plasmid was used as a transfer vector plasmid and was transfected into the above EuLV-R1 to R17 cells by PEI transient transfection (19BF081 plasmid: 0.28 μg, empty plasmid 18BF003: 0.52 μg, total plasmid 0.80 μg. The mass ratio of PEI and DNA was 4:1). After 6 hours of transfection, the medium was changed and inducers were added (final concentration of 1 μg/ml DOX, 200 μg/ml Cumate and 5 mmol/L sodium butyrate) to induce virus-production. After 48 hours, the culture supernatant was collected and the virus-producing titers of EuLV-R1 to R17 cells were detected by the HT1080 cell Luciferase virus titer detection method.

EuLV-R1 to R17 were seeded in a 24-well plate with 1.5E+05 cells per well. After 48 hours of culture, the cells were collected to extract genomic DNA and to absolutely quantify the following items by qPCR: the copy numbers of rtTA and CymR genes integrated into the genome of EuLV-R1 to R5 cell lines; the copy number of rev gene integrated into the genome of EuLV-R1 and EuLV-R6 to R9 cell lines; the copy number of VSV-G gene integrated into the genome of EuLV-R1 and EuLV-R10 to R13 cell lines; the copy numbers of gap/pol genes integrated into the genome of EuLV-R1 and EuLV-R14 to R17 cell lines; and the specific method was as follows. 1.0E+06 cells from each of the above cell lines were collected, and genomic gDNA was extracted according to the instructions of the Genomic DNA Purification Kit (TIANGEN, DP304-03), and the purified gDNA was adjusted to 50 ng/μl with the elution buffer in the kit. Plasmids 19BF074, 18BF072, 18BF068 and 18BF074 were used as standard samples for HygroR (to detect the copy numbers of rtTA and CymR), rev, VSV-G, and gag/pol genes, and diluted with deionized water to 47.9 ng/μl, 23.8 ng/μl, 30.0 ng/μl and 47.6 ng/μl, respectively; under such concentrations, each plasmid corresponded to 5.0E+09 copy number per microliter sample. The 4 standard samples were further diluted to 8.0E+06 copy number per microliter, and then were diluted in two-fold gradient to 1.56E+04 copy number per microliter, and the 10 diluted samples of the 4 standard samples were used as the qPCR standard curve of each gene to be detected. 2 μl of the above cell gDNA sample and the qPCR standard curve sample for each gene were added to qCPR reagent, and made up to 20 μl with water; wherein, the qCPR reagent comprises 10 μl Novo-Start Probe qPCR SuperMix and 0.4 μl ROX I dye (Novo-protein Scientific Inc. E091-01A), and 0.4 μl each of the forward and reverse primers and Taqman probe at a concentration of 10 μM (synthesized from General Biosystems (Anhui) Co., Ltd., the specific information for primers and probes was shown in Table 10, among which the forward and reverse primers and probe of HygroR were: SEQ ID NO: 51, SEQ ID NO:52, SEQ ID NO:53, respectively; the forward and reverse primers and probe of rev were: SEQ ID NO:54, SEQ ID NO:55, SEQ ID NO:56, respectively; the forward and reverse primers and probe for VSV-G were: SEQ ID NO:57, SEQ ID NO:58, SEQ ID NO:59, respectively; the forward and reverse primers and probe of gag/pol were: SEQ ID NO:48, SEQ ID NO:49, SEQ ID NO:50, respectively). PCR reaction was performed on a ABI 7900 real-time PCR detector under the AQ program and following the steps as follows: 95° C. 5 minutes start, 95° C. 30 seconds-60° C. 30 seconds-72° C. 30 seconds for 40 cycles, and 60° C. 30 seconds. The copy number of the gene to be tested in each sample was calculated based on the standard curve and the CT value of the sample, and then the copy number of the gene per cell was calculated according to 6 pg genomic DNA per cell.

Figure 7:
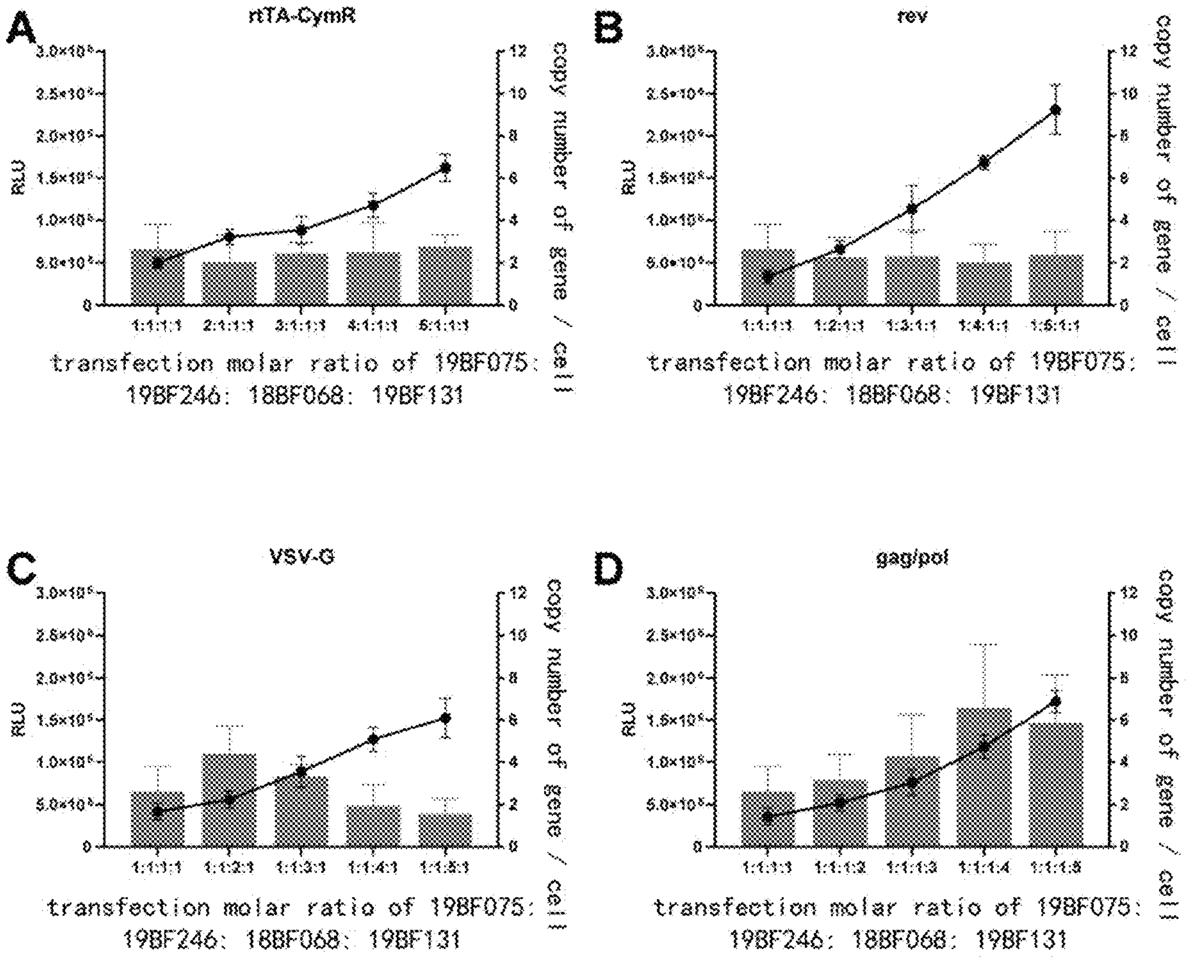
FIG. 7 shows the effect of the copy number of a single gene integrated into the host cell genome on the virus-producing ability of cells in Example 4. The abscissa shows the molar ratio of different plasmids when transfecting the cells, the left ordinate shows the RLU value of the Luciferase assay for the detection of virus transfection titer, and the right ordinate shows the average integrated copy number of the gene to be tested in the cell genome.

The results were shown in FIG. 7. The abscissa showed the molar ratio of transfected 4 plasmids when constructing cells; the bar graph corresponded to the left ordinate which showed the RLU value of induced virus-producing titer of each cell; the line graph corresponded to the right ordinate which showed the copy numbers of HygroR (detecting copy numbers of rtTA and CymR), rev, VSV-G or gag/pol fragments integrated into the genome of each cell. The results showed that (1) increasing the copy numbers of $rtTA_{3G}$-CymR (experiment result of HygroR probe) and rev fragment integrated into the cell genome had no significant effect on the virus-producing capacity of EuLV packaging cell line (FIGS. 7A and 7B). (2) When the copy number of VSV-G integrated into the genome was increased from 1 copy per cell to 2 copies per cell, the virus-producing titer increased significantly from 6.5E+05 RLU to 1.1E+06 RLU. However, as the copy number of VSV-G integrated into the genome reached 4 or more copies per cell, the virus-producing titer gradually decreased, and when the copy number integrated into the genome reached 6 copies per cell, it dropped to 3.9E+05 RLU (FIG. 7C). It indicated that the cytotoxicity of VSV-G after induced expression may increase with the increase of the copy number integrated into the genome, thereby affecting the virus-producing ability of the EuLV packaging cell line. (3) The integrated copy number of gag/pol fragment positively affected the virus-producing ability of the EuLV packaging cell line. The virus-producing titer increased with the increase of the copy number of gag/pol inserted into genome, and reached the highest virus-producing titer 1.6E+06 RLU when the copy number reached more than 4.7 copies per cell, and the virus-producing capability cannot be further increased by continuously increasing the copy number to 6 or more (FIG. 7D).

2. Further Adjustment of the Copy Number and Relative Ratio of VSV-G and gag/pol Integrated into the Genome to Optimize the Virus-Producing Ability of EuLV Packaging Cell Line Based on the above results, the copy number and relative ratio of VSV-G and gag/pol fragment integrated into the cell genome were the key to optimize the virus-producing ability of EuLV packaging cell lines, and the total transfection and molar ratio of VSV-G and gag/pol fragments needs to be further optimized. Consistent with the above method of constructing EuLV packaging cell line using SB transposon system, EuLV-VG1 to VG5 packaging cell lines were further constructed based on the contents of each plasmid shown in Table 9. After each cell line was screened by hygromycin to grow stably, by using the same method as the above-mentioned method of preparing lentivirus in a 24-well plate, the virus was prepared with the 19BF081 plasmid as the plasmid of gene of interest and the luciferase virus titer was detected by HT1080 cells; at the same time, by using the qPCR quantitative method described above, the copy number of VSV-G and gag/pol fragments per cell integrated in the genomic DNA of each cell line was detected and the results were shown in FIG. 8.

Figure 8:
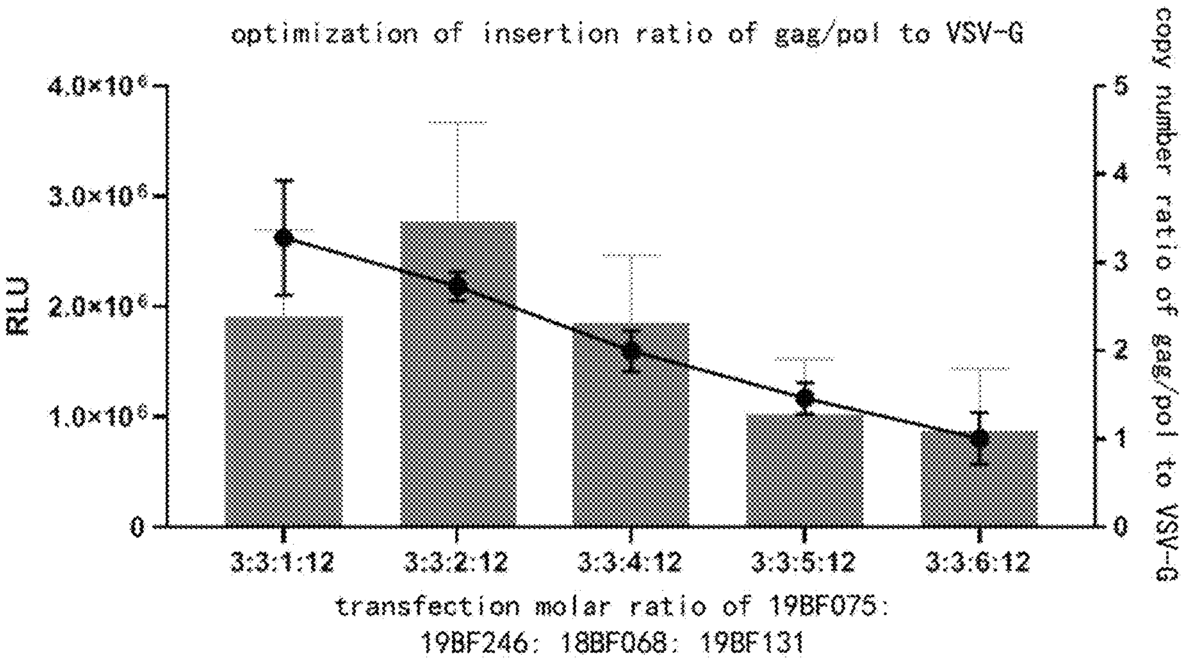
FIG. 8 shows the effect of the copy number ratio of gag/pol and VSV-G fragments integrated into the host cell genome on the virus-producing ability of cells in Example 4. The abscissa shows the molar ratio of different plasmids when transfecting the cells, the left ordinate shows the RLU value of the Luciferase assay for the detection of virus transfection titer, and the right ordinate shows the copy number ratio of gag/pol and VSV-G fragments integrated into the cell genome.

The results were shown in FIG. 8. The abscissa showed the molar ratio of transfected 4 plasmids when constructing cells; the bar graph corresponded to the left ordinate which showed the RLU value of induced virus-producing titer of each cell; the line graph corresponded to the right ordinate which showed the ratio of copy numbers of gag/pol and VSV-G fragments integrated into the cell genome, and the results were shown as follows. In EuLV-VG1 to VG5 cells, when the integrated copy number of gag/pol fragment in the cell genome reached 5.2 copies per cell and the ratio of the integrated copy number of gag/pol and VSV-G fragment in the cell genome was 2.73 (EuLV-VG2), the maximum virus-producing titer of 2.8E+06 RLU was reached. Further increasing the ratio of integrated copy number of gag/pol and VSV-G fragments will reduce the virus-producing capacity of packaging cells. Based on the results, a packaging cell line with high virus-producing titer can be obtained under the following conditions: the copy number of gag/pol fragment integrated into the cell genome was 2 to 8 copies per cell; the copy number ratio of gag/pol and VSV-G fragments integrated into the cell genome was between 1:1 and 4:1, and at least one copy of rtTA$_{3G}$-CymR and rev fragments was integrated into the cell genome; further preferably, a packaging cell line with high virus-producing titer can be obtained under the following conditions: the copy number of gag/pol fragment integrated into the cell genome was 4 to 6 copies per cell; the copy number ratio of gag/pol and VSV-G fragments integrated into the cell genome was between 2:1 and 3:1, and at least one copy of rtTA$_{3G}$-CymR and rev fragments was integrated into the cell genome.

TABLE 8

Amount of each plasmid transiently transfected during the construction of EuLV-R1 to R17 packaging cell line

| cell number | molar ratio | Transfection amount of each plasmid (μg) 19BF075 | 19BF246 | 18BF068 | 19BF131 | 19BF019 | 18BF003 | amount of total plasmid |
|---|---|---|---|---|---|---|---|---|
| R1 | 1:1:1:1 | 0.7 | 0.3 | 0.4 | 0.7 | 0.2 | 2.7 | 5.0 |
| R2 | 2:1:1:1 | 1.3 | 0.3 | 0.4 | 0.7 | 0.2 | 2.1 | 5.0 |
| R3 | 3:1:1:1 | 2.0 | 0.3 | 0.4 | 0.7 | 0.3 | 1.3 | 5.0 |
| R4 | 4:1:1:1 | 2.6 | 0.3 | 0.4 | 0.7 | 0.3 | 0.7 | 5.0 |
| R5 | 5:1:1:1 | 3.3 | 0.3 | 0.4 | 0.7 | 0.4 | 0 | 5.0 |
| R6 | 1:2:1:1 | 0.7 | 0.6 | 0.4 | 0.7 | 0.2 | 2.4 | 5.0 |
| R7 | 1:3:1:1 | 0.7 | 0.9 | 0.4 | 0.7 | 0.3 | 2 | 5.0 |
| R8 | 1:4:1:1 | 0.7 | 1.2 | 0.4 | 0.7 | 0.3 | 1.7 | 5.0 |
| R9 | 1:5:1:1 | 0.7 | 1.5 | 0.4 | 0.7 | 0.4 | 1.3 | 5.0 |
| R10 | 1:1:2:1 | 0.7 | 0.3 | 0.8 | 0.7 | 0.2 | 2.3 | 5.0 |
| R11 | 1:1:3:1 | 0.7 | 0.3 | 1.2 | 0.7 | 0.3 | 1.8 | 5.0 |
| R12 | 1:1:4:1 | 0.7 | 0.3 | 1.7 | 0.7 | 0.3 | 1.3 | 5.0 |
| R13 | 1:1:5:1 | 0.7 | 0.3 | 2.1 | 0.7 | 0.4 | 0.8 | 5.0 |
| R14 | 1:1:1:2 | 0.7 | 0.3 | 0.4 | 1.3 | 0.2 | 2.1 | 5.0 |
| R15 | 1:1:1:3 | 0.7 | 0.3 | 0.4 | 2.0 | 0.3 | 1.3 | 5.0 |
| R16 | 1:1:1:4 | 0.7 | 0.3 | 0.4 | 2.6 | 0.3 | 0.7 | 5.0 |
| R17 | 1:1:1:5 | 0.7 | 0.3 | 0.4 | 3.3 | 0.4 | 0 | 5.0 |

TABLE 9

Amount of each plasmid transiently transfected during the construction of VG1 to VG9 cell lines

| cell number | molar ratio | Transfection amount of each plasmid (μg) 19BF075 | 19BF246 | 18BF068 | 19BF131 | 19BF019 | 18BF003 | amount of total plasmid |
|---|---|---|---|---|---|---|---|---|
| VG1 | 3:3:1:12 | 0.8 | 0.4 | 0.2 | 3.2 | 0.3 | 0.1 | 5.0 |
| VG2 | 3:3:2:12 | 0.8 | 0.4 | 0.3 | 3.1 | 0.3 | 0.1 | 5.0 |
| VG3 | 3:3:3:12 | 0.8 | 0.4 | 0.5 | 3.0 | 0.4 | 0 | 5.0 |
| VG4 | 3:3:4:12 | 0.7 | 0.3 | 0.6 | 2.9 | 0.4 | 0.1 | 5.0 |
| VG5 | 3:3:5:12 | 0.7 | 0.3 | 0.8 | 2.8 | 0.4 | 0 | 5.0 |

TABLE 10

Information of primers and Taqman probe sequences

| SEQ ID NO: | name | sequence (5' to 3') | purification method | 5' modification | 3' modification |
|---|---|---|---|---|---|
| 48 | Gag-taqman-F01 | GGAGCTAGAACG ATTCGCAGTTA | PAGE | | |

TABLE 10-continued

Information of primers and Taqman probe sequences

| SEQ ID NO: | name | sequence (5' to 3') | purification method | 5' modification | 3' modification |
|---|---|---|---|---|---|
| 49 | Gag-taqman-R01 | TGATCCTGTCTG AAGGGATGGT | PAGE | | |
| 50 | Gag-Probe-01 | TCCTGGCCTGTT AGAAA | HPLC | FAM | MGB |
| 51 | Hygro-taqman-F01 | TGCTCCGCATTG GTCTTGA | PAGE | | |
| 52 | Hygro-taqman-R01 | CTTCGGACGATT GCATCACA | PAGE | | |
| 53 | Hygro-Probe-01 | ATGCTGCTTGGG CGC | HPLC | FAM | MGB |
| 54 | REV-taqman-F01 | AGGAATAGAAGA AGAAGGTGGAGA GA | PAGE | | |
| 55 | REV-taqman-R01 | GCACAGGCTCCG CAGATC | PAGE | | |
| 56 | REV-Probe-01 | ATTCGATTAGTG AACGGATC | HPLC | FAM | MGB |
| 57 | VS VG-taqman-F01 | ATTGCCCGTCAA GCTCAGAT | PAGE | | |
| 58 | VS VG-taqman-R01 | CCGTCTGCTTGA ATAGCCTTGT | PAGE | | |
| 59 | VSVG-Probe-01 | TACAAGTCAAAA TGCCCAAGAG | HPLC | FAM | MGB |

Figure 9:
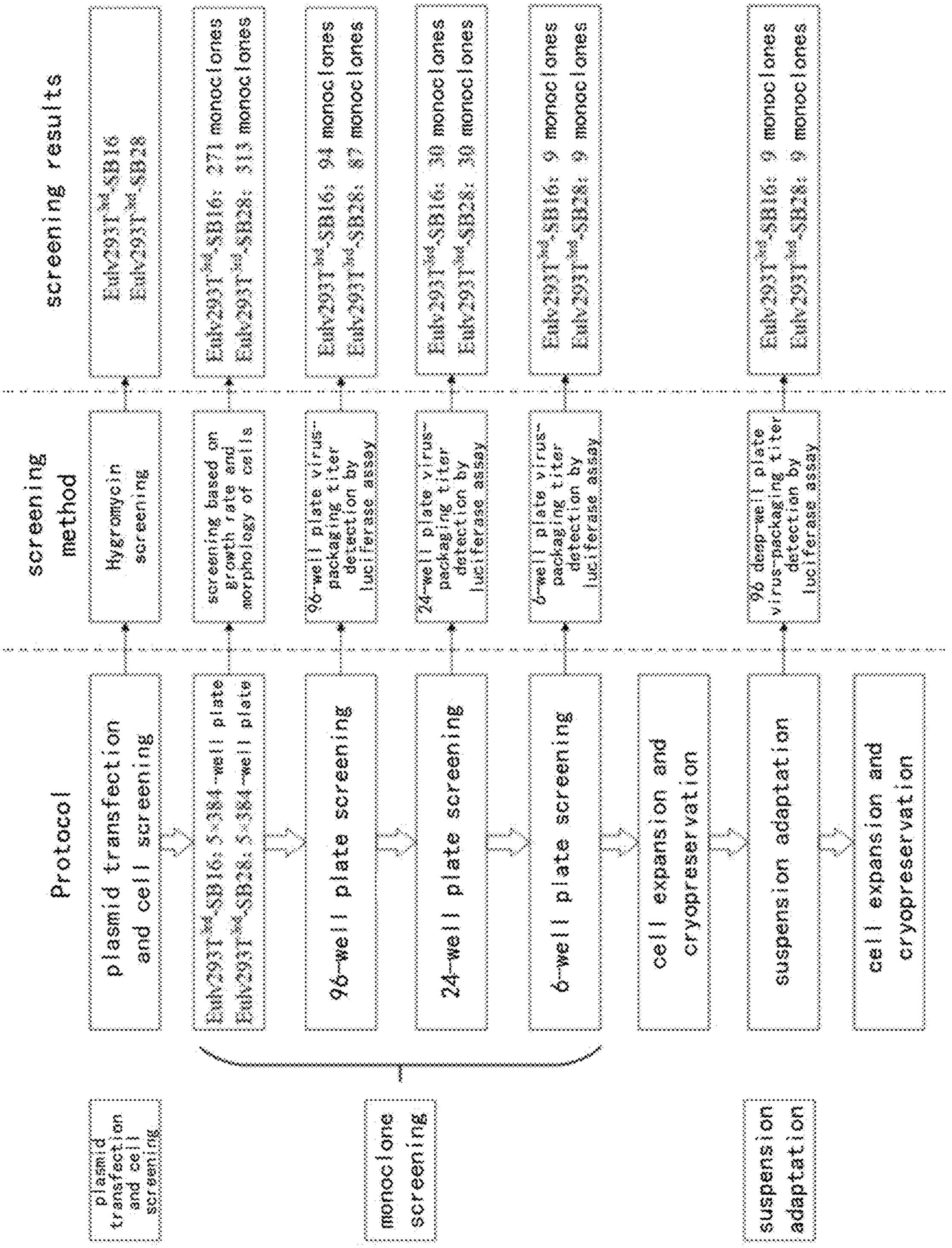
FIG. 9 is a flowchart showing the construction, screening and suspension adaptation of the EuLV293T3rd stable lentivirus packaging cell line in Example 5.

Example 5: Construction of EuLV293T3rd Lentivirus Packaging Cell Line and Screening of High-Throughput Monoclones The process of constructing EuLV293T3rd lentivirus packaging cell line was shown in FIG. 9, including three steps: plasmid transfection and cell screening, monoclonal screening, and suspension adaptation. The experimental details and results were described in detail as follows.

1. Construction of the Initial EuLV293T3rd Lentivirus Packaging Cell Line by Plasmid Transfection and Cell Line Screening The specific experimental method was as follows. Regarding the experimental procedures of cell culture, PEI transfection and hygromycin screening, please refer to Examples 2, 3 and 4.293T cells (ATCC, CRL3216) were seeded in a 60 mm dish at 1.5E+06 cells per dish and cultured at 37° C. 5% $CO_2$ for 24 hours, wherein the medium was 3 ml DMEM complete medium (Sigma, D6429) supplemented with 10% FBS (ExCell, 11H116). Plasmid transfection was performed by a PEI transfection method, wherein the amount of total plasmid was 5 μg, the mass ratio of PEI to the total plasmid was 4:1; EuLV293T3rd-SB16 cell was transfected and constructed at the molar ratio of plasmids 19BF257:19BF246:18BF067:19BF130:18BF019 being 3:3:2:12:2; EuLV293T3rd-SB28 was transfected and constructed at the molar ratio of plasmids 19BF075:19BF246:18BF068:19BF131:18BF019 being 3:3:2:12:2. After 24 hours of transfection, the cells were all seeded into a 100 mm culture dish for continuous culture, and 200 μg/ml hygromycin (Sangon Biotech A600230-0001) was added for screening. This screening pressure was maintained for at least 3 passages of subculture until the cells were stable. The judgment is based on: (1) the growth rate of the cells was the same as that of original 293T cells, (2) the SB transposase expression plasmid 18BF019 substantially disappeared in the constructed cells, which was characterized by the proportion of ECFP positive cells being reduced to less than 1%, and (3) the proportion of live cells was more than 95%. Based on the above criteria, the initial cell lines of EuLV293T3rd-SB16 (SB16 cells for short) regulated by the Tet-On single inducible expression system and EuLV293T3rd-SB28 (SB28 cells for short) regulated by the Tet-On and Cumate complex inducible expression system were obtained.

2. Screening of EuLV293T3rd-SB16 and EuLV293T3rd-SB28 High-Yielding Monoclonal Packaging Cell Line The specific experimental method was as follows. The screening process of SB16 and SB28 high-yielding monoclonal cell lines was shown in FIG. 9. First, SB16 and SB28 cells were seeded into 10 384-well plates with one cell per well by limiting dilution method for the first round of screening. The screening criteria were: (1) There was one and only one monoclonal cell; (2) The cell morphology was normal; (3) The cell growth rate was the same as that of the original 293T cell. Then, when the cells were expanded to a 96-well plate, a 24-well plate, and a 6-well plate culture system, the induced virus-producing titer of each monoclonal cell was detected by the HT1080 cell Luciferase virus titer detection method.

Figure 10:
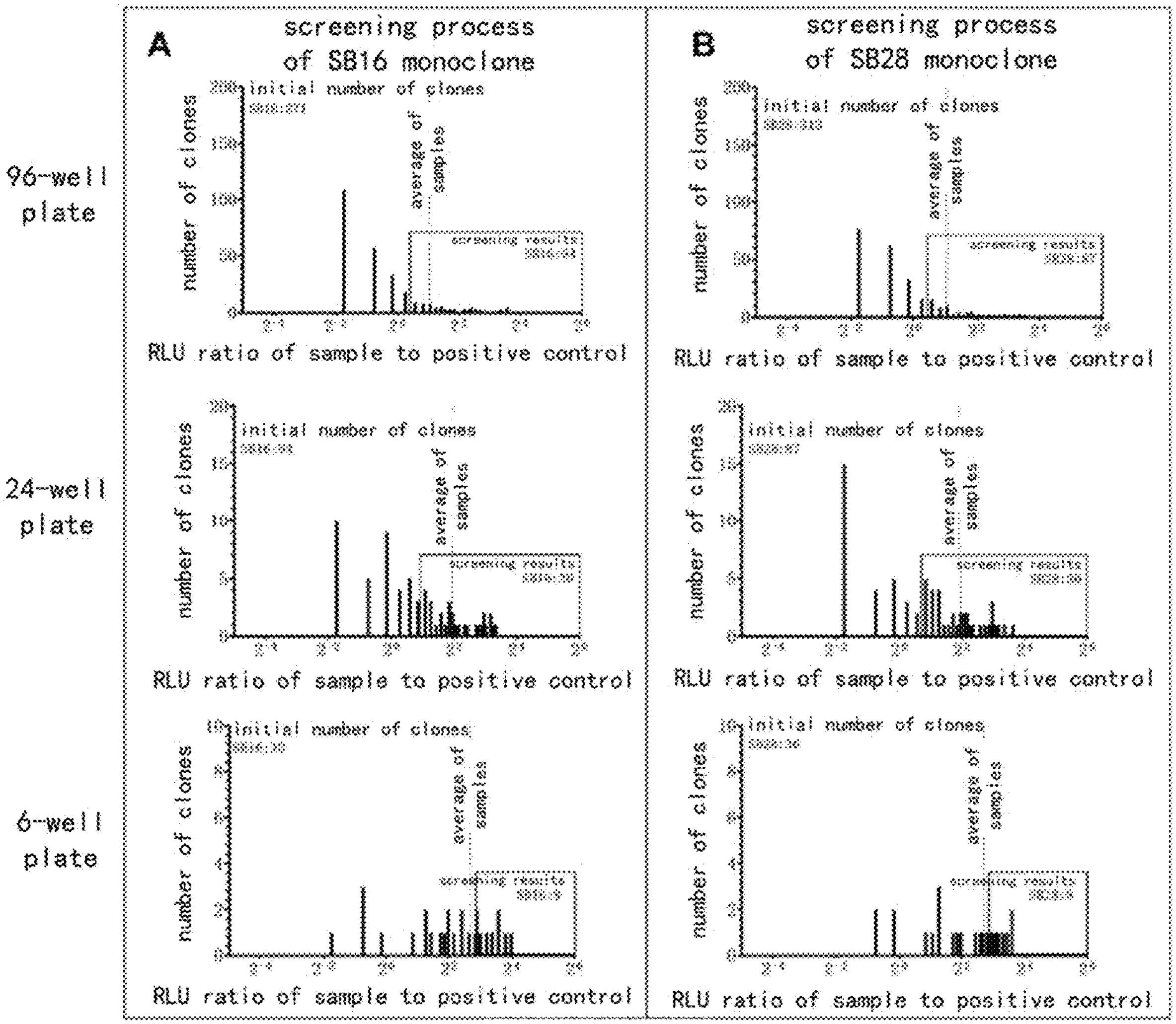
FIG. 10 shows the screening process of SB16 monoclone (FIG. 10A) and SB28 monoclone (FIG. 10B) and the screening results of 96-well plate, 24-well plate and 6-well plate in Example 5. The abscissa shows the RLU ratio of the monoclonal cell to the Luciferase standard sample (expressed as an exponent based on 2), and the ordinate shows the number of monoclonal cells in each data interval. In the figure, the dotted line shows the average value of RLU ratios for all monoclonal samples, and the box shows the monoclonal cell lines screened and obtained based on the detection results.

FIG. 10 showed the virus-producing titer ratio of the monoclonal cell to the standard sample at each screening stage. According to the HT1080 cell Luciferase virus detection method to detect the RLU value of monoclonal cell toxin production and count the number of monoclonal cells in each interval from 0 to 100,000 according to the interval of 500, the abscissa is the upper limit and standard of each interval The ratio of the RLU value of product detection (represented by the logarithm of base 2), the ordinate is the number of monoclonal cells in each statistical range. FIG. 10A showed the screening results of the SB16 cell line, and 94, 30, and 9 monoclonal cells were selected in the 96-well plate, 24-well plate and 6-well plate screening steps, respectively. FIG. 10B showed the screening result of the SB28 cell line, and 87, 30, and 9 monoclonal cells were selected in the 96-well plate, 24-well plate and 6-well plate screening steps, respectively. The specific steps of cell screening were as follows.

Regarding the 384-well plate monoclonal screening, the specific experimental steps were as follows. The SB16 and SB28 initial cells constructed above were cultured in a DMEM complete medium at 37° C. and 5% $CO_2$ to a monolayer of 70% confluence. By the limiting dilution method, cells were seeded in a 384-well plate at the density of one cell per well, and 5 384-well plates for SB16 and SB28 cells, respectively. After seeding for 2 hours until the cells adhered to the wall, sample wells with only one cell were observed and marked by an inverted microscope (Olympus IX71), and other sample wells were discarded. The medium was changed to a fresh DMEM complete medium on the 5th and 9th days after seeding; on the 10th day, the monoclonal cells with a confluence greater than 50% were seeded into a 96-well plate at 2E+04 cells per well, and a total of 271 strains of SB16 monoclonal cells and 313 strains of SB28 cells were obtained.

Regarding the 96-well plate monoclonal screening, the specific experimental steps were as follows. After culturing the cells obtained from the monoclonal screening step of 384-well plate for 24 hours, the cells were seeded at 5E+03 and 2.5E+04 cells per well in two new 96-well plates, and used for the subculture and the induced virus-producing detection of lentivirus. In the step of induced virus production of monoclonal cells, a positive control of lentivirus was prepared by transiently transfecting 293T cells, and the method was as follows: 293T cells were seeded into a 96-well plate at 2.5E+04 cells per well; after 24 hours of culture, the virus was prepared by transient transfection of plasmids via the PEI method (the total DNA amount was 0.3 μg, wherein the molar ratio of plasmid 19BF081:pMD2.G: pMDLg/PRRE:pRSV-Rev was 1:1:1:1, and the mass ratio of total DNA to PEI MAX was 1:4). 2 hours after transfection, the inducers (final concentration of 2 mmol/L sodium butyrate, 1 μg/ml DOX, 200 μg/ml Cumate) were added, and the cells were subjected to further culture for 48 hours and centrifugation at 4500 rpm for 15 minutes to collect supernatant virus. The method for inducing virus production by monoclonal cells in a 96-well plate was as follows: the above-mentioned monoclonal cells to be tested, which were seeded at 2.5E+04 cells per well in a 96-well plate, were cultured for 24 hours, and then transfection reagents were added (the amount of total DNA was 0.3 μg, wherein the amount of 19BF081 added was the same as the above positive control, the amount of remaining plasmid was made up to 0.3 μg with 18BF003, and the mass ratio of total DNA to PEI MAX was 1:4). Afterwards, the method of inducing virus production and recovering the virus supernatant was the same as the method of preparing the positive control. According to the HT1080 cell Luciferase virus titer detection method described in Example 2, the RLU value of the positive control and each sample of monoclonal cells for inducing virus production was detected. Then, according to the results of Luciferase virus titer, the monoclonal cells with RLU values higher than the positive control were selected in the order of from high RLU value to low RLU value, to obtain 87 SB16 monoclonal cells and 94 SB28 monoclonal cells.

Regarding the monoclonal screening in 24-well plate and 6-well plate, the specific experimental steps were as follows. The screening process of high-yield monoclonal cells in 24-well plate and 6-well plate was substantially the same as the aforementioned monoclonal screening in 96-well plate. During subculture, the seeding density of 24-well plate was 2E+04 cells per well, and that of 6-well plate was 2E+05 cells per well. In the step of inducing virus production of monoclonal cells, the seeding density of 24-well plate was 1E+05 cells per well, and the seeding density of 6-well plate was 8E+05 cells. When transfecting plasmids by the PEI method, the amount of total DNA per well in a 24-well plate was 1.2 μg, and that in a 6-well plate was 5 μg, and other transfection conditions such as the ratio of each plasmid and the ratio of DNA to PEI were consistent with the above experimental method. According to the results of the HT1080 cell Luciferase virus titer detection method, in the stage of monoclonal screening in 24-well plate, 30 high-yielding packaging cell lines were screened respectively from 87 SB16 and 94 SB28 monoclonal cells. In the monoclonal screening stage of 6-well plate, 9 strains of SB16 and SB28 monoclonal high-yielding packaging cells were further screened from 30 strains of cells respectively and the numbers of final screened monoclonal cells were shown in Table 11.

TABLE 11

List of high-yielding packaging cell clone numbers

| | EuLV293T$^{3rd}$-SB28 high-yielding clone number |
|---|---|
| EuLV293T$^{3rd}$-SB16-3A5 | EuLV293T$^{3rd}$-SB28-1A3 |
| EuLV293T$^{3rd}$-SB16-3C1 | EuLV293T$^{3rd}$-SB28-1C2 |
| EuLV293T$^{3rd}$-SB16-3C3 | EuLV293T$^{3rd}$-SB28-1C3 |
| EuLV293T$^{3rd}$-SB16-3C4 | EuLV293T$^{3rd}$-SB28-1C4 |
| EuLV293T$^{3rd}$-SB16-3D3 | EuLV293T$^{3rd}$-SB28-1C6 |
| EuLV293T$^{3rd}$-SB16-4A1 | EuLV293T$^{3rd}$-SB28-2B5 |
| EuLV293T$^{3rd}$-SB16-4A5 | EuLV293T$^{3rd}$-SB28-2C3 |
| EuLV293T$^{3rd}$-SB16-4B1 | EuLV293T$^{3rd}$-SB28-2C6 |
| EuLV293T$^{3rd}$-SB16-4C4 | EuLV293T$^{3rd}$-SB28-2D1 |

Figure 11:
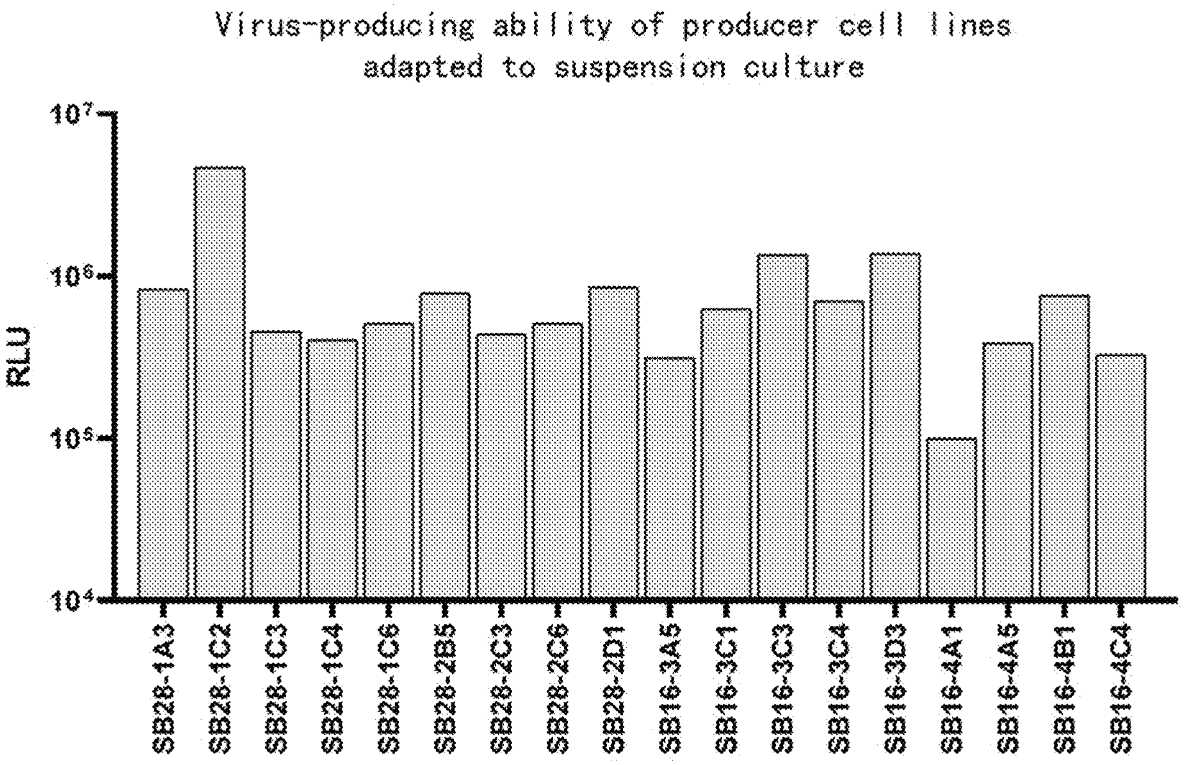
FIG. 11 shows the detection result of virus-producing ability of the monoclonal packaging cell line adapted to suspension culture via the HT1080 cell Luciferase virus titer detection method in Example 5. The abscissa shows the cell number to be detected, and the ordinate shows the RLU value of the Luciferase assay corresponding to the virus transfection titer.

3. Suspension Adaptation of High-Yielding EuLV293T3rd Monoclonal Packaging Cell and Detection of Virus-Packaging Ability The specific experimental method was as follows. The 18 strains of monoclonal cells obtained in Table 11 were seeded at 5E+05 cells/ml and 20 ml per bottle into a 125 ml shake flask (Corning 431143) for suspension adaptation, wherein the medium was Freestyle293 (Gibco®FreeStyle™ 293Expression Medium 12338018), the culture conditions were 37° C., 5% $CO_2$, and shaked with a shaking distance of 1.9 cm and a rotating speed of 140 rpm. The cells were subcultured when growing to 2.5E+06 cells/ml, and were cultured continuously until there was no obvious cell cluster and the doubling time was less than 24 hours, to obtain the suspension culture cell line of the above 18 strains of cell. The virus preparation method of the suspension cultured SB16 and SB28 cell lines was as follows. After the above cells were cultured in suspension to a density of 2.5E+06 cells/ml, the cells were harvested by centrifugation at 1000 rpm for 3 minutes, resuspended in a fresh Freestyle293 medium and adjusted to a cell density of 4E+06 cells/ml. The cell suspension was introduced to a 96-deep well plate at 0.5 ml per well, and 50 μL of PEI transfection reagent prepared in a DMEM medium was added, wherein the PEI transfection reagent contained 7.5 μg PEI MAX and 2.5 μg total DNA (containing 1 μg 18BF081 and 1.5 μg 18BF003). After mixed, the cells were further cultured on a culture shaker, and the culture conditions were 37° C., 5% $CO_2$, and shaked with a shaking distance of 1.0 cm and a rotating speed of 1000 rpm. After 2 hours, the inducers (final concentration of 2 mmol/L sodium butyrate, 1 μg/ml DOX, 200 μg/ml Cumate) were added, and the cells were subjected to further culture for 48 hours and centrifugation at 1500 rpm for 15 minutes to collect supernatant virus. Afterwards, the virus titer was detected according to the HT1080 cell Luciferase virus titer detection method as described in Example 2. The detection result was shown in FIG. 11, wherein the abscissa showed the monoclonal number, and the ordinate showed the detection result of titer, expressed in RLU. The results showed that all monoclonal cells can adapt to serum-free suspension culture conditions. The virus-producing titer of different monoclonal cells transiently transfected with 19BF081 plasmid under suspension culture conditions was 9.96E+04 to 4.68E+06 RLU, with an average titer of 8.56E+05 RLU, and a median of 5.7E+05RLU.

Example 6: Detection of Optimization Degree of EuLV293T3rd Optimal Virus-Producing Packaging Cell Line At the time of packaging the lentivirus by transient transfection of transfer-vector plasmid, the optimal virus-producing monoclonal packaging cell line screened in Example 5 was co-transformed with other expression plasmids of rev, gag/pol, and VSV-G lentivirus packaging genes regulated by a constitutively active promoter, to detect whether continuous increase of the expression of virus packaging genes can further increase the virus-producing titer of packaging cells, thereby determining whether each packaging gene fragment in the cell line reached saturation and whether the relative proportion of each virus packaging gene fragment was optimized. 6 high-yielding adherent cell lines and 5 high-yielding suspended cell lines were selected from Example 5 for the above experiment. The names and numbers of the cell lines were shown in Table 12.

TABLE 12

The numbers of EuLV293T3rd preferred high-yielding adherent cell lines and suspension cell lines

| | Numbers of adherently cultured high-yielding cell lines | numbers of suspension cultured high-yielding cell lines |
|---|---|---|
| 1 | EuLV293T3rd-SB16-3A5 | Sus-EuLV293T3rd-SB16-3C3 |
| 2 | EuLV293T3rd-SB16-3C3 | Sus-EuLV293T3rd-SB16-3D3 |
| 3 | EuLV293T3rd-SB16-4A5 | Sus-EuLV293T3rd-SB16-4A5 |
| 4 | EuLV293T3rd-SB28-1A3 | Sus-EuLV293T3rd-SB28-1A3 |
| 5 | EuLV293T3rd-SB28-1C2 | Sus-EuLV293T3rd-SB28-1C2 |
| 6 | EuLV293T3rd-SB28-2C6 | |

Figure 12:
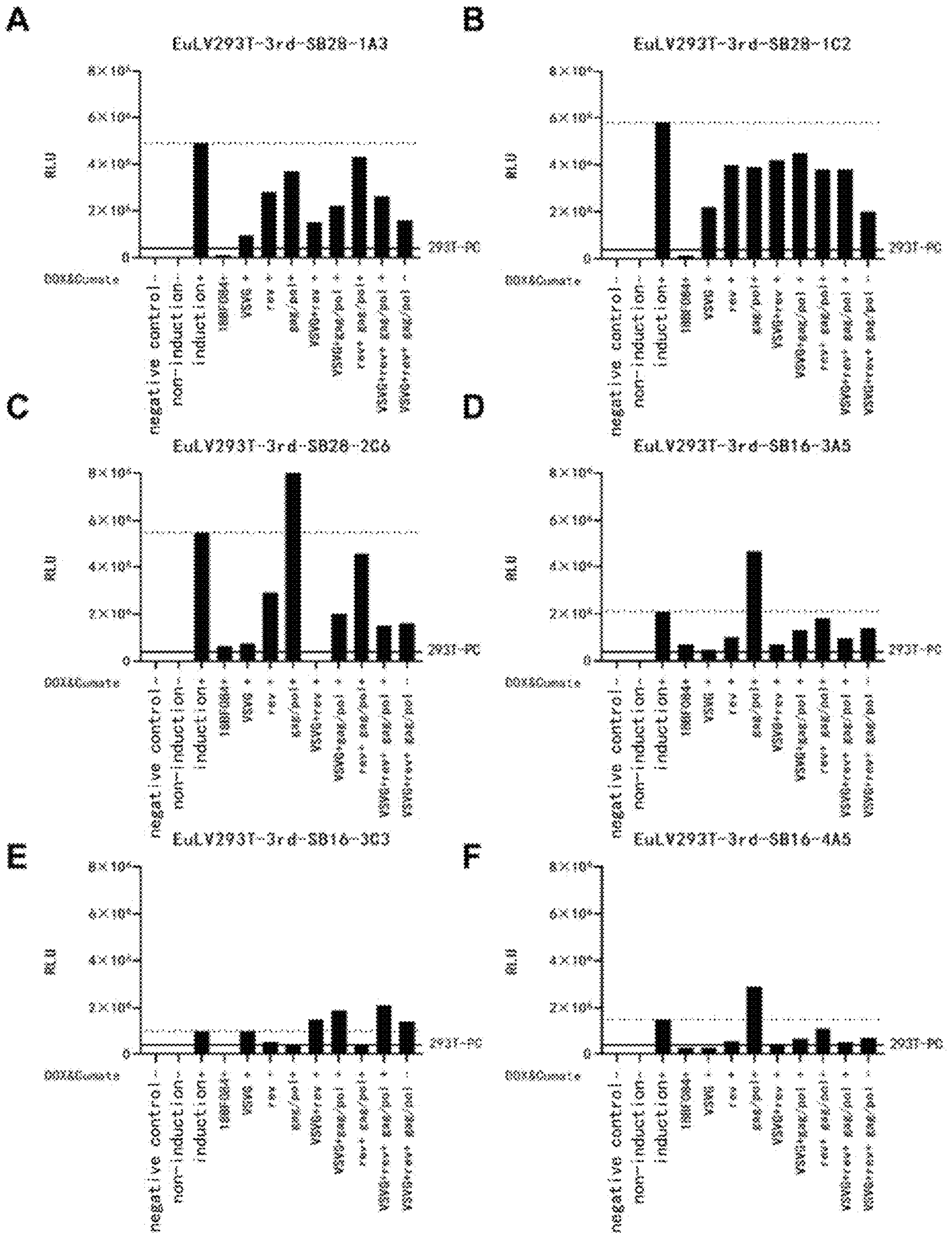
FIG. 12 shows the effect of transient transfection of different lentivirus packaging gene plasmid combinations on the virus-producing titer of adherent cultured high-yielding monoclonal packaging cell lines. The abscissa shows the combination of transiently transfected lentivirus packaging genes, wherein the "−" represents the non-induction condition, and "+" represents the induction condition; the ordinate shows the RLU value of Luciferase assay corresponding to the virus transfection titer; solid line represents the virus-producing titer of the positive control obtained by transiently transfecting 293T cells; the dotted line represents the virus-producing titer of the positive control for induced virus production by each cell.

Experiment of supplementing lentivirus packaging gene of adherently cultured high-yielding cell lines: The adherent high-yielding cell lines shown in Table 12 were cultured at 37° C., 5% $CO_2$, in a DMEM complete medium. Afterwards, each cell was seeded in different wells of a 6-well plate at 8E+05 cells per well, and transfections were performed according to the calcium phosphate transfection method in Example 2. During transfection, 200 μL of transfection reagent, containing 0.12 mol/L calcium chloride, 1×HEPES buffer, and 6.8 μg total plasmid amount, was added to each well. Table 13 showed the combination and amount of plasmids in each experimental group, wherein the 18BF084 plasmid expressed the $rtTA_{adv}$ transactivator; 19BF081 was a transfer plasmid transcribing the lentiviral genome carrying the hPGK-Luciferase-IRES-EGFP nucleic acid fragment of interest; pMD2.G (Addgene, 12259) expressed VSV-G protein; pMDLg/pRRE expressed gag and pol protein; pRSV-Rev expressed rev protein. After 6 hours of transfection, the medium was changed to a DMEM complete medium containing 5 mM sodium butyrate, and 1 μg/ml DOX and 200 μg/ml Cumate inducers were added to the samples that need to be added with inducer according to Table 13. After 48 hours of culture, the lentivirus-producing ability of each adherent cell line was detected according to the HT1080 cell Luciferase virus titer detection method as described in Example 2, and the results were shown in FIG. 12. The abscissa showed the transfection combination of plasmids in each experimental group, and the ordinate showed the RLU value of Luciferase expression in the infected HT1080 cells of corresponding experimental group. The dotted line in the figure indicated the RLU value of induced virus-producing titer of the adherent cell line only transiently transfected with the 19BF081 transfer plasmid under this condition, and the solid line in the figure showed the positive control result of 293T. The results showed that the transfection titers of the 6 packaging cells were between 9.9E+05 RLU and 5.8E+06 RLU when the lentivirus packaging genes were not supplemented. After supplementing lentivirus packaging genes such as rev, VSV-G and gag/pol, most high-yielding cell lines (such as EuLV293T3rd-SB28-1A3 and EuLV293T3rd-SB28-1C2) did not increase their virus-producing titers significantly. The cells with a greater increase in virus-producing ability were the cells with a lower initial virus-producing titer. After further supplementation of rtTA, rev, VSV-G, gag/pol single gene or multiple genes, most cell lines reduced the virus-producing titers, and only some cell lines benefited from further supplementation of gag/pol genes, indicating that the proportion of packaging genes in most of the selected cell lines has been fully optimized and further supplementation of virus packaging genes will reduce the virus-producing titer of cell lines. In addition, it also demonstrated the importance of the inserted copy number and expression level of gag/pol to the cell line virus-producing titer.

Figure 13:
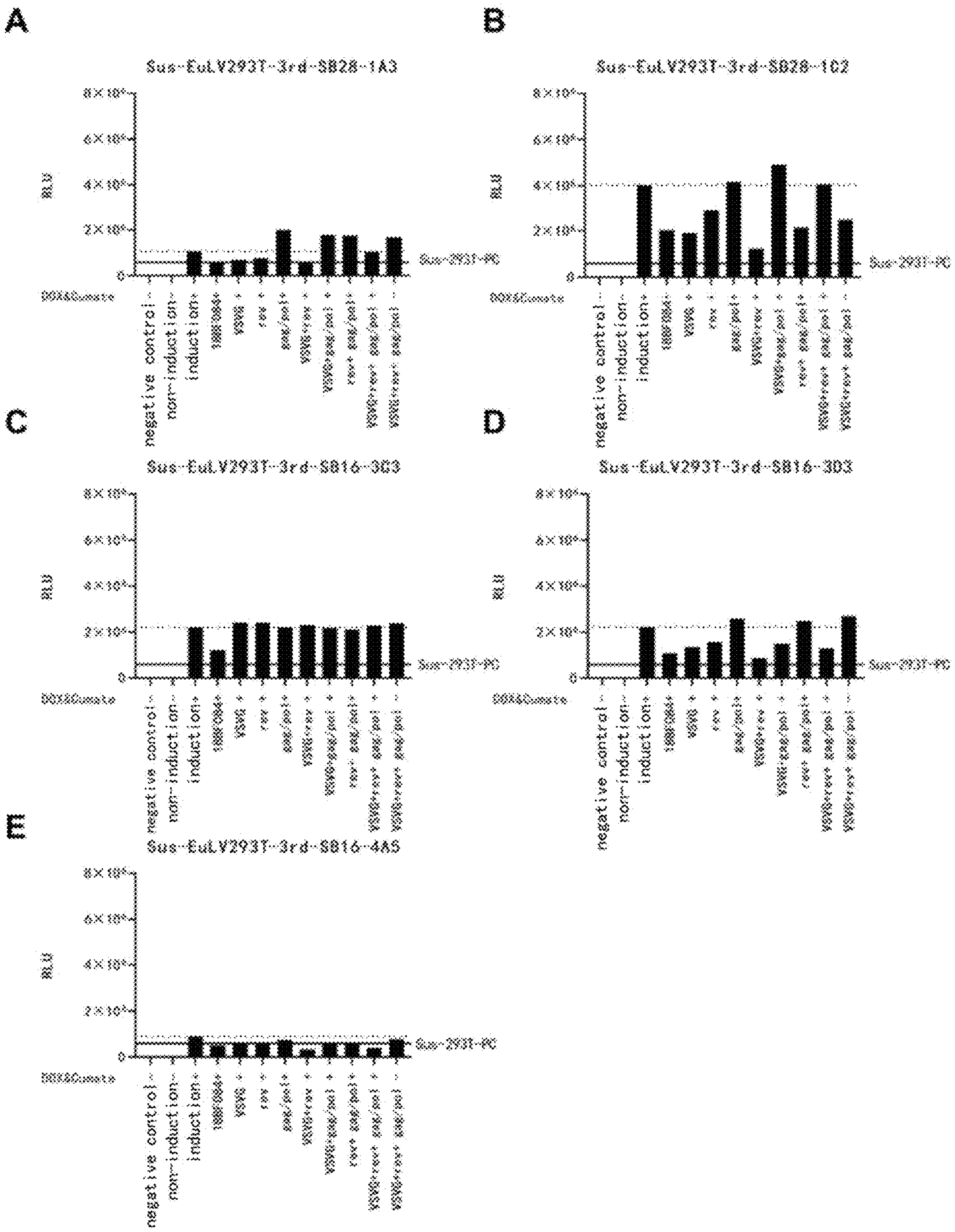
FIG. 13 shows the effect of transient transfection of different lentivirus packaging gene plasmid combinations in Example 6 on the virus-producing titer of suspension cultured high-yielding monoclonal packaging cell lines. The abscissa shows the combination of transiently transfected lentivirus packaging genes, wherein the "−" represents the non-induction condition, and "+" represents the induction condition; the ordinate shows the RLU value of Luciferase assay corresponding to the virus transfection titer; solid line represents the virus-producing titer of the positive control obtained by transiently transfecting 293T cells; the dotted line represents the virus-producing titer of the positive control for induced virus production by each cell.

Experiment of supplementing lentivirus packaging gene of suspension culture high-yielding cell lines: the suspended cell lines shown in Table 12 were cultured at 37° C., 8% $CO_2$, in the medium of FreeStyle (Gibco® FreeStyle™ 293 Expression Medium, 12338018), and shaked with a shaking distance of 1.9 cm and a rotating speed of 140 rpm. Two hours before transfection, each suspended cell line was seeded in a 96-well deep-well plate at 4E+06 cells per well with a culture volume of 1 ml. The cells were transfected according to the PEI method in Example 5, and 100 μL of transfection sample, containing 2.5 μg of total plasmid and 7.5 μg of PEI, was added to each well during transfection. The amount of plasmid added in each experimental group was shown in Table 14. After transfection, the deep-well plate was cultured in an environment with a shaking distance of 1 mm and a rotating speed of 1000 rpm/min. After 3 hours of transfection, the sodium butyrate with a final concentration of 2 mM was added, and 1 μg/ml DOX and 200 μg/ml Cumate inducers were added to the samples that need to be added with inducer according to Table 14. After 48 hours of further culture, the virus-producing ability of each suspended cell was detected according to the HT1080 cell Luciferase virus titer detection method as described in Example 2. The result was shown in FIG. 13. The abscissa showed the transfection combination of plasmids in each experimental group, and the ordinate showed the RLU value of Luciferase expression in the infected HT1080 cells of corresponding experimental group. The dotted line in the figure indicated the RLU value of induced virus-producing titer of the suspended cell line only transiently transfected with the 19BF081 transfer plasmid under this condition, and the solid line in the figure showed the positive control result of 293T. The result showed that the RLU values of the 5 suspended cell lines were between 8.9E+05 RLU and 4.0E+06 RLU when the lentivirus packaging genes were not supplemented. After supplementing lentivirus packaging genes such as rev, VSV-G and gag/pol, most high-yielding cells did not increase their virus-producing titers significantly. The cells with a greater increase in virus-producing ability were the cells with a lower initial virus-producing titer. After further supplementation of rtTA, rev, VSV-G, gag/pol single gene or multiple genes, most cell lines reduced the virus-producing titers, and only some cell lines benefited from further supplementation of gag/pol genes, indicating that the proportion of packaging genes in most of the selected cell lines has been fully optimized and further supplementation of virus packaging genes will reduce the virus-producing titer of cell lines.

TABLE 13

Names and amounts of various plasmids in each experimental group in the experiment of supplementing lentivirus packaging gene of adherently cultured high-yielding cell lines

| | experimental group | inducer DOX & Cumate | amount of transfection plasmid (μg) 18BF084 (μg) | pMD2.G (μg) | pRSV-Rev (μg) | pMDLg/pRRE (μg) | 18BF081 (μg) | 18BF003 (μg) | amount of total plasmid (μg) |
|---|---|---|---|---|---|---|---|---|---|
| 1 | negative control | − | 0.00 | 0.00 | 0.00 | 0.00 | 0.00 | 0.00 | 0.00 |
| 2 | non-induction | − | 0.00 | 0.00 | 0.00 | 0.00 | 2.26 | 4.54 | 6.80 |
| 3 | induction | + | 0.00 | 0.00 | 0.00 | 0.00 | 2.26 | 4.54 | 6.80 |
| 4 | $rtTA_{adv}$ | + | 2.26 | 0.00 | 0.00 | 0.00 | 2.26 | 2.28 | 6.80 |
| 5 | VSV-G | + | 0.00 | 0.76 | 0.00 | 0.00 | 2.26 | 3.78 | 6.80 |
| 6 | rev | + | 0.00 | 0.00 | 0.49 | 0.00 | 2.26 | 4.05 | 6.80 |
| 7 | gag/pol | + | 0.00 | 0.00 | 0.00 | 1.03 | 2.26 | 3.51 | 6.80 |
| 8 | VSV-G + rev | + | 0.00 | 0.76 | 0.49 | 0.00 | 2.26 | 3.29 | 6.80 |
| 9 | VSV-G + gag/pol | + | 0.00 | 0.76 | 0.00 | 1.03 | 2.26 | 2.75 | 6.80 |
| 10 | rev + gag/pol | + | 0.00 | 0.00 | 0.49 | 1.03 | 2.26 | 3.02 | 6.80 |
| 11 | VSV-G + rev + gag/pol | + | 0.00 | 0.76 | 0.49 | 1.03 | 2.26 | 2.26 | 6.80 |
| 12 | VSV-G + rev + gag/pol | − | 0.00 | 0.76 | 0.49 | 1.03 | 2.26 | 2.26 | 6.80 |
| 293T-PC | positive control of adherent 293T transient transfection | − | 0.00 | 1.51 | 0.97 | 2.06 | 2.26 | 0.00 | 6.80 |

TABLE 14

Names and amounts of cplasmids in each experimental group in the experiment of supplementing lentivirus packaging gene of suspension culture high-yielding cell lines

| | experimental group | inducer DOX & Cumate | amount of transfection plasmid (μg) 18BF084 (μg) | pMD2.G (μg) | pRSV-Rev (μg) | pMDLg/pRRE (μg) | 18BF081 (μg) | 18BF003 (μg) | amount of total plasmid (μg) |
|---|---|---|---|---|---|---|---|---|---|
| 1 | negative control | − | 0.00 | 0.00 | 0.00 | 0.00 | 0.00 | 0.00 | 0.00 |
| 2 | non-induction | − | 0.00 | 0.00 | 0.00 | 0.00 | 1.00 | 1.50 | 2.50 |
| 3 | induction | + | 0.00 | 0.00 | 0.00 | 0.00 | 1.00 | 1.50 | 2.50 |
| 4 | $rtTA_{adv}$ | + | 1.00 | 0.00 | 0.00 | 0.00 | 1.00 | 0.50 | 2.50 |
| 5 | VSV-G | + | 0.00 | 0.25 | 0.00 | 0.00 | 1.00 | 1.25 | 2.50 |
| 6 | rev | + | 0.00 | 0.00 | 0.15 | 0.00 | 1.00 | 1.35 | 2.50 |
| 7 | gag/pol | + | 0.00 | 0.00 | 0.00 | 0.34 | 1.00 | 1.16 | 2.50 |
| 8 | VSV-G + rev | + | 0.00 | 0.25 | 0.15 | 0.00 | 1.00 | 1.10 | 2.50 |
| 9 | VSV-G + gag/pol | + | 0.00 | 0.25 | 0.00 | 0.34 | 1.00 | 0.91 | 2.50 |
| 10 | rev + gag/pol | + | 0.00 | 0.00 | 0.15 | 0.34 | 1.00 | 1.01 | 2.50 |
| 11 | VSV-G + rev + gag/pol | + | 0.00 | 0.25 | 0.15 | 0.34 | 1.00 | 0.76 | 2.50 |
| 12 | VSV-G + rev + gag/pol | − | 0.00 | 0.25 | 0.15 | 0.34 | 1.00 | 0.76 | 2.50 |
| 293T-PC | positive control of adherent 293T transient transfection | − | 0.00 | 0.50 | 0.30 | 0.70 | 1.00 | 0.00 | 2.50 |

Example 7: Construction of a Variety of Lentivirus Producer Cell Lines Based on the High-Yielding Packaging Cell Lines EuLV293T3rd-SB16-3D3 and EuLV293T3rd-SB28-1C2

In this example, transfer-vector plasmids containing three different nucleic acid fragments of interest were stably integrated into the genomes of EuLV293T3rd-SB16-3D3 (hereinafter referred to as 3D3) and EuLV293T3rd-SB28-1C2 (hereinafter referred to as 1C2) packaging cells by the PB transposon system, and six lentivirus producer cell lines that stably produce three different lentiviruses were screened and obtained respectively. The above three transfer-vector plasmids of viral genome transcriptional cassette carrying a nucleic acid fragment of interest were: (1) 19BF081 (hPGK-Luciferase-IRES-EGFP, the length of lentiviral genome was 5.7kbp); (2) 19BF218 (the coagulation factor 8 sequence with the B protein domain deleted, CMV-BDDF8cHA-IRES-EGFP, the length of lentiviral genome was 8.5 kbp); (3) 19BF217 (the full length sequence of coagulation factor 8, CMV-F8cHA-IRES-EGFP, the length of lentiviral genome was 11.2 kbp). In order to facilitate the detection of lentivirus-producing titer of the above producer cell lines, the above nucleic acid fragments of interest were all linked with an IRES-EGFP sequence, and regarding the detailed method of constructing plasmids, please refers to Example 1. Afterwards, under adherent culture conditions, the virus-producing ability of these stable lentivirus producer cell lines was compared with that of the cells obtained by the method of transiently transfecting 293T with the same transfer plasmid to produce lentivirus. Afterwards, two types of cells constructed based on 3D3 and 1C2 and carrying the 19BF081 transfer vector were subjected to suspension culture in serum-free medium, and under such conditions, the induced virus-producing titers and the leaky virus-producing titers under non-induced conditions were detected. The method for constructing a stable lentivirus producer cell line of the present disclosure can be used to construct a stable lentivirus producer cell line carrying any nucleic acid fragment of interest.

Based on 3D3 and 1C2 cells, a producer cell line for the stable production of three different lentiviruses was constructed, and the specific steps were as follows. 3D3 and 1C2 cells were seeded in a 6-well plate at 1.5E+06 cells per well in 3 ml DMEM complete medium, cultured at 37° C. and 5% $CO_2$ for 24 hours, and then transfected by PEI method, wherein the amount of total plasmid was 5.5 ug, the molar ratio of transfer plasmid: PB transposase plasmid (18BF031) was 10:1, and the amount of total PEI was 22 ug. The transfer plasmids were 19BF081, 19BF218 and 19BF217 respectively. 24 hours after transfection, 2.5 μg/ml puromycin (Aladdin P113126) was added to screen for at least 3 passages until the cell line was stable. Six lentivirus stable producer cell lines were obtained, namely 3D3-19BF081, 3D3-19BF218, 3D3-19BF217, 1C2-19BF081, 1C2-19BF218 and 1C2-19BF217.

The virus-producing ability of cells obtained by the method of stable lentivirus producer cell line and that obtained by transient transfection method were compared, and the specific steps were as follows. The above 6 kinds of obtained cells were seeded in a 6-well plate at 8E+05 cells per well in a DMEM complete medium, and cultured at 37° C. and 5% $CO_2$ for 24 hours, and then the medium was changed to a fresh DMEM complete medium, and inducers (final concentration of 2 mmol/L sodium butyrate, 1 μg/ml DOX and 200 μg/ml Cumate) were added. After an additional 48 hours of culture, the virus supernatant was collected by centrifugation at 4500 rpm for 15 minutes. The method of preparing the virus by transiently transfecting 293T cells was the same as the method of preparing the positive control lentivirus described in Example 5, wherein the molar ratio of the transfer-vector plasmid: pMD2.G: pMDLg/PRRE: pRSV-Rev was 1:1:1:1, and the transfer-vector plasmids were 19BF081, 19BF218 and 19BF217 respectively.

Figure 14:
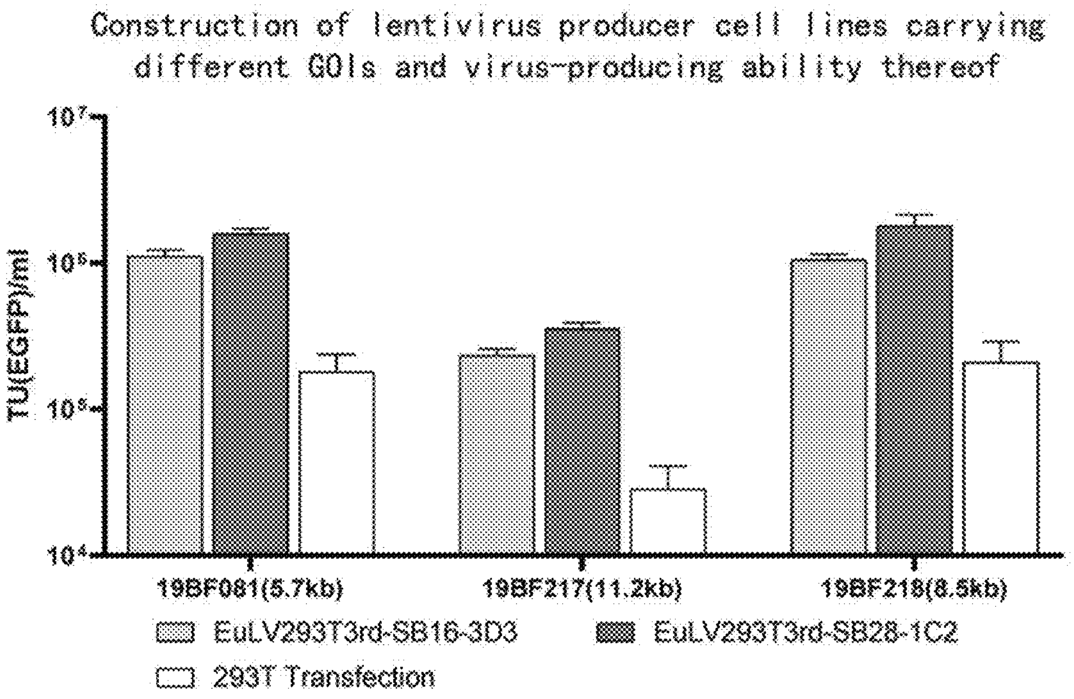
FIG. 14 shows the comparison between the virus-producing ability of the stable lentivirus producer cell line constructed in Example 7 and carrying different nucleic acid fragments of interest and the virus-producing ability obtained by transient transfection method. The abscissa shows the number of the detected transfer-vector plasmid, and the ordinate shows the RLU value of the Luciferase assay corresponding to the virus transfection titer.

The transfection titer of the above virus sample was detected based on the EGFP positive rate method of HT1080 cells, and the specific steps were as follows. HT1080 cells (ATCC CCL-121) were seeded in a 24-well plate (Corning 3524) at 5E+04 cells per well under the same culture conditions as 293T. After 24 hours, at least 3 wells were taken, digested with trypsin, and counted; the other wells were changed to 500 μL of DMEM complete medium containing 8 μg/mL polybrene (Sigma H9268). The virus solution was diluted to a variety of detection concentrations with DMEM complete medium, and then 100 μL of the diluted virus solution was added to the 24-well plate used for culturing HT1080 cells; a variety of dilution concentrations were detected for each virus sample; 100 μL of DMEM complete medium was added to the negative control, mixed, and cultured for 48 hours. Afterwards, the EGFP positive rate in each well was detected by flow cytometer (Aisen NovoCyte Flow Cytometer). A dilution with an EGFP positive rate of 15%-30% was selected to calculate the lentivirus titer according to the following formula. Lentivirus titer (TU/ml)=dilution factor×(cell count result of 24-well plate×positive rate)/0.1 ml. The experimental result was shown in FIG. 14. The results showed that the virus-producing titer by the method of stable lentivirus producer cell line was significantly higher than that by the method of transiently transfecting 293T cells. The virus-producing titers of the six final producer cell lines constructed from 3D3 and 1C2 cells constructed based on two different inducible expression strategies were all significantly higher than that of the corresponding transiently transfected 293T positive control. The virus-producing titers of the three 3D3 stable producer cell lines carrying 19BF081 (5.7 kb), 19BF217 (11.2 kb) and 19BF218 (8.5 kb) transfer vectors were 1.11E6 TU(EGFP)/ml and 2.33E5 TU(EGFP)/ml and 1.05E6 TU(EGFP)/ml, which were 6.14 times, 8.27 times and 5.01 times higher than that of the transiently transfected positive control, respectively; the virus-producing titers of the three stable 1C2 lentivirus producer cell lines carrying the above three transfer vectors were 1.59E6 TU(EGFP)/ml, 3.55E5 TU(EGFP)/ml and 1.81E6 TU(EGFP)/ml, which were 8.81 times, 12.6 times, and 8.62 times higher than that of the transiently transfected positive control. In addition, the virus-producing titer of stable lentivirus producer cell line was up to 1 order of magnitude or more higher than that of the transiently transfected control when expressing a long nucleic acid fragment of interest, and thus had a wider range of industry applications, such as constructing a lentivirus vector expressing full-length coagulation factor 8 when using gene therapy to treat hemophilia (for example, 19BF217).

Figure 15:
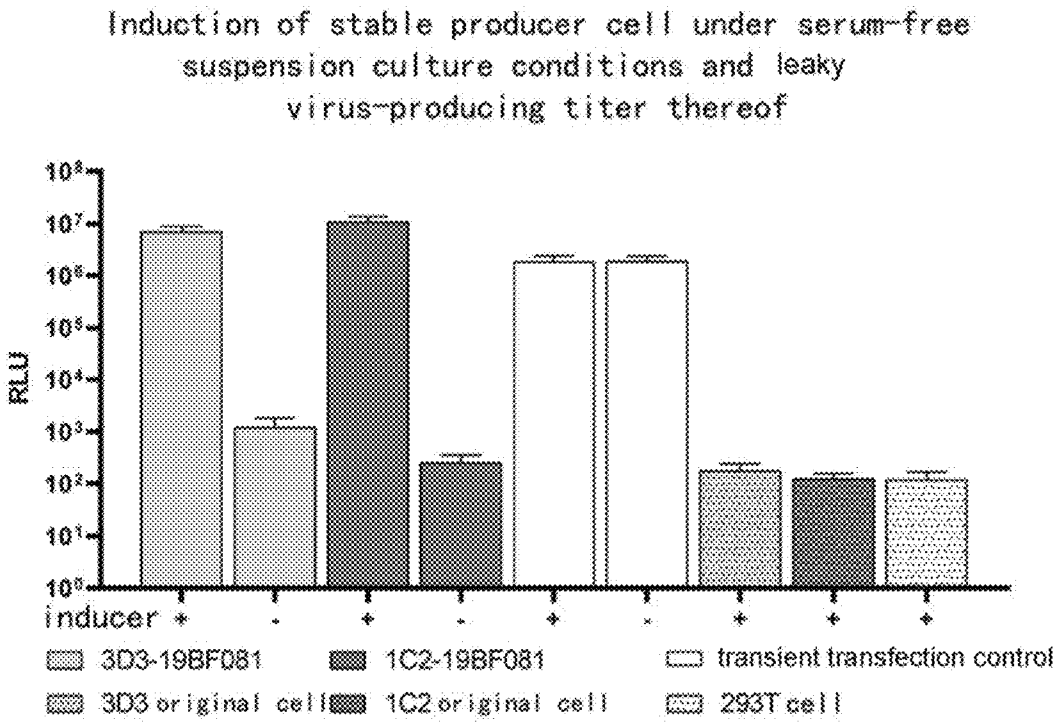
FIG. 15 shows the induced and leaky virus-producing titer of the stable lentivirus producer cells constructed in Example 7 under serum-free suspension culture conditions. The abscissa represents non-induction conditions, and "+" represents induction conditions; the ordinate shows the RLU value of the Luciferase assay corresponding to the virus transfection titer.

The virus-producing titers and leaked-virus titers of 3D3-19BF081 and 1C2-19BF081 cells under suspension culture conditions were detected, and the specific steps were as follows. According to the cell suspension adaptation method described in Example 5, 3D3-19BF081 and 1C2-19BF081 cells were adapted to suspension culture. When the suspended cells growed to 2.5E+06 cells/ml, the cells were harvested by centrifugation at 1000 rpm/min for 3 minutes, and adjusted to a cell density of 4E+06 cells/ml with a fresh Freestyle293 medium. The cell suspension was introduced to a 50 ml centrifuge tube at 5 ml/tube, and an induction group added with inducers (final concentration of 2 mmol/L sodium butyrate, 1 μg/ml DOX, 200 μg/ml Cumate) and a non-induction group added with DMEM medium were provided and cultured for 48 hours on a shaker, and then the supernatant viruses were collected by centrifugation at 4500 rpm for 15 minutes. The positive control was a virus prepared by transiently transfecting 293T cells cultured in the same suspension culture condition, and the specific steps were as follows. Plasmid transfection was performed by a PEI transfection method, wherein the amount of total plasmid was 12.5 μm, the mass ratio of PEI to the total plasmid was 4:1, and the molar ratio of plasmid 19BF081: pMD2.G: pMDLg/PRRE 1:pRSV-Rev was 1:1:1:1. After 6 hours of transfection, sodium butyrate was added at a final concentration of 2 mmol/L, and the culture was continued until the virus sample was recovered by centrifugation. Afterward, the RLU value of each sample was detected according to the HT1080 cell Luciferase virus titer detection method as described in Example 2, and the results were shown in FIG. 15. The results showed that 3D3-19BF081 and 1C2-19BF081 cells can be well adapted to the suspension culture condition, reaching a virus-producing titer of 7.08E6 RLU and 1.08E7 RLU respectively after induction, which were 3.72 times and 5.8 times than that of a virus prepared by transiently transfecting suspended 293T cells. Under non-induction conditions, the RLU fluorescence values of the leaky virus-producing titer of the two cells were substantially the same as the background RLU values of the original cells and 293T cells without the 19BF081 vector. Based on the results of this experiment, the ratios of induced/leaky virus-producing titer of 3D3-19BF081 and 1C2-19BF081 cells were 5853 times and 41646 times, respectively.

We claim:

1. A method for preparing a producer cell for producing a retroviral vector carrying a nucleic acid fragment of interest, comprising:

integrating one or more but not all of sequences of gag and pol genes of a retrovirus, a coding sequence of a viral envelope protein, and a viral genome transcriptional cassette sequence carrying the nucleic acid fragment of interest into the genome of a host cell using a Sleeping Beauty (SB) transposon system, and further integrating the remaining one or more of the sequences of gag and pol genes of the retrovirus, the coding sequence of the viral envelope protein, and the viral genome transcriptional cassette sequence carrying the nucleic acid fragment of interest into the genome of the host cell using a PiggyBac (PB) transposon system; or integrating one or more but not all of sequences of gag and pol genes of a retrovirus, a coding sequence of a viral envelope protein, and a viral genome transcriptional cassette sequence carrying the nucleic acid fragment of interest into the genome of a host cell using a PB transposon system, and further integrating the remaining one or more of the sequence of gag and pol genes of the retrovirus, the coding sequence of the viral envelope protein, and the viral genome transcriptional cassette sequence carrying the nucleic acid fragment of interest into the genome of the host cell using a SB transposon system;

controlling the transcription of i) one or more of the gag, pol and rev genes and ii) the coding sequence of the viral envelope protein, via a combination inducible expression system comprising a Tet-On inducible expression system and a Cumate inducible expression system; and independently controlling the transcription of the viral genome transcriptional cassette carrying the nucleic acid fragment of interest via a Tet-On inducible expression system.

2. The method of claim 1, wherein the retrovirus is a lentivirus, and the method comprises:

integrating one or more but not all of sequences of gag, pol and rev genes of the lentivirus, a coding sequence of a viral envelope protein, and a viral genome transcriptional cassette sequence carrying the nucleic acid fragment of interest into the genome of a host cell using an SB transposon system, and further integrating the remaining one or more of the sequences of gag, pol and rev genes of the lentivirus, the coding sequence of the viral envelope protein, and the viral genome transcriptional cassette sequence carrying the nucleic acid fragment of interest into the genome of the host cell using a PB transposon system; or integrating one or more but not all of sequences of gag, pol and rev genes of the lentivirus, a coding sequence of a viral envelope protein, and a viral genome transcriptional cassette sequence carrying the nucleic acid fragment of interest into the genome of a host cell using a PB transposon system, and further integrating the remaining one or more of the sequences of gag, pol and rev genes of the lentivirus, the coding sequence of the viral envelope protein, and the viral genome transcriptional cassette sequence carrying the nucleic acid fragment of interest into the genome of the host cell using an SB transposon system;

controlling the transcription of i) one or more of the gag, pol and rev genes and ii) the coding sequence of the viral envelope protein, via a combination inducible expression system comprising a Tet-On inducible expression system and a Cumate inducible expression system; and independently controlling the transcription of the viral genome transcriptional cassette carrying the nucleic acid fragment of interest via a Tet-On inducible expression system.

3. The method of claim 2, wherein the integrating of the sequences of gag, pol and rev genes of the lentivirus and the coding sequence of the viral envelope protein into the genome of the host cell is achieved using the SB transposon system, and the further integrating of the viral genome transcriptional cassette sequence carrying the nucleic acid fragment of interest into the genome of the host cell is achieved using the PB transposon system, or the integrating of the sequences of gag, pol and rev genes of the lentivirus and the coding sequence of the viral envelope protein into the genome of the host cell is achieved using the PB transposon system, and the further integrating of the viral genome transcriptional cassette sequence carrying the nucleic acid fragment of interest into the genome of the host cell is achieved using the SB transposon system.

4. The method of claim 2, wherein the sequences of gag, pol and rev genes of the lentivirus, the coding sequence of the viral envelope protein, and the viral genome transcriptional cassette sequence carrying the nucleic acid fragment of interest are located in two or more constructs.

5. The method of claim 4, wherein the sequences of gag and pol genes are located in a first construct, the sequence of rev gene is located in a second construct, the coding sequence of the viral envelope protein is located in a third construct, and the viral genome transcriptional cassette sequence carrying the nucleic acid fragment of interest is located in a fourth construct.

6. The method of claim 2, wherein the gag, pol, and rev genes of the lentivirus are gag, pol, and rev genes of HIV-1 virus.

7. The method of claim 2, wherein the viral envelope protein is selected from the group consisting of feline leukemia virus (RD114) envelope protein, amphotropic retrovirus envelope protein, ecotropic retrovirus envelope protein, Baboon ape leukemia virus envelope protein, nipah virus envelope protein, Mokola virus envelope protein, Lymphocytic choriomeningitis virus envelope protein, chikungunya virus envelope protein, Ross river virus envelope protein, Semliki forest virus envelope protein, Sindbis virus envelope protein, Venezuelan equine encephalitis virus envelope protein, Western equine encephalitis virus envelope protein, influenza virus envelope protein, Fowl Plague Virus envelope protein, Chandipura virus and Piry virus envelope protein, simian immunodeficiency virus envelope protein, feline immunodeficiency virus envelope protein, equine infectious anemia virus envelope protein, Ebola virus envelope protein, rabies virus envelope protein, baculovirus envelope protein, hepatitis C virus envelope protein, feline endogenous retrovirus envelope protein, measles virus envelope protein, murine leukemia virus facultative 4070A and 10A1,Gibbon ape leukemia virus envelope protein, human immunodeficiency virus gp120 and a vesicular stomatitis virus glycoprotein (VSV-G).

8. The method of claim 2, wherein the viral envelope protein is a vesicular stomatitis virus glycoprotein (VSV-G).

9. The method of claim 2, wherein SB100X is used as a transposase in the SB system, and/or ePiggyBac is used as a transposase in the PB system.

10. The method of claim 1, wherein the viral envelope protein is VSV-G, and the transcription of rev is under the control of a $TRE_{adv}$CuO sequence, a $TRE_{adv}$CuO-intron sequence, a $TRE_{3G}$ sequence, a $TRE_{3G}$CuO sequence or a $TRE_{3G}$CuO-intron sequence, and/or the transcription of the coding sequence of VSV-G is under the control of a $TRE_{adv}$CuO sequence, a $TRE_{adv}$CuO-intron sequence, a $TRE_{3G}$-intron sequence or a $TRE_{3G}$CuO-intron sequence, and/or the transcription of gag and pol is under the control of a eukaryotic promoter-intron sequence, a $TRE_{adv}$-intron sequence, a $TRE_{adv}$CuO-intron sequence, a $TRE_{3G}$-intron sequence or a $TRE_{3G}$CuO-intron sequence.

11. The method of claim 10, wherein the viral envelope protein is VSV-G, and the transcription of rev is under the control of a $TRE_{3G}$ sequence or a $TRE_{3G}$CuO sequence, and the transcription of the coding sequence of VSV-G is under the control of a $TRE_{3G}$CuO-intron sequence, and the transcription of gag and pol is under the control of a eukaryotic promoter-intron sequence or a $TRE_{3G}$CuO-intron sequence.

12. The method of claim 11, wherein the transcription of rev is under the control of a $TRE_{3G}$ sequence, and the transcription of the coding sequence of VSV-G is under the control of a $TRE_{3G}$CuO-intron sequence, and the transcription of gag and pol is under the control of a $TRE_{3G}$CuO-intron sequence; and a copy number of gag/pol gene inserted into the genome of the host cell is 2-8 copies/cell, and the ratio of the copy number of gag/pol to VSV-G inserted into the genome of the host cell is 1:1 to 4:1.

13. The method of claim 1, wherein a coding sequence of a Tet-On transactivator protein, or a coding sequence of a Tet-On transactivator protein and a coding sequence of a repressor CymR protein of Cumate operon, is/are integrated into the genome of the host cell using an SB transposon system or a PB transposon system.

14. The method of claim 13, wherein the Tet-On transactivator protein is $rtTA_{3G}$.

15. The method of claim 13, wherein the sequences of gag, pol and rev genes of the lentivirus, the coding sequence of the viral envelope protein, and the coding sequence of the Tet-On transactivator protein, or the coding sequence of the Tet-On transactivator protein and the coding sequence of the repressor CymR protein of Cumate operon are integrated into the genome of the host cell using an SB transposon system, and then the viral genome transcriptional cassette sequence carrying the nucleic acid fragment of interest is further integrated into the genome of the host cell using a PB transposon system; or the sequences of gag, pol and rev genes of the lentivirus, the coding sequence of the viral envelope protein, and the coding sequence of the Tet-On transactivator protein, or the coding sequence of the Tet-On transactivator protein and the coding sequence of the repressor CymR protein of Cumate operon are integrated into the genome of the host cell using a PB transposon system, and then the viral genome transcriptional cassette sequence carrying the nucleic acid fragment of interest is further integrated into the genome of the host cell using an SB transposon system.

* * * * *

SEQUENCE LISTING

<160> NUMBER OF SEQ ID NOS: 59

<210> SEQ ID NO 1
<211> LENGTH: 1893
<212> TYPE: DNA
<213> ORGANISM: Artificial sequence
<220> FEATURE:
<223> OTHER INFORMATION: 18BF003_pma-MCS

<400> SEQUENCE: 1

```
actgcggccg ccctgcaggt caactagtga cgtcttaatt aattgccggc tggaacgcgt     60
ttcgaacatc gattgaattc tggccaagtg gatccgctag ctctagagtc gacggtacca    120
agcttgcctc gagccatgga gatctgcatg ccctaggtcc ggaaccggtt ggcgcgccat    180
ctggcagcga tcgccgcgga acccctattt gtttattttt ctaaatacat tcaaatatgt    240
atccgctcat gagacaataa ccctgataaa tgcttcaata atattgaaaa aggaagagta    300
tgagtattca acatttccgt gtcgccctta ttcccttttt tgcggcattt tgccttcctg    360
tttttgctca cccagaaacg ctggtgaaag taaaagatgc tgaagatcag ttgggtgcac    420
gagtgggtta catcgaactg gatctcaaca gcggtaagat ccttgagagt tttcgccccg    480
aagaacgttt tccaatgatg agcactttta aagttctgct atgtggcgcg gtattatccc    540
gtattgacgc cgggcaagag caactcggtc gccgcataca ctattctcag aatgacttgg    600
ttgagtactc accagtcaca gaaaagcatc ttacggatgg catgacagta agagaattat    660
gcagtgctgc cataaccatg agtgataaca ctgcggccaa cttacttctg acaacgatcg    720
gaggaccgaa ggagctaacc gcttttttgc acaacatggg ggatcatgta actcgccttg    780
atcgttggga accggagctg aatgaagcca taccaaacga cgagcgtgac accacgatgc    840
ctgtagcaat ggcaacaacg ttgcgcaaac tattaactgg cgaactactt actctagctt    900
cccggcaaca attaatagac tggatggagg cggataaagt tgcaggacca cttctgcgct    960
cggcccttcc ggctggctgg tttattgctg ataaatctgg agccggtgag cgtgggtctc   1020
gcggtatcat tgcagcactg gggccagatg gtaagccctc ccgtatcgta gttatctaca   1080
cgacggggag tcaggcaact atggatgaac gaaatagaca gatcgctgag ataggtgcct   1140
cactgattaa gcattggtaa cgtacggaag ttagagaaaa ggcataagta gaaaagatca   1200
aaggatcttc ttgagatcct ttttttctgc gcgtaatctg ctgcttgcaa acaaaaaaac   1260
caccgctacc agcggtggtt tgtttgccgg atcaagagct accaactctt tttccgaagg   1320
taactggctt cagcagagcg cagataccaa atactgttct tctagtgtag ccgtagttag   1380
```

```
gccaccactt caagaactct gtagcaccgc ctacatacct cgctctgcta atcctgttac   1440

cagtggctgc tgccagtggc gataagtcgt gtcttaccgg gttggactca agacgatagt   1500

taccggataa ggcgcagcgg tcgggctgaa cggggggttc gtgcacacag cccagcttgg   1560

agcgaacgac ctacaccgaa ctgagatacc tacagcgtga gctatgagaa agcgccacgc   1620

ttcccgaagg gagaaaggcg gacaggtatc cggtaagcgg cagggtcgga acaggagagc   1680

gcacgaggga gcttccaggg ggaaacgcct ggtatcttta tagtcctgtc gggtttcgcc   1740

acctctgact tgagcgtcga tttttgtgat gctcgtcagg ggggcggagc ctatggaaaa   1800

acgccagcaa cgcggccttt ttacggttcc tggccttttg ctggcctttt gctcatctca   1860

tgaaaattat gcaaattgag ccagtcaggc agt                                1893
```

<210> SEQ ID NO 2
<211> LENGTH: 2900
<212> TYPE: DNA
<213> ORGANISM: Artificial sequence
<220> FEATURE:
<223> OTHER INFORMATION: NotI-IR/DR-HS4I-CMV-BGI-MCS-hGHpA-HS4I-IR/DR-AsiSI

<400> SEQUENCE: 2

```
gcggccgcat ctatacagtt gaagtcggaa gtttacatac acttaagttg gagtcattaa     60

aactcgtttt tcaactactc cacaaatttc ttgttaacaa acaatagttt tggcaagtca    120

gttaggacat ctactttgtg catgacacaa gtcatttttc caacaattgt ttacagacag    180

attatttcac ttataattca ctgtatcaca attccagtgg gtcagaagtt tacatacact    240

aagttgactg tgcctttaaa cagcttggaa aattccagaa aatgatgtca tggctttagc    300

ctgcagggag ggacagcccc cccccaaagc cccagggat gtaattacgt ccctcccccg    360

ctagggggca gcagcgagcc gcccggggct ccgctccggt ccggcgctcc ccccgcatcc    420

ccgagccggc agcgtgcggg gacagcccgg gcacggggaa ggtggcacgg gatcgctttc    480

ctctgaacgc ttctcgctgc tctttgagcc tgcagacacc tgggggggata cggggaaaag    540

gacctgcagg tcaactagtg acgtcttaat taattgccgg ctggacgtac gcgtctagtt    600

attaatagta atcaattacg gggtcattag ttcatagccc atatatggag ttccgcgtta    660

cataacttac ggtaaatggc ccgcctggct gaccgcccaa cgacccccgc ccattgacgt    720

caataatgac gtatgttccc atagtaacgc caatagggac tttccattga cgtcaatggg    780

tggagtattt acggtaaact gcccacttgg cagtacatca agtgtatcat atgccaagta    840

cgccccctat tgacgtcaat gacggtaaat ggcccgcctg gcattatgcc cagtacatga    900

ccttatggga ctttcctact tggcagtaca tctacgtatt agtcatcgct attaccatgg    960

tgatgcggtt ttggcagtac atcaatgggc gtggatagcg gtttgactca cggggatttc   1020

caagtctcca ccccattgac gtcaatggga gtttgttttg gcaccaaaat caacgggact   1080

ttccaaaatg tcgtaacaac tccgccccat tgacgcaaat gggcggtagg cgtgtacggt   1140

gggaggtcta tataagcaga gctcgtttag tgaaccgtca gatcgcctgg agacgccatc   1200

cacgctgttt tgacctccat agaagacacc gggaccgatc cagcctccgc ggattcgaat   1260

cccggccggg aacggtgcat tggaacgcgg attccccgtg ccaagagtga cgtaagtacc   1320

gcctatagag tctataggcc cacaaaaaat gctttcttct tttaatatac ttttttgttt   1380

atcttatttc taatactttc cctaatctct ttctttcagg gcaataatga tacaatgtat   1440

catgcctctt tgcaccattc taaagaataa cagtgataat ttctgggtta aggcaatagc   1500
```

```
aatatttctg catataaata tttctgcata taaattgtaa ctgatgtaag aggtttcata   1560

ttgctaatag cagctacaat ccagctacca ttctgctttt attttatggt tgggataagg   1620

ctggattatt ctgagtccaa gctaggccct tttgctaatc atgttcatac ctcttatctt   1680

cctcccacag ctcctgggca acgtgctggt ctgtgtgctg gcccatcact ttggcaaaga   1740

attgggattc gaacatcgat tgaattctgg ccaggatccg ctagctctag agtcgacggt   1800

accagtacta agcttgcctc gagccatgga gatctacggg tggcatccct gtgacccctc   1860

cccagtgcct ctcctggccc tggaagttgc cactccagtg cccaccagcc ttgtcctaat   1920

aaaattaagt tgcatcattt tgtctgacta ggtgtccttc tataatatta tggggtggag   1980

gggggtggta tggagcaagg ggcaagttgg gaagacaacc tgtagggcct gcggggtcta   2040

ttgggaacca agctggagtg cagtggcaca atcttggctc actgcaatct ccgcctcctg   2100

ggttcaagcg attctcctgc ctcagcctcc cgagttgttg ggattccagg caagcatgac   2160

caggctcagc taatttttgt tttttggta gagacggggt ttcaccatat tggccaggct   2220

ggtctccaac tcctaatctc aggtgatcta cccaccttgg cctcccaaat tgctgggatt   2280

acaggcgtga accactgctc ccttccctgt ccttgcatgc cctaggcagc tgtccggaac   2340

cggtgtttaa acaggccttt tccccgtatc cccccaggtg tctgcaggct caaagagcag   2400

cgagaagcgt tcagaggaaa gcgatcccgt gccaccttcc ccgtgcccgg gctgtccccg   2460

cacgctgccg gctcggggat gcggggggag cgcccggaccg gagcggagcc ccgggcggct   2520

cgctgctgcc ccctagcggg ggagggacgt aattacatcc ctgggggctt tggggggggg   2580

ctgtccctca ggccttggcg cgccctaaag ccatgacatc attttctgga attttccaag   2640

ctgtttaaag gcacagtcaa cttagtgtat gtaaacttct gacccactgg aattgtgata   2700

cagtgaatta taagtgaaat aatctgtctg taaacaattg ttggaaaaat gacttgtgtc   2760

atgcacaaag tagatgtcct aactgacttg ccaaaactat tgtttgttaa caagaaattt   2820

gtggagtagt tgaaaaacga gttttaatga ctccaactta agtgtatgta aacttccgac   2880

ttcaactgta tagcgatcgc                                               2900
```

<210> SEQ ID NO 3
<211> LENGTH: 1386
<212> TYPE: DNA
<213> ORGANISM: Artificial sequence
<220> FEATURE:
<223> OTHER INFORMATION: NotI-PB3'ITR-HS4I-MCS-HS4I-PB5'ITR-AsiSI

<400> SEQUENCE: 3

```
gcggccgcaa cacgcagcta gattaaccct agaaagataa tcatattgtg acgtacgtta     60

aagataatca tgcgtaaaat tgacgcatgt gttttatcgg tctgtatatc gaggtttatt    120

tattaatttg aatagatatt aagttttatt atatttacac ttacatacta ataataaatt    180

caacaaacaa tttatttatg tttatttatt tattaaaaaa aaacaaaaac tcaaaatttc    240

ttctataaag taacaaaact tttatcctgc agggagggac agcccccccc caaagccccc    300

agggatgtaa ttacgtccct cccccgctag ggggcagcag cgagccgccc ggggctccgc    360

tccggtccgg cgctcccccc gcatccccga gccggcagcg tgcggggaca gcccgggcac    420

ggggaaggtg gcacgggatc gctttcctct gaacgcttct cgctgctctt tgagcctgca    480

gacacctggg gggatacggg gaaaaggacc tgcaggtcaa ctagtgacgt cttaattaat    540

tgccggctgg acgtacgcgt tttggcaaaa tcgattgaat tctggccaag tggatccgct    600
```

```
agctctagag tcgacggtac cagtactaag cttgcctcga ggatatccca tggagatcta    660

tggggacatc atgaagcccc ttgagcatct gacttctggc taataaagga aatttatttt    720

cattgcaata gtgtgttgga atttttgtg tctctcactc ggaaggacat atgggagcat    780

gccctaggca gctgtccgga accggtgttt aaacaggcct tttccccgta tccccccagg    840

tgtctgcagg ctcaaagagc agcgagaagc gttcagagga aagcgatccc gtgccacctt    900

ccccgtgccc gggctgtccc cgcacgctgc cggctcgggg atgcgggggg agcgccggac    960

cggagcggag ccccgggcgg ctcgctgctg ccccctagcg ggggagggac gtaattacat   1020

ccctgggggc tttgggggg ggctgtccct caggccttgg cgcgccatat ctataacaag   1080

aaaatatata tataataagt tatcacgtaa gtagaacacg aaataacaat ataattatcg   1140

tatgagttaa atcttaaaag tcacgtaaaa gataatcatg cgtcattttg actcacgcgg   1200

ttgttatagt tcaaaatcag tgacacttac cgcattgaca agcacgcctc acgggagctc   1260

caagcggcga ctgagatgtc ctaaatgcac agcgacggat tcgcgctatt tagaaagaga   1320

gagcaatatt tcaagaatgc atgcgtcaat tttacgcaga ctatctttct agggttaagc   1380

gatcgc                                                              1386
```

<210> SEQ ID NO 4
<211> LENGTH: 915
<212> TYPE: DNA
<213> ORGANISM: Artificial sequence
<220> FEATURE:
<223> OTHER INFORMATION: MluI-TRE3GCuO-BGI-ClaI-EcoRI

<400> SEQUENCE: 4

```
acgcgttact ccctatcagt gatagagaac gtatgaagag tttactccct atcagtgata     60

gagaacgtat gcagacttta ctccctatca gtgatagaga acgtataagg agtttactcc    120

ctatcagtga tagagaacgt atgaccagtt tactccctat cagtgataga gaacgtatct    180

acagtttact ccctatcagt gatagagaac gtatatccag tttactccct atcagtgata    240

gagaacgtat taggcgtgta cggtgggcgc ctataaaagc agagctcgtt tagtgaaccg    300

tcagatcgcc tggagcaatt ccacatacaa acagaccaga ttgtctgttt gttacacttt    360

tgtcttatac caactttccg taccacttcc taccctcgta aattcgaatc ccggccggga    420

acggtgcatt ggaacgcgga ttccccgtgc caagagtgac gtaagtaccg cctatagagt    480

ctataggccc acaaaaaatg ctttcttctt ttaatatact tttttgttta tcttatttct    540

aatactttcc ctaatctctt tctttcaggg caataatgat acaatgtatc atgcctcttt    600

gcaccattct aaagaataac agtgataatt tctgggttaa ggcaatagca atatttctgc    660

atataaatat ttctgcatat aaattgtaac tgatgtaaga ggtttcatat tgctaatagc    720

agctacaatc cagctaccat tctgctttta ttttatggtt gggataaggc tggattattc    780

tgagtccaag ctaggccctt ttgctaatca tgttcatacc tcttatcttc ctcccacagc    840

tcctgggcaa cgtgctggtc tgtgtgctgg cccatcactt tggcaaagaa ttgggattcg    900

aaatcgattg aattc                                                     915
```

<210> SEQ ID NO 5
<211> LENGTH: 887
<212> TYPE: DNA
<213> ORGANISM: Artificial sequence
<220> FEATURE:
<223> OTHER INFORMATION: MluI-TRE3G-BGI-ClaI-EcoRI

<400> SEQUENCE: 5

```
acgcgttact ccctatcagt gatagagaac gtatgaagag tttactccct atcagtgata     60

gagaacgtat gcagacttta ctccctatca gtgatagaga acgtataagg agtttactcc    120

ctatcagtga tagagaacgt atgaccagtt tactccctat cagtgataga gaacgtatct    180

acagtttact ccctatcagt gatagagaac gtatatccag tttactccct atcagtgata    240

gagaacgtat taggcgtgta cggtgggcgc ctataaaagc agagctcgtt tagtgaaccg    300

tcagatcgcc tggagcaatt ccacaacact tttgtcttat accaactttc cgtaccactt    360

cctaccctcg taaattcgaa tcccggccgg gaacggtgca ttggaacgcg gattccccgt    420

gccaagagtg acgtaagtac cgcctataga gtctataggc ccacaaaaaa tgctttcttc    480

ttttaatata ctttttttgtt tatcttattt ctaatacttt ccctaatctc tttctttcag    540

ggcaataatg atacaatgta tcatgcctct ttgcaccatt ctaaagaata acagtgataa    600

tttctgggtt aaggcaatag caatatttct gcatataaat atttctgcat ataaattgta    660

actgatgtaa gaggtttcat attgctaata gcagctacaa tccagctacc attctgcttt    720

tattttatgg ttgggataag gctggattat tctgagtcca agctaggccc ttttgctaat    780

catgttcata cctcttatct tcctcccaca gctcctgggc aacgtgctgg tctgtgtgct    840

ggcccatcac tttggcaaag aattgggatt cgaaatcgat tgaattc                  887
```

<210> SEQ ID NO 6
<211> LENGTH: 897
<212> TYPE: DNA
<213> ORGANISM: Artificial sequence
<220> FEATURE:
<223> OTHER INFORMATION: MluI-TREadvCuO-BGI-ClaI-EcoRI

<400> SEQUENCE: 6

```
acgcgtgacg aggatcgttc gagcgagttt actccctatc agtgatagag aacgtatgtc     60

gagtttactc cctatcagtg atagagaacg atgtcgagtt tactccctat cagtgataga    120

gaacgtatgt cgagtttact ccctatcagt gatagagaac gtatgtcgag tttactccct    180

atcagtgata gagaacgtat gtcgagttta tccctatcag tgatagagaa cgtatgtcga    240

gtttactccc tatcagtgat agagaacgta tgtcgaggta ggcgtgtacg gtgggaggcc    300

tatataagca accggtgttt agtgaaccgt cagatcgcct ggagacgcca tcataataca    360

aacagaccag attgtctgtt tgttttcgaa tcccggccgg gaacggtgca ttggaacgcg    420

gattccccgt gccaagagtg acgtaagtac cgcctataga gtctataggc ccacaaaaaa    480

tgctttcttc ttttaatata ctttttttgtt tatcttattt ctaatacttt ccctaatctc    540

tttctttcag ggcaataatg atacaatgta tcatgcctct ttgcaccatt ctaaagaata    600

acagtgataa tttctgggtt aaggcaatag caatatttct gcatataaat atttctgcat    660

ataaattgta actgatgtaa gaggtttcat attgctaata gcagctacaa tccagctacc    720

attctgcttt tattttatgg ttgggataag gctggattat tctgagtcca agctaggccc    780

ttttgctaat catgttcata cctcttatct tcctcccaca gctcctgggc aacgtgctgg    840

tctgtgtgct ggcccatcac tttggcaaag aattgggatt cgaaatcgat tgaattc       897
```

<210> SEQ ID NO 7
<211> LENGTH: 852
<212> TYPE: DNA
<213> ORGANISM: Artificial sequence
<220> FEATURE:
<223> OTHER INFORMATION: MluI-TREadv-BGI-ClaI-EcoRI

<400> SEQUENCE: 7
acgcgtgacg aggatcgttc gagcgagttt actccctatc agtgatagag aacgtatgtc 60
gagtttactc cctatcagtg atagagaacg atgtcgagtt tactccctat cagtgataga 120
gaacgtatgt cgagtttact ccctatcagt gatagagaac gtatgtcgag tttactccct 180
atcagtgata gagaacgtat gtcgagttta tccctatcag tgatagagaa cgtatgtcga 240
gtttactccc tatcagtgat agagaacgta tgtcgaggta ggcgtgtacg gtgggaggcc 300
tatataagca gagctcgttt agtgaaccgt cagatcgcct tcgaatcccg gccgggaacg 360
gtgcattgga acgcggattc cccgtgccaa gagtgacgta agtaccgcct atagagtcta 420
taggcccaca aaaaatgctt tcttctttta atatactttt ttgtttatct tatttctaat 480
actttcccta atctctttct ttcagggcaa taatgataca atgtatcatg cctctttgca 540
ccattctaaa gaataacagt gataatttct gggttaaggc aatagcaata tttctgcata 600
taaatatttc tgcatataaa ttgtaactga tgtaagaggt ttcatattgc taatagcagc 660
tacaatccag ctaccattct gcttttattt tatggttggg ataaggctgg attattctga 720
gtccaagcta ggcccttttg ctaatcatgt tcatacctct tatcttcctc ccacagctcc 780
tgggcaacgt gctggtctgt gtgctggccc atcactttgg caaagaattg ggattcgaaa 840
tcgattgaat tc 852

<210> SEQ ID NO 8
<211> LENGTH: 887
<212> TYPE: DNA
<213> ORGANISM: Artificial sequence
<220> FEATURE:
<223> OTHER INFORMATION: SpeI-SV40p-optiBSD-SV40pA-PvuII-AgeI

<400> SEQUENCE: 8
actagtgtgt gtcagttagg gtgtggaaag tccccaggct ccccagcagg cagaagtatg 60
caaagcatgc atctcaatta gtcagcaacc aggtgtggaa agtccccagg ctccccagca 120
ggcagaagta tgcaaagcat gcatctcaat tagtcagcaa ccatagtccc gcccctaact 180
ccgcccatcc cgcccctaac tccgcccagt tccgcccatt ctccgcccca tggctgacta 240 attttttta tttatgcaga ggccgaggcc gcctctgcct ctgagctatt ccagaagtag 300
tgaggaggct tttttggagg ccataggctt ttgcaaaaag ctatggctaa accattgtcc 360
caagaggaaa gcaccctcat tgaaagagca actgctacaa tcaatagtat tcctatcagc 420
gaagattatt ctgtcgcttc tgctgctctc tctagtgatg gtcgtatttt tacaggtgtc 480
aatgtatatc attttacagg aggaccatgt gctgaacttg tggtgcttgg aactgcggcg 540
gcggcggcag caggcaacct gacttgtata gtcgctatcg gaaatgagaa caggggcatt 600
ttaagtccct gcggaagatg ccgacaggtg cttcttgacc tccatcctgg tatcaaagcc 660
atagtgaaag acagtgatgg acagccgacg gcagttggga ttcgtgaatt gctgccctct 720
ggttatgtgt gggagggcta aaacttgttt attgcagctt ataatggtta caaataaagc 780
aatagcatca caaatttcac aaataaagca ttttttcac tgcattctag ttgtggtttg 840
tccaaactca tcaatgtatc ttacctaggc agctgtccgg aaccggt 887

<210> SEQ ID NO 9
<211> LENGTH: 633
<212> TYPE: DNA
<213> ORGANISM: Artificial sequence
<220> FEATURE:
<223> OTHER INFORMATION: CymR coding sequence

<400> SEQUENCE: 9

```
atcgatgcca ccatgtctcc aaagaggaga acccaggcag agagggcaat ggagacacag     60
ggcaagctga tcgccgccgc cctgggcgtg ctgagggaga agggatacgc aggcttccgc    120
atcgccgatg tgccaggagc cgccggcgtg tcccggggcg cacagtctca ccacttccct    180
accaagctgg agctgctgct ggccacattt gagtggctgt atgagcagat caccgagagg    240
agccgcgcca ggctggcaaa gctgaagcca gaggacgatg tgatccagca gatgctggac    300
gatgccgccg agttctttct ggacgatgac tttagcatct ccctggatct gatcgtggcc    360
gccgatagag accccgccct gagggagggc atccagagga cagtggagag aaacaggttc    420
gtggtggagg atatgtggct gggcgtgctg gtgtctcgcg gcctgagccg ggatgacgca    480
gaggacatcc tgtggctgat ctttaacagc gtgcggggcc tggccgtgag atccctgtgg    540
cagaaggaca aggagcggtt cgagcgcgtg cggaattcca ccctggagat cgccagagag    600
aggtacgcca agtttaagag atgataactc gag                                 633
```

<210> SEQ ID NO 10
<211> LENGTH: 1496
<212> TYPE: DNA
<213> ORGANISM: Artificial sequence
<220> FEATURE:
<223> OTHER INFORMATION: SpeI-SV40p-optiHygroR-SV40pA-AgeI

<400> SEQUENCE: 10

```
actagtgtgt gtcagttagg gtgtggaaag tccccaggct ccccagcagg cagaagtatg     60
caaagcatgc atctcaatta gtcagcaacc aggtgtggaa agtccccagg ctccccagca    120
ggcagaagta tgcaaagcat gcatctcaat tagtcagcaa ccatagtccc gcccctaact    180
ccgcccatcc cgcccctaac tccgcccagt tccgcccatt ctccgcccca tggctgacta    240
atttttttta tttatgcaga ggccgaggcc gcctctgcct ctgagctatt ccagaagtag    300
tgaggaggct tttttggagg ccataggctt ttgcaaaaag ctatgaaaaa gcctgaactc    360
acagcgactt ctgttgagaa gtttctgatc gaaaagttcg acagcgttag cgacctgatg    420
cagctctcgg agggcgagga atctagggct ttcagcttcg atgtaggagg gcgtggatat    480
gtcctgcggg taaatagctg cgccgatggt ttctacaaag atcgttatgt ttatcggcac    540
tttgcatcgg ctgcgctccc gattcccgaa gtgcttgaca ttggggagtt cagcgagagc    600
ctgacctatt gcatctcccg ccgcgcacag ggcgtaactt tgcaagacct ccctgaaacc    660
gaactgcccg ctgttctaca acctgtcgcg gaggctatgg acgctattgc tgctgccgat    720
ctttcccaga cttccgggtt cggcccattt ggaccgcaag gaatcggtca atacactaca    780
tggcgtgatt tcatttgcgc gattgctgat ccccatgtgt atcattggca aactgtgatg    840
gatgataccg tcagcgcgag tgtcgcgcag gctctcgatg agctgatgct ttgggccgag    900
gattgccccg aagttcgcca cttggtccac gcggatttcg gcagcaacaa tgtcctgaca    960
gataatggcc gcataacagc ggtcattgat tggagcgaag ctatgttcgg ggattcccaa   1020
tacgaggtcg ctaacatctt tttctggcgt ccttggttgg cttgtatgga gcagcaaacg   1080
cgctactttg aaagacgaca tccagagctt gcaggatcgc ctcggctccg ggcgtatatg   1140
ctccgcattg gtcttgacca actctatcag agcttggtgg acggcaattt cgatgatgct   1200
gcttgggcgc agggtcgatg tgatgcaatc gtccgaagtg gagccgggac tgtcgggcga   1260
acacaaatcg cccgcagaag cgcagccgtc tggaccgatg gctgtgtaga agttctcgcc   1320
```

gatagtggaa acagacgccc ctctactcgt ccgagggcaa aggaatagaa cttgtttatt 1380
gcagcttata atggttacaa ataaagcaat agcatcacaa atttcacaaa taaagcattt 1440
ttttcactgc attctagttg tggtttgtcc aaactcatca atgtatctta accggt 1496

<210> SEQ ID NO 11
<211> LENGTH: 1979
<212> TYPE: DNA
<213> ORGANISM: Artificial sequence
<220> FEATURE:
<223> OTHER INFORMATION: MluI-CAGGS-BGI(C&R)-MCS-SV40pA-AgeI

<400> SEQUENCE: 11
acgcgtgaca ttgattattg acatgttatt aatagtaatc aattacgggg tcattagttc 60
atagcccata tatggagttc cgcgttacat aacttacggt aaatggcccg cctggctgac 120
cgcccaacga cccccgccca ttgacgtcaa taatgacgta tgttcccata gtaacgccaa 180
tagggacttt ccattgacgt caatgggtgg agtatttacg gtaaactgcc cacttggcag 240
tacatcaagt gtatcatatg ccaagtacgc cccctattga cgtcaatgac ggtaaatggc 300
ccgcctggca ttatgcccag tacatgacct tatgggactt tcctacttgg cagtacatct 360
acgtattagt catcgctatt accatggtcg aggtgagccc cacgttctgc ttcactctcc 420
ccatctcccc cccctcccca cccccaattt tgtatttatt tattttttaa ttattttgtg 480
cagcgatggg ggcggggggg gggggggggc gcgcgccagg cggggcgggg cggggcgagg 540
ggcggggcgg ggcgaggcgg agaggtgcgg cggcagccaa tcagagcggc gcgctccgaa 600
agtttccttt tatggcgagg cggcggcggc ggcggcccta taaaaagcga agcgcgcggc 660
gggcgttcga aggagtcgct gcgacgctgc cttcgccccg tgccccgctc cgccgccgcc 720
tcgcgccgcc cgccccggct ctgactgacc gcgttactcc cacaggtgag cgggcgggac 780
ggcccttctc ctccgggctg taattagcgc ttggtttaat gacggcttgt ttcttttctg 840
tggctgcgtg aaagccttga ggggctccgg gagggccctt tgtgcggggg gagcggctcg 900
gggggtgcgt gcgtgtgtgt gtgcgtgggg agcgccgcgt gcggctccgc gctgcccggc 960
ggctgtgagc gctgcgggcg cggcgcgggg ctttgtgcgc tccgcagtgt gcgcgagggg 1020
agcgcggccg ggggcggtgc cccgcggtgc ggggggggct gcgaggggaa caaaggctgc 1080
gtgcggggtg tgtgcgtggg ggggtgagca gggggtgtgg gcgcgtcggt cgggctgcaa 1140 cccccccctgc acccccctcc ccgagttgct gagcacggcc cggcttcggg tgcggggctc 1200
cgtacggggc gtggcgcggg gctcgccgtg ccgggcgggg ggtggcggca ggtgggggtg 1260
ccgggcgggg cggggccgcc tcgggccggg gagggctcgg gggaggggcg cggcggcccc 1320
cggagcgccg gcggctgtcg aggcgcggcg agccgcagcc attgcctttt atggtaatcg 1380
tgcgagaggg cgcagggact tcctttgtcc caaatctgtg cggagccgaa atctgggagg 1440
cgccgccgca ccccctctag cgggcgcggg gcgaagcggt gcggcgccgg caggaaggaa 1500
atgggcgggg agggccttcg tgcgtcgccg cgccgccgtc cccttctccc tctccagcct 1560
cggggctgtc cgcgggggga cggctgcctt cgggggggac ggggcagggc ggggttcggc 1620
ttctggcgtg tgaccggcgg ctcttgagcc tctgctaacc atgttcatgc cttcttcttt 1680
ttcctacagc ttcgaacctg ggcaacgtgc tggttattgt gctgtctcat cattttggca 1740
aaatcgattg aattctggcc aagtggatcc gctagctcta gagtcgacgg taccagtact 1800
aagcttgcct cgaggatatc ccatggagat ctatggggac atcatgaagc cccttgagca 1860
tctgacttct ggctaataaa ggaaatttat tttcattgca atagtgtgtt ggaatttttt 1920
gtgtctctca ctcggaagga catatgggag catgccctag gcagctgtcc ggaaccggt 1979

<210> SEQ ID NO 12
<211> LENGTH: 768
<212> TYPE: DNA
<213> ORGANISM: Artificial sequence
<220> FEATURE:
<223> OTHER INFORMATION: rtTA 3G coding sequence

<400> SEQUENCE: 12
atcgatgcca ccatgagccg cctggataag tccaaagtga tcaactctgc cctggagctg 60
ctgaatggag tgggaatcga gggactgacc acaaggaagc tggcacagaa gctgggagtg 120
gagcagccta ccctgtactg gcacgtgaag aacaagcgcg ccctgctgga cgcactgcca 180
atcgagatgc tggatcggca ccacacacac agctgcccac tggagggaga gtcctggcag 240
gattttctgc ggaacaatgc caagtcttat agatgtgcac tgctgagcca cagggacgga 300
gcaaaggtgc acctgggaac caggcccaca gagaagcagt acgagaccct ggagaaccag 360
ctggccttcc tgtgccagca gggcttttcc ctggagaatg ccctgtatgc cctgtctgcc 420
gtgggccact ttaccctggg atgcgtgctg gaggagcagg agcaccaggt ggccaaggag 480
gagagagaga caccaaccac agatagcatg ccccctctgc tgaagcaggc catcgagctg 540
ttcgacaggc agggagcaga gccagccttc ctgtttggcc tggagctgat catctgcggc 600
ctggagaagc agctgaagtg tgagtccgga ggacctacag acgcactgga cgatttcgac 660
ctggatatgc tgccagccga tgccctggac gattttgacc tggatatgct gcccgccgac 720
gccctggatg actttgacct ggacatgctg cctggctgat aactcgag 768

<210> SEQ ID NO 13
<211> LENGTH: 765
<212> TYPE: DNA
<213> ORGANISM: Artificial sequence
<220> FEATURE:
<223> OTHER INFORMATION: rtTA adv coding sequence

<400> SEQUENCE: 13
atcgatgcca ccatgtccag actggacaag agcaaagtca taaacggcgc tctggaatta 60
ctcaatggag tcggtatcga aggcctgacg acaaggaaac tcgctcaaaa gctgggagtt 120
gagcagccta ccctgtactg gcacgtgaag aacaagcggg ccctgctcga tgccctgcca 180
atcgagatgc tggacaggca tcatacccac ttctgccccc tggaaggcga gtcatggcaa 240
gactttctgc ggaacaacgc caagtcattc cgctgtgctc tcctctcaca tcgcgacggg 300
gctaaagtgc atctcggcac ccgcccaaca gagaaacagt acgaaaccct ggaaaatcag 360
ctcgcgttcc tgtgtcagca aggcttctcc ctggagaacg cactgtacgc tctgtccgcc 420
gtgggccact ttacactggg ctgcgtattg gaggaacagg agcatcaagt agcaaaagag 480
gaaagagaga cacctaccac cgattctatg cccccacttc tgagacaagc aattgagctg 540
ttcgaccggc agggagccga acctgccttc cttttcggcc tggaactaat catatgtggc 600
ctggagaaac agctaaagtg cgaaagcggc gggccggccg acgcccttga cgattttgac 660
ttagacatgc tcccagccga tgcccttgac gactttgacc ttgatatgct gcctgctgac 720
gctcttgacg attttgacct tgacatgctc cccgggtaac tcgag 765

<210> SEQ ID NO 14
<211> LENGTH: 1320
<212> TYPE: DNA

<213> ORGANISM: Artificial sequence
<220> FEATURE:
<223> OTHER INFORMATION: XhoI-IRES-ECFP-BglII

<400> SEQUENCE: 14
ctcgaggccc ctctccctcc cccccccta acgttactgg ccgaagccgc ttggaataag 60
gccggtgtgc gtttgtctat atgttatttt ccaccatatt gccgtctttt ggcaatgtga 120
gggcccggaa acctggccct gtcttcttga cgagcattcc taggggtctt tcccctctcg 180
ccaaaggaat gcaaggtctg ttgaatgtcg tgaaggaagc agttcctctg gaagcttctt 240
gaagacaaac aacgtctgta gcgacccttt gcaggcagcg gaacccccca cctggcgaca 300
ggtgcctctg cggccaaaag ccacgtgtat aagatacacc tgcaaaggcg gcacaacccc 360
agtgccacgt tgtgagttgg atagttgtgg aaagagtcaa atggctctcc tcaagcgtat 420
tcaacaaggg gctgaaggat gcccagaagg taccccattg tatgggatct gatctggggc 480
ctcggtgcac atgctttaca tgtgtttagt cgaggttaaa aaacgtcta ggccccccga 540 accacgggga cgtggttttc ctttgaaaaa cacgatgata atatggccac aaccatggtg 600
agcaagggcg aggagctgtt caccggggtg gtgcccatcc tggtcgagct ggacggcgac 660
gtaaacggcc acaagttcag cgtgtccggc gagggcgagg gcgatgccac ctacggcaag 720
ctgaccctga agttcatctg caccaccggc aagctgcccg tgccctggcc caccctcgtg 780
accaccctga cctggggcgt gcagtgcttc agccgctacc ccgaccacat gaagcagcac 840
gacttcttca agtccgccat gcccgaaggc tacgtccagg agcgcaccat cttcttcaag 900
gacgacggca actacaagac ccgcgccgag gtgaagttcg agggcgacac cctggtgaac 960
cgcatcgagc tgaagggcat cgacttcaag gaggacggca acatcctggg gcacaagctg 1020
gagtacaact acatcagcca caacgtctat atcaccgccg acaagcagaa gaacggcatc 1080
aaggccaact tcaagatccg ccacaacatc gaggacggca gcgtgcagct cgccgaccac 1140
taccagcaga acacccccat cggcgacggc cccgtgctgc tgcccgacaa ccactacctg 1200
agcacccagt ccgccctgag caaagacccc aacgagaagc gcgatcacat ggtcctgctg 1260
gagttcgtga ccgccgccgg gatcactctc ggcatggacg agctgtacaa gtaaagatct 1320

<210> SEQ ID NO 15
<211> LENGTH: 1044
<212> TYPE: DNA
<213> ORGANISM: Artificial sequence
<220> FEATURE:
<223> OTHER INFORMATION: SB transposase coding sequence

<400> SEQUENCE: 15
ggatccgcca ccatgggcaa gtccaaggag atctctcagg acctgagaaa gaggatcgtg 60
gatctgcaca agagcggcag ctccctggga gcaatctcca agcgcctggc agtgcctcgg 120
tctagcgtgc agaccatcgt gcgcaagtac aagcaccacg gcaccacaca gccttcttat 180
cggagcggcc ggagaagggt gctgagccca cgcgacgagc ggacactggt gcgcaaggtg 240
cagatcaacc cccggaccac agccaaggat ctggtgaaga tgctggagga gaccggcaca 300
aaggtgtcca tctctaccgt gaagagagtg ctgtacaggc acaacctgaa gggccactcc 360
gccagaaaga agcctctgct gcagaatagg cacaagaagg caaggctgag gttcgcaacc 420
gcacacggcg acaaggatcg cacattttgg cggaacgtgc tgtggtctga cgagaccaag 480
atcgagctgt tcggccacaa tgatcacaga tacgtgtgga ggaagaaggg cgaggcctgc 540
aagcccaaga ataccatccc tacagtgaag cacggaggag gctccatcat gctgtgggga 600

```
tgttttgcag caggaggaac aggcgccctg cacaagatcg acggcatcat ggatgccgtg    660

cagtatgtgg acatcctgaa gcagcacctg aagacctctg tgagaaagct gaagctgggc    720

aggaagtggg tgttccagca cgacaacgat ccaaagcaca caagcaaggt ggtggccaag    780

tggctgaagg acaataaggt gaaggtgctg gagtggccca gccagtcccc tgatctgaac    840

ccaatcgaga atctgtgggc cgagctgaag aagagagtga gggcccggag acccaccaac    900

ctgacacagc tgcaccagct gtgccaggag gagtgggcca agatccaccc aaattactgt    960

ggcaagctgg tggagggcta tcccaagagg ctgacccagg tgaagcagtt taagggcaac   1020

gccacaaagt attgataact cgag                                          1044
```

<210> SEQ ID NO 16
<211> LENGTH: 1806
<212> TYPE: DNA
<213> ORGANISM: Artificial sequence
<220> FEATURE:
<223> OTHER INFORMATION: PB transposase coding sequence

<400> SEQUENCE: 16

```
ggatccgcca ccatgggcag ctccctggac gatgagcaca tcctgtccgc cctgctgcag     60

tctgacgatg agctggtggg cgaggacagc gattccgagg tgagcgacca cgtgtccgag    120

gacgatgtgc agagcgacac agaggaggcc ttcatcgatg aggtgcacga ggtgcagcca    180

acctctagcg gcagcgagat cctggatgag cagaacgtga tcgagcagcc tggctcctct    240

ctggcctcca ataagatcct gaccctgcca cagaggacaa tccgcggcaa gaacaagcac    300

tgctggtcta ccagcaagcc tacacggaga tcccgggtgt ctgccctgaa ccacgtgcgg    360

tcccagagag gcccaaccag gatgtgccgc aatatctacg accccctgct gtgctttaag    420

ctgttcttta cagatgagat catcagcgag atcgtgaagt ggaccaacgc cgagatctcc    480

ctgaagaggc gcgagagcat gacctccgcc acattcaggg acaccaatga ggatgagatc    540

tacgccttct ttggcatcct ggtcatgaca gccgtgcgga aggacaacca catgagcacc    600

gacgatctgt ttgatagatc cctgtctatg gtgtacgtga gcgtgatgag cagggaccgc    660

ttcgattttc tgatccggtg cctgagaatg gacgataagt ccatccggcc tacactgaga    720

gagaatgacg tgttcacccc agtgaggaag atctgggatc tgtttatcca ccagtgtatc    780

cagaactaca caccaggagc acacctgacc atcgacgagc agctgctggg cttccggggc    840

agatgccctt ttcgcgtgta catcccaaat aagccctcta agtatggcat caagatcctg    900

atgatgtgcg atagcggcac caagtacatg atcaacggca tgccatatct gggcaggggc    960

acccagacaa atggcgtgcc cctgggcgag tactatgtga aggagctgtc caagcctgtg   1020

cacggctctt gccgcaacat cacatgtgac aattggttca cctctatccc cctggccaag   1080

aacctgctgc aggagcctta taagctgacc atcgtgggca cagtgaggag caacaagcgc   1140

gagatccccg aggtgctgaa gaatagcagg tcccgccctg tgggcacatc catgttctgc   1200

tttgatggcc cactgaccct ggtgtcttac aagcccaagc ctgccaagat ggtgtatctg   1260

ctgagctcct gtgacgagga tgcctctatc aacgagagca ccggcaagcc ccagatggtc   1320

atgtactata atcagacaaa gggcggcgtg gacaccctgg atcagatgtg cagcgtgatg   1380

acctgttccc ggaagacaaa tagatggcct atggccctgc tgtacggcat gatcaacatc   1440

gcctgcatca attctttcat catctatagc cacaacgtgt ctagcaaggg cgagaaggtg   1500

cagagcagga agaagttcat gcgcaatctg tacatgggcc tgacatcctc ttttatgcgg   1560
```

```
aagagactgg aggcccccac cctgaagagg tatctgcgcg acaacatctc caatatcctg   1620

cctaaggagg tgccaggcac ctccgacgat tctacagagg agccagtgac caagaagcgg   1680

acctactgca catattgtcc ctccaagatc cggagaaagg cctctgccag ctgcaagaag   1740

tgtaagaaag tgatctgtag agagcacaac atcgacatgt gccagtcttg tttttgataa   1800

ctcgag                                                              1806


<210> SEQ ID NO 17
<211> LENGTH: 1320
<212> TYPE: DNA
<213> ORGANISM: Artificial sequence
<220> FEATURE:
<223> OTHER INFORMATION: XhoI-IRES-EGFP-BglII

<400> SEQUENCE: 17

ctcgaggccc ctctccctcc cccccccta acgttactgg ccgaagccgc ttggaataag     60

gccggtgtgc gtttgtctat atgttatttt ccaccatatt gccgtctttt ggcaatgtga    120

gggcccggaa acctggccct gtcttcttga cgagcattcc taggggtctt tcccctctcg    180

ccaaaggaat gcaaggtctg ttgaatgtcg tgaaggaagc agttcctctg gaagcttctt    240

gaagacaaac aacgtctgta gcgacccttt gcaggcagcg gaacccccca cctggcgaca    300

ggtgcctctg cggccaaaag ccacgtgtat aagatacacc tgcaaaggcg gcacaacccc    360

agtgccacgt tgtgagttgg atagttgtgg aaagagtcaa atggctctcc tcaagcgtat    420

tcaacaaggg gctgaaggat gcccagaagg taccccattg tatgggatct gatctggggc    480

ctcggtgcac atgctttaca tgtgtttagt cgaggttaaa aaaacgtcta ggccccccga    540

accacgggga cgtggttttc ctttgaaaaa cacgatgata atatggccac aaccatggtg    600

agcaagggcg aggagctgtt caccggggtg gtgcccatcc tggtcgagct ggacggcgac    660

gtaaacggcc acaagttcag cgtgtccggc gagggcgagg gcgatgccac ctacggcaag    720

ctgaccctga agttcatctg caccaccggc aagctgcccg tgccctggcc caccctcgtg    780

accaccctga cctacggcgt gcagtgcttc agccgctacc ccgaccacat gaagcagcac    840

gacttcttca agtccgccat gcccgaaggc tacgtccagg agcgcaccat cttcttcaag    900

gacgacggca actacaagac ccgcgccgag gtgaagttcg agggcgacac cctggtgaac    960

cgcatcgagc tgaagggcat cgacttcaag gaggacggca acatcctggg gcacaagctg   1020

gagtacaact acaacagcca caacgtctat atcatggccg acaagcagaa gaacggcatc   1080

aaggtgaact tcaagatccg ccacaacatc gaggacggca gcgtgcagct cgccgaccac   1140

taccagcaga acacccccat cggcgacggc cccgtgctgc tgcccgacaa ccactacctg   1200

agcacccagt ccgccctgag caaagacccc aacgagaagc gcgatcacat ggtcctgctg   1260

gagttcgtga ccgccgccgg gatcactctc ggcatggacg agctgtacaa gtaaagatct   1320


<210> SEQ ID NO 18
<211> LENGTH: 3610
<212> TYPE: DNA
<213> ORGANISM: Artificial sequence
<220> FEATURE:
<223> OTHER INFORMATION: RSV-LTR-Gag334-RRE-cppt-MCS-WPRE-ppt-LTR-SV40p-
      optiPuroR-SV40pA

<400> SEQUENCE: 18

actagttaag tagtcttatg caatactctt gtagtcttgc aacatggtaa cgatgagtta     60

gcaacatgcc ttacaaggag agaaaaagca ccgtgcatgc cgattggtgg aagtaaggtg    120
```

```
gtacgatcgt gccttattag gaaggcaaca gacgggtctg acatggattg gacgaaccac    180
tgaattgccg cattgcagag atattgtatt taagtgccta gctcgataca taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta gaaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagaatcg atattaggag tagcacccac caaggcaaag agaagagtgg tgcagagaga    960
aaaaagagca gtgggaatag gagctttgtt ccttgggttc ttgggagcag caggaagcac   1020
tatgggcgca gcgtcaatga cgctgacggt acaggccaga caattattgt ctggtatagt   1080
gcagcagcag aacaatttgc tgagggctat tgaggcgcaa cagcatctgt tgcaactcac   1140
agtctggggc atcaagcagc tccaggcaag aatcctggct gtggaaagat acctaaagga   1200
tcaacagctc ctggggattt ggggttgctc tggaaaactc atttgcacca ctgctgtgcc   1260
ttggaatgct agttggagaa ttcttcgaac ctgcaggatg gtaccaaggc ctttttaaaa   1320
gaaaaggggg gattgggggg tacagtgcag gggaaagaat agtagacata atagcaacag   1380
acatacaaac taaagaatta caaaaacaaa ttacaaaaat tcaaaatttt gtttaaactt   1440
aattaattta aatacgcgtt gcgctagctc tagacccggg ctcgaggtcg accgggatcc   1500
gatatcatat gaatcaacct ctggattaca aaatttgtga aagattgact ggtattctta   1560
actatgttgc tccttttacg ctatgtggat acgctgcttt aatgcctttg tatcatgcta   1620
ttgcttcccg tatggctttc attttctcct ccttgtataa atcctggttg ctgtctcttt   1680
atgaggagtt gtggcccgtt gtcaggcaac gtggcgtggt gtgcactgtg tttgctgacg   1740
caacccccac tggttggggc attgccacca cctgtcagct cctttccggg actttcgctt   1800
tccccctccc tattgccacg gcggaactca tcgccgcctg ccttgcccgc tgctggacag   1860
gggctcggct gttgggcact gacaattccg tggtgttgtc ggggaagctg acgtcctttc   1920
catggctgct cgcctgtgtt gccacctgga ttctgcgcgg gacgtccttc tgctacgtcc   1980
cttcggccct caatccagcg gaccttcctt cccgcggcct gctgccggct ctgcggcctc   2040
ttccgcgtct tcgccttcgc cctcagacga gtcggatctc cctttgggcc gcctccccgc   2100
ctggcggccg cttaagacca atgacttaca aggcagctgt agatcttagc cactttttaa   2160
aagaaaaggg gggactggaa gggctaattc actcccaacg aagacaagat ctgctttttg   2220
cttgtactgg gtctctctgg ttagaccaga tctgagcctg ggagctctct ggctaactag   2280
ggaacccact gcttaagcct caataaagct tgccttgagt gcttcaagta gtgtgtgccc   2340
gtctgttgtg tgactctggt aactagagat ccctcagacc cttttagtca gtgtggaaaa   2400
tctctagcag gcgatcgcaa cttgtttatt gcagcttata atggttacaa ataaagcaat   2460
agcatcacaa atttcacaaa taaagcattt ttttcactgc attctagttg tggtttgtcc   2520
```

aaactcatca atgtatctta cctagtgtgt gtcagttagg gtgtggaaag tccccaggct 2580
ccccagcagg cagaagtatg caaagcatgc atctcaatta gtcagcaacc aggtgtggaa 2640
agtccccagg ctccccagca ggcagaagta tgcaaagcat gcatctcaat tagtcagcaa 2700
ccatagtccc gcccctaact ccgcccatcc cgcccctaac tccgcccagt tccgcccatt 2760
ctccgcccca tggctgacta attttttta tttatgcaga ggccgaggcc gcctctgcct 2820
ctgagctatt ccagaagtag tgaggaggct tttttggagg ccataggctt ttgcaaaaag 2880
ctatgactga gtacaagccc acggtgcgcc tcgccacccg cgacgatgtt cctagagccg 2940
tccgcaccct cgccgccgcg ttcgccgact accccgccac gcgccacacc gtagaccctg 3000
accgccacat cgagagggtc acagagctgc aagagctgtt tctcacgcgc gtcgggctcg 3060
acatcggcaa ggtgtgggtc gcggacgacg gcgcagcggt ggcggtctgg accacgccgg 3120
agagcgtcga agcgggggcg gtgttcgccg agatcggccc gcgcatggcc gagttgagcg 3180
gttcccggct ggccgcgcag caacagatgg agggacttct ggcaccgcac cgacccaagg 3240
agcccgcgtg gttcctggct accgtcggtg tctcgcccga ccaccagggc aagggtctgg 3300
gctccgccgt cgttctcccc ggagtggagg cagccgagag agccggggtg cccgcctttc 3360
tggaaacctc cgcgccccgc aacctcccct tctacgagcg gctcggcttc accgtcaccg 3420
ccgatgtcga ggtgcccgaa ggaccgcgta cctggtgcat gacccgcaag cccggtgcct 3480
gaaacttgtt tattgcagct tataatggtt acaaataaag caatagcatc acaaatttca 3540
caaataaagc atttttttca ctgcattcta gttgtggttt gtccaaactc atcaatgtat 3600
cttaaccggt 3610

<210> SEQ ID NO 19
<211> LENGTH: 301
<212> TYPE: DNA
<213> ORGANISM: Artificial sequence
<220> FEATURE:
<223> OTHER INFORMATION: TRE3G response element sequence

<400> SEQUENCE: 19
tccctatcag tgatagagaa cgtatgaaga gtttactccc tatcagtgat agagaacgta 60
tgcagacttt actccctatc agtgatagag aacgtataag gagtttactc cctatcagtg 120
atagagaacg tatgaccagt ttactcccta tcagtgatag agaacgtatc tacagtttac 180
tccctatcag tgatagagaa cgtatatcca gtttactccc tatcagtgat agagaacgta 240
ttaggcgtgt acggtgggcg cctataaaag cagagctcgt ttagtgaacc gtcagatcgc 300
c 301

<210> SEQ ID NO 20
<211> LENGTH: 344
<212> TYPE: DNA
<213> ORGANISM: Artificial sequence
<220> FEATURE:
<223> OTHER INFORMATION: TRE3G-CuO response element sequence

<400> SEQUENCE: 20
tccctatcag tgatagagaa cgtatgaaga gtttactccc tatcagtgat agagaacgta 60
tgcagacttt actccctatc agtgatagag aacgtataag gagtttactc cctatcagtg 120
atagagaacg tatgaccagt ttactcccta tcagtgatag agaacgtatc tacagtttac 180
tccctatcag tgatagagaa cgtatatcca gtttactccc tatcagtgat agagaacgta 240
ttaggcgtgt acggtgggcg cctataaaag cagagctcgt ttagtgaacc gtcagatcgc 300
ctggagcaat tccacataca aacagaccag attgtctgtt tgtt 344

<210> SEQ ID NO 21
<211> LENGTH: 307
<212> TYPE: DNA
<213> ORGANISM: Artificial sequence
<220> FEATURE:
<223> OTHER INFORMATION: TREadv response element sequence

<400> SEQUENCE: 21
tccctatcag tgatagagaa cgtatgtcga gtttactccc tatcagtgat agagaacgat 60
gtcgagttta ctccctatca gtgatagaga acgtatgtcg agtttactcc ctatcagtga 120
tagagaacgt atgtcgagtt tactccctat cagtgataga gaacgtatgt cgagtttatc 180
cctatcagtg atagagaacg tatgtcgagt ttactcccta tcagtgatag agaacgtatg 240
tcgaggtagg cgtgtacggt gggaggccta tataagcaga gctcgtttag tgaaccgtca 300
gatcgcc 307

<210> SEQ ID NO 22
<211> LENGTH: 352
<212> TYPE: DNA
<213> ORGANISM: Artificial sequence
<220> FEATURE:
<223> OTHER INFORMATION: TREadv-CuO response element sequence

<400> SEQUENCE: 22
tccctatcag tgatagagaa cgtatgtcga gtttactccc tatcagtgat agagaacgat 60
gtcgagttta ctccctatca gtgatagaga acgtatgtcg agtttactcc ctatcagtga 120
tagagaacgt atgtcgagtt tactccctat cagtgataga gaacgtatgt cgagtttatc 180
cctatcagtg atagagaacg tatgtcgagt ttactcccta tcagtgatag agaacgtatg 240
tcgaggtagg cgtgtacggt gggaggccta tataagcaac cggtgtttag tgaaccgtca 300
gatcgcctgg agacgccatc ataatacaaa cagaccagat tgtctgtttg tt 352

<210> SEQ ID NO 23
<211> LENGTH: 231
<212> TYPE: DNA
<213> ORGANISM: Artificial sequence
<220> FEATURE:
<223> OTHER INFORMATION: SB IR/DR sequence

<400> SEQUENCE: 23
ttagtgtatg taaacttctg acccactgga attgtgatac agtgaattat aagtgaaata 60
atctgtctgt aaacaattgt tggaaaaatg acttgtgtca tgcacaaagt agatgtccta 120
actgacttgc caaaactatt gtttgttaac aagaaatttg tggagtagtt gaaaaacgag 180
ttttaatgac tccaacttaa gtgtatgtaa acttccgact tcaactgtat a 231

<210> SEQ ID NO 24
<211> LENGTH: 238
<212> TYPE: DNA
<213> ORGANISM: Artificial sequence
<220> FEATURE:
<223> OTHER INFORMATION: PB 3'ITR

<400> SEQUENCE: 24
ccctagaaag ataatcatat tgtgacgtac gttaaagata atcatgcgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaaacaa aaactcaaaa tttcttctat aaagtaacaa aacttttta 238

<210> SEQ ID NO 25
<211> LENGTH: 313
<212> TYPE: DNA
<213> ORGANISM: Artificial sequence
<220> FEATURE:
<223> OTHER INFORMATION: PB 5'ITR

<400> SEQUENCE: 25
catatctata acaagaaaat atatatataa taagttatca cgtaagtaga acacgaaata 60
acaatataat tatcgtatga gttaaatctt aaaagtcacg taaaagataa tcatgcgtca 120
ttttgactca cgcggttgtt atagttcaaa atcagtgaca cttaccgcat tgacaagcac 180
gcctcacggg agctccaagc ggcgactgag atgtcctaaa tgcacagcga cggattcgcg 240
ctatttagaa agagagagca atatttcaag aatgcatgcg tcaattttac gcagactatc 300
tttctagggt taa 313

<210> SEQ ID NO 26
<211> LENGTH: 488
<212> TYPE: DNA
<213> ORGANISM: Artificial sequence
<220> FEATURE:
<223> OTHER INFORMATION: BGI intron sequence

<400> SEQUENCE: 26
tcccggccgg gaacggtgca ttggaacgcg gattccccgt gccaagagtg acgtaagtac 60
cgcctataga gtctataggc ccacaaaaaa tgctttcttc ttttaatata cttttttgtt 120
tatcttattt ctaatacttt ccctaatctc tttctttcag ggcaataatg atacaatgta 180
tcatgcctct ttgcaccatt ctaaagaata acagtgataa tttctgggtt aaggcaatag 240
caatatttct gcatataaat atttctgcat ataaattgta actgatgtaa gaggtttcat 300
attgctaata gcagctacaa tccagctacc attctgcttt tattttatgg ttgggataag 360
gctggattat tctgagtcca agctaggccc ttttgctaat catgttcata cctcttatct 420
tcctcccaca gctcctgggc aacgtgctgg tctgtgtgct ggcccatcac tttggcaaag 480
aattggga 488

<210> SEQ ID NO 27
<211> LENGTH: 612
<212> TYPE: DNA
<213> ORGANISM: Artificial sequence
<220> FEATURE:
<223> OTHER INFORMATION: CymR encoding nucleic acid sequence

<400> SEQUENCE: 27
atgtctccaa agaggagaac ccaggcagag agggcaatgg agacacaggg caagctgatc 60
gccgccgccc tgggcgtgct gagggagaag ggatacgcag gcttccgcat cgccgatgtg 120
ccaggagccg ccggcgtgtc ccggggcgca cagtctcacc acttccctac caagctggag 180
ctgctgctgg ccacatttga gtggctgtat gagcagatca ccgagaggag ccgcgccagg 240
ctggcaaagc tgaagccaga ggacgatgtg atccagcaga tgctggacga tgccgccgag 300
ttctttctgg acgatgactt tagcatctcc ctggatctga tcgtggccgc cgatagagac 360
cccgccctga gggagggcat ccagaggaca gtggagagaa acaggttcgt ggtggaggat 420
atgtggctgg gcgtgctggt gtctcgcggc ctgagccggg atgacgcaga ggacatcctg 480
tggctgatct ttaacagcgt gcggggcctg gccgtgagat ccctgtggca gaaggacaag 540
gagcggttcg agcgcgtgcg gaattccacc ctggagatcg ccagagagag gtacgccaag 600
tttaagagat ga 612

<210> SEQ ID NO 28
<211> LENGTH: 747
<212> TYPE: DNA
<213> ORGANISM: Artificial sequence
<220> FEATURE:
<223> OTHER INFORMATION: rtTA3G encoding nucleic acid sequence

<400> SEQUENCE: 28
atgagccgcc tggataagtc caaagtgatc aactctgccc tggagctgct gaatggagtg 60
ggaatcgagg gactgaccac aaggaagctg gcacagaagc tgggagtgga gcagcctacc 120
ctgtactggc acgtgaagaa caagcgcgcc ctgctggacg cactgccaat cgagatgctg 180
gatcggcacc acacacacag ctgcccactg gagggagagt cctggcagga ttttctgcgg 240
aacaatgcca agtcttatag atgtgcactg ctgagccaca gggacggagc aaaggtgcac 300
ctgggaacca ggcccacaga gaagcagtac gagaccctgg agaaccagct ggccttcctg 360
tgccagcagg gcttttccct ggagaatgcc ctgtatgccc tgtctgccgt gggccacttt 420
accctgggat gcgtgctgga ggagcaggag caccaggtgg ccaaggagga gagagagaca 480
ccaaccacag atagcatgcc ccctctgctg aagcaggcca tcgagctgtt cgacaggcag 540
ggagcagagc cagccttcct gtttggcctg gagctgatca tctgcggcct ggagaagcag 600
ctgaagtgtg agtccggagg acctacagac gcactggacg atttcgacct ggatatgctg 660
ccagccgatg ccctggacga ttttgacctg gatatgctgc ccgccgacgc cctggatgac 720
tttgacctgg acatgctgcc tggctga 747

<210> SEQ ID NO 29
<211> LENGTH: 747
<212> TYPE: DNA
<213> ORGANISM: Artificial sequence
<220> FEATURE:
<223> OTHER INFORMATION: rtTAadv encoding nucleic acid sequence

<400> SEQUENCE: 29
atgtccagac tggacaagag caaagtcata aacggcgctc tggaattact caatggagtc 60
ggtatcgaag gcctgacgac aaggaaactc gctcaaaagc tgggagttga gcagcctacc 120
ctgtactggc acgtgaagaa caagcgggcc ctgctcgatg ccctgccaat cgagatgctg 180
gacaggcatc atacccactt ctgccccctg gaaggcgagt catggcaaga ctttctgcgg 240
aacaacgcca agtcattccg ctgtgctctc ctctcacatc gcgacggggc taaagtgcat 300
ctcggcaccc gcccaacaga gaaacagtac gaaaccctgg aaaatcagct cgcgttcctg 360
tgtcagcaag gcttctccct ggagaacgca ctgtacgctc tgtccgccgt gggccacttt 420
acactgggct gcgtattgga ggaacaggag catcaagtag caaaagagga aagagagaca 480
cctaccaccg attctatgcc cccacttctg agacaagcaa ttgagctgtt cgaccggcag 540
ggagccgaac ctgccttcct tttcggcctg gaactaatca tatgtggcct ggagaaacag 600
ctaaagtgcg aaagcggcgg gccggccgac gcccttgacg attttgactt agacatgctc 660
ccagccgatg cccttgacga ctttgacctt gatatgctgc ctgctgacgc tcttgacgat 720
tttgaccttg acatgctccc cgggtaa 747

<210> SEQ ID NO 30
<211> LENGTH: 1023
<212> TYPE: DNA
<213> ORGANISM: Artificial sequence
<220> FEATURE:
<223> OTHER INFORMATION: SB transposase encoding nucleic acid sequence

<400> SEQUENCE: 30
atgggcaagt ccaaggagat ctctcaggac ctgagaaaga ggatcgtgga tctgcacaag 60
agcggcagct ccctgggagc aatctccaag cgcctggcag tgcctcggtc tagcgtgcag 120
accatcgtgc gcaagtacaa gcaccacggc accacacagc cttcttatcg gagcggccgg 180
agaagggtgc tgagcccacg cgacgagcgg acactggtgc gcaaggtgca gatcaacccc 240
cggaccacag ccaaggatct ggtgaagatg ctggaggaga ccggcacaaa ggtgtccatc 300
tctaccgtga agagagtgct gtacaggcac aacctgaagg gccactccgc cagaaagaag 360
cctctgctgc agaataggca caagaaggca aggctgaggt tcgcaaccgc acacggcgac 420
aaggatcgca cattttggcg gaacgtgctg tggtctgacg agaccaagat cgagctgttc 480
ggccacaatg atcacagata cgtgtggagg aagaagggcg aggcctgcaa gcccaagaat 540
accatcccta cagtgaagca cggaggaggc tccatcatgc tgtggggatg ttttgcagca 600
ggaggaacag gcgccctgca caagatcgac ggcatcatgg atgccgtgca gtatgtggac 660
atcctgaagc agcacctgaa gacctctgtg agaaagctga agctgggcag gaagtgggtg 720
ttccagcacg acaacgatcc aaagcacaca agcaaggtgg tggccaagtg gctgaaggac 780
aataaggtga aggtgctgga gtggcccagc cagtcccctg atctgaaccc aatcgagaat 840
ctgtgggccg agctgaagaa gagagtgagg gcccggagac ccaccaacct gacacagctg 900
caccagctgt gccaggagga gtgggccaag atccacccaa attactgtgg caagctggtg 960
gagggctatc ccaagaggct gacccaggtg aagcagttta agggcaacgc cacaaagtat 1020
tga 1023

<210> SEQ ID NO 31
<211> LENGTH: 1785
<212> TYPE: DNA
<213> ORGANISM: Artificial sequence
<220> FEATURE:
<223> OTHER INFORMATION: PB transposase encoding nucleic acid sequence

<400> SEQUENCE: 31
atgggcagct ccctggacga tgagcacatc ctgtccgccc tgctgcagtc tgacgatgag 60
ctggtgggcg aggacagcga ttccgaggtg agcgaccacg tgtccgagga cgatgtgcag 120
agcgacacag aggaggcctt catcgatgag gtgcacgagg tgcagccaac ctctagcggc 180
agcgagatcc tggatgagca gaacgtgatc gagcagcctg gctcctctct ggcctccaat 240
aagatcctga ccctgccaca gaggacaatc cgcggcaaga acaagcactg ctggtctacc 300
agcaagccta cacggagatc ccgggtgtct gccctgaacc acgtgcggtc ccagagaggc 360
ccaaccagga tgtgccgcaa tatctacgac cccctgctgt gctttaagct gttctttaca 420
gatgagatca tcagcgagat cgtgaagtgg accaacgccg agatctccct gaagaggcgc 480
gagagcatga cctccgccac attcagggac accaatgagg atgagatcta cgccttcttt 540
ggcatcctgg tcatgacagc cgtgcggaag gacaaccaca tgagcaccga cgatctgttt 600
gatagatccc tgtctatggt gtacgtgagc gtgatgagca gggaccgctt cgattttctg 660

```
atccggtgcc tgagaatgga cgataagtcc atccggccta cactgagaga gaatgacgtg    720

ttcaccccag tgaggaagat ctgggatctg tttatccacc agtgtatcca gaactacaca    780

ccaggagcac acctgaccat cgacgagcag ctgctgggct tccggggcag atgccctttt    840

cgcgtgtaca tcccaaataa gccctctaag tatggcatca agatcctgat gatgtgcgat    900

agcggcacca agtacatgat caacggcatg ccatatctgg gcaggggcac ccagacaaat    960

ggcgtgcccc tgggcgagta ctatgtgaag gagctgtcca agcctgtgca cggctcttgc   1020

cgcaacatca catgtgacaa ttggttcacc tctatccccc tggccaagaa cctgctgcag   1080

gagccttata agctgaccat cgtgggcaca gtgaggagca acaagcgcga gatccccgag   1140

gtgctgaaga atagcaggtc ccgccctgtg ggcacatcca tgttctgctt tgatggccca   1200

ctgaccctgg tgtcttacaa gcccaagcct gccaagatgg tgtatctgct gagctcctgt   1260

gacgaggatg cctctatcaa cgagagcacc ggcaagcccc agatggtcat gtactataat   1320

cagacaaagg gcggcgtgga caccctggat cagatgtgca gcgtgatgac ctgttcccgg   1380

aagacaaata gatggcctat ggccctgctg tacggcatga tcaacatcgc ctgcatcaat   1440

tctttcatca tctatagcca caacgtgtct agcaagggcg agaaggtgca gagcaggaag   1500

aagttcatgc gcaatctgta catgggcctg acatcctctt ttatgcggaa gagactggag   1560

gcccccaccc tgaagaggta tctgcgcgac aacatctcca atatcctgcc taaggaggtg   1620

ccaggcacct ccgacgattc tacagaggag ccagtgacca agaagcggac ctactgcaca   1680

tattgtccct ccaagatccg gagaaaggcc tctgccagct gcaagaagtg taagaaagtg   1740

atctgtagag agcacaacat cgacatgtgc cagtcttgtt tttga                   1785
```

<210> SEQ ID NO 32
<211> LENGTH: 38
<212> TYPE: DNA
<213> ORGANISM: Artificial sequence
<220> FEATURE:
<223> OTHER INFORMATION: C-VSVG-F

<400> SEQUENCE: 32

```
gctcatcgat gccaccatga agtgcctttt gtacttag                             38
```

<210> SEQ ID NO 33
<211> LENGTH: 35
<212> TYPE: DNA
<213> ORGANISM: Artificial sequence
<220> FEATURE:
<223> OTHER INFORMATION: C-VSVG-R

<400> SEQUENCE: 33

```
caggctcgag ctattacttt ccaagtcggt tcatc                                35
```

<210> SEQ ID NO 34
<211> LENGTH: 34
<212> TYPE: DNA
<213> ORGANISM: Artificial sequence
<220> FEATURE:
<223> OTHER INFORMATION: C-rev-F

<400> SEQUENCE: 34

```
cgatatcgat gccaccatgg caggaagaag cgga                                 34
```

<210> SEQ ID NO 35
<211> LENGTH: 34
<212> TYPE: DNA
<213> ORGANISM: Artificial sequence
<220> FEATURE:
<223> OTHER INFORMATION: C-rev-R

<400> SEQUENCE: 35
catgctcgag ttactattct ttagctcctg actc 34

<210> SEQ ID NO 36
<211> LENGTH: 29
<212> TYPE: DNA
<213> ORGANISM: Artificial sequence
<220> FEATURE:
<223> OTHER INFORMATION: C-RRE-F

<400> SEQUENCE: 36
catggatcta gaaggagctt tgttccttg 29

<210> SEQ ID NO 37
<211> LENGTH: 33
<212> TYPE: DNA
<213> ORGANISM: Artificial sequence
<220> FEATURE:
<223> OTHER INFORMATION: C-RRE-R

<400> SEQUENCE: 37
caggctcgag aagcttgtgt aattgttaat ttc 33

<210> SEQ ID NO 38
<211> LENGTH: 33
<212> TYPE: DNA
<213> ORGANISM: Artificial sequence
<220> FEATURE:
<223> OTHER INFORMATION: C-GagPol-F

<400> SEQUENCE: 38
gcacgaattc gccaccatgg gtgcgagagc gtc 33

<210> SEQ ID NO 39
<211> LENGTH: 36
<212> TYPE: DNA
<213> ORGANISM: Artificial sequence
<220> FEATURE:
<223> OTHER INFORMATION: C-GagPol-R

<400> SEQUENCE: 39
gcagtctaga ctattaatcc tcatcctgtc tacttg 36

<210> SEQ ID NO 40
<211> LENGTH: 29
<212> TYPE: DNA
<213> ORGANISM: Artificial sequence
<220> FEATURE:
<223> OTHER INFORMATION: hPGK-F

<400> SEQUENCE: 40
catacgcgtg cttgatatcg aattccacg 29

<210> SEQ ID NO 41
<211> LENGTH: 24
<212> TYPE: DNA
<213> ORGANISM: Artificial sequence
<220> FEATURE:
<223> OTHER INFORMATION: hPGK-R

<400> SEQUENCE: 41
cagatgaact tcagggtcag cttg 24

<210> SEQ ID NO 42
<211> LENGTH: 31
<212> TYPE: DNA
<213> ORGANISM: Artificial sequence
<220> FEATURE:
<223> OTHER INFORMATION: Luc-F

<400> SEQUENCE: 42
tcaggatcca tctgcgatct aagtaagctt g 31

<210> SEQ ID NO 43
<211> LENGTH: 29
<212> TYPE: DNA
<213> ORGANISM: Artificial sequence
<220> FEATURE:
<223> OTHER INFORMATION: Luc-R

<400> SEQUENCE: 43
tcaactcgag ctagaattac acggcgatc 29

<210> SEQ ID NO 44
<211> LENGTH: 29
<212> TYPE: DNA
<213> ORGANISM: Artificial sequence
<220> FEATURE:
<223> OTHER INFORMATION: F8V1-F

<400> SEQUENCE: 44
gtcagatcga tgccaccatg caaatagag 29

<210> SEQ ID NO 45
<211> LENGTH: 60
<212> TYPE: DNA
<213> ORGANISM: Artificial sequence
<220> FEATURE:
<223> OTHER INFORMATION: F8V1HA-R

<400> SEQUENCE: 45
cctgctcgag tcatgcataa tcaggcacgt cataggggta gctgccgtag aggtcctgtg 60

<210> SEQ ID NO 46
<211> LENGTH: 37
<212> TYPE: DNA
<213> ORGANISM: Artificial sequence
<220> FEATURE:
<223> OTHER INFORMATION: FP-BDDF8-F

<400> SEQUENCE: 46
ccattgaacc aagaagcttc tctcaaaacc caccagt 37

<210> SEQ ID NO 47
<211> LENGTH: 37
<212> TYPE: DNA
<213> ORGANISM: Artificial sequence
<220> FEATURE:
<223> OTHER INFORMATION: FP-BDDF8-R

<400> SEQUENCE: 47
actggtgggt tttgagagaa gcttcttggt tcaatgg 37

<210> SEQ ID NO 48
<211> LENGTH: 23
<212> TYPE: DNA
<213> ORGANISM: Artificial sequence
<220> FEATURE:
<223> OTHER INFORMATION: Gag-taqman-F01

<400> SEQUENCE: 48
ggagctagaa cgattcgcag tta 23

<210> SEQ ID NO 49
<211> LENGTH: 22
<212> TYPE: DNA
<213> ORGANISM: Artificial sequence
<220> FEATURE:
<223> OTHER INFORMATION: Gag-taqman-R01

<400> SEQUENCE: 49
tgatcctgtc tgaagggatg gt 22

<210> SEQ ID NO 50
<211> LENGTH: 17
<212> TYPE: DNA
<213> ORGANISM: Artificial sequence
<220> FEATURE:
<223> OTHER INFORMATION: Gag-Probe-01

<400> SEQUENCE: 50
tcctggcctg ttagaaa 17

<210> SEQ ID NO 51
<211> LENGTH: 19
<212> TYPE: DNA
<213> ORGANISM: Artificial sequence
<220> FEATURE:
<223> OTHER INFORMATION: Hygro-taqman-F01

<400> SEQUENCE: 51
tgctccgcat tggtcttga 19

<210> SEQ ID NO 52
<211> LENGTH: 20
<212> TYPE: DNA
<213> ORGANISM: Artificial sequence
<220> FEATURE:
<223> OTHER INFORMATION: Hygro-taqman-R01

<400> SEQUENCE: 52
cttcggacga ttgcatcaca 20

<210> SEQ ID NO 53
<211> LENGTH: 15
<212> TYPE: DNA
<213> ORGANISM: Artificial sequence
<220> FEATURE:
<223> OTHER INFORMATION: Hygro-Probe-01

<400> SEQUENCE: 53
atgctgcttg ggcgc 15

<210> SEQ ID NO 54
<211> LENGTH: 26
<212> TYPE: DNA
<213> ORGANISM: Artificial sequence
<220> FEATURE:
<223> OTHER INFORMATION: REV-taqman-F01

<400> SEQUENCE: 54
aggaatagaa gaagaaggtg gagaga 26

<210> SEQ ID NO 55

```
<211> LENGTH: 18
<212> TYPE: DNA
<213> ORGANISM: Artificial sequence
<220> FEATURE:
<223> OTHER INFORMATION: REV-taqman-R01

<400> SEQUENCE: 55

gcacaggctc cgcagatc                                              18


<210> SEQ ID NO 56
<211> LENGTH: 20
<212> TYPE: DNA
<213> ORGANISM: Artificial sequence
<220> FEATURE:
<223> OTHER INFORMATION: REV-Probe-01

<400> SEQUENCE: 56

attcgattag tgaacggatc                                            20


<210> SEQ ID NO 57
<211> LENGTH: 20
<212> TYPE: DNA
<213> ORGANISM: Artificial sequence
<220> FEATURE:
<223> OTHER INFORMATION: VSVG-taqman-F01

<400> SEQUENCE: 57

attgcccgtc aagctcagat                                            20


<210> SEQ ID NO 58
<211> LENGTH: 22
<212> TYPE: DNA
<213> ORGANISM: Artificial sequence
<220> FEATURE:
<223> OTHER INFORMATION: VSVG-taqman-R01

<400> SEQUENCE: 58

ccgtctgctt gaatagcctt gt                                         22


<210> SEQ ID NO 59
<211> LENGTH: 22
<212> TYPE: DNA
<213> ORGANISM: Artificial sequence
<220> FEATURE:
<223> OTHER INFORMATION: VSVG-Probe-01

<400> SEQUENCE: 59

tacaagtcaa aatgcccaag ag                                         22
```